(12) United States Patent
Loper et al.

(10) Patent No.: US 11,931,279 B2
(45) Date of Patent: Mar. 19, 2024

(54) DEVICES AND METHODS FOR PLACING A GASTROINTESTINAL DEVICE

(71) Applicant: Morphic Medical, Inc., Boston, MA (US)

(72) Inventors: James Loper, Wales, MA (US); Ryan Hanlon, Hudson, NH (US); Andres Chamorro, III, Ashland, MA (US)

(73) Assignee: Morphic Medical, Inc., Boston, MA (US)

( * ) Notice: Subject to any disclaimer, the term of this patent is extended or adjusted under 35 U.S.C. 154(b) by 343 days.

(21) Appl. No.: 17/103,522

(22) Filed: Nov. 24, 2020

(65) Prior Publication Data

US 2021/0220159 A1   Jul. 22, 2021

Related U.S. Application Data

(63) Continuation of application No. 15/550,857, filed as application No. PCT/US2016/017497 on Feb. 11, 2016, now abandoned.

(60) Provisional application No. 62/116,000, filed on Feb. 13, 2015.

(51) Int. Cl.
   *A61F 5/00*      (2006.01)
   *A61M 25/00*    (2006.01)
   *A61M 25/01*    (2006.01)

(52) U.S. Cl.
   CPC .......... *A61F 5/0076* (2013.01); *A61F 5/0089* (2013.01); *A61M 25/0097* (2013.01); *A61M 25/013* (2013.01); *A61M 25/0136* (2013.01)

(58) Field of Classification Search
   CPC .................. A61F 5/0089; A61M 25/0136
   See application file for complete search history.

(56) References Cited

U.S. PATENT DOCUMENTS

| 4,315,509 | A | | 2/1982 | Smit |
| 5,273,053 | A | * | 12/1993 | Pohndorf .............. A61N 1/057 607/132 |
| 5,306,300 | A | | 4/1994 | Berry |
| 5,820,584 | A | | 10/1998 | Crabb |
| 6,152,910 | A | | 11/2000 | Agro et al. |

(Continued)

OTHER PUBLICATIONS

International Search Report and Written Opinion for International Patent Application No. PCT/US2016/017497, dated Jul. 19, 2016 (17 pages).

*Primary Examiner* — Jessica Arble
(74) *Attorney, Agent, or Firm* — Clark & Elbing LLP

(57) ABSTRACT

A delivery system for placing a gastrointestinal device in a mammalian gastrointestinal tract comprises a container assembly; a gastrointestinal implant device that includes proximal and distal ends stored within the container assembly, the proximal end including an anchor and the distal end including a sleeve, coupled to the anchor and folded into the container assembly; and an inner extension to draw a portion of the sleeve from the anchor and from the container assembly as the anchor is retained therein. The inner extension comprises an atraumatic tip, such as a ball, that includes a guidewire rail. Further, a handle is provided that retains or captures an inner catheter within the handle. Within the handle is an elongated element that surrounds a portion of the catheter. A button on a side of the handle is configured to cause engagement of the catheter via the element when the button is depressed.

15 Claims, 56 Drawing Sheets

(56) References Cited

U.S. PATENT DOCUMENTS

| | | |
|---|---|---|
| 7,025,791 B2 | 4/2006 | Levine et al. |
| 7,122,058 B2 | 10/2006 | Levine et al. |
| 7,476,256 B2 | 1/2009 | Meade et al. |
| 7,766,973 B2 | 8/2010 | Levine et al. |
| 7,815,589 B2 | 10/2010 | Meade et al. |
| 7,815,591 B2 | 10/2010 | Levine et al. |
| 7,837,643 B2 | 11/2010 | Levine et al. |
| 2004/0220682 A1 | 11/2004 | Levine et al. |
| 2004/0249362 A1 | 12/2004 | Levine et al. |
| 2005/0131449 A1 | 6/2005 | Salahieh et al. |
| 2006/0009858 A1 | 1/2006 | Levine et al. |
| 2006/0135948 A1 | 6/2006 | Varma |
| 2011/0009889 A1 | 1/2011 | Shamay |
| 2015/0012008 A1 | 1/2015 | McWeeney |

* cited by examiner

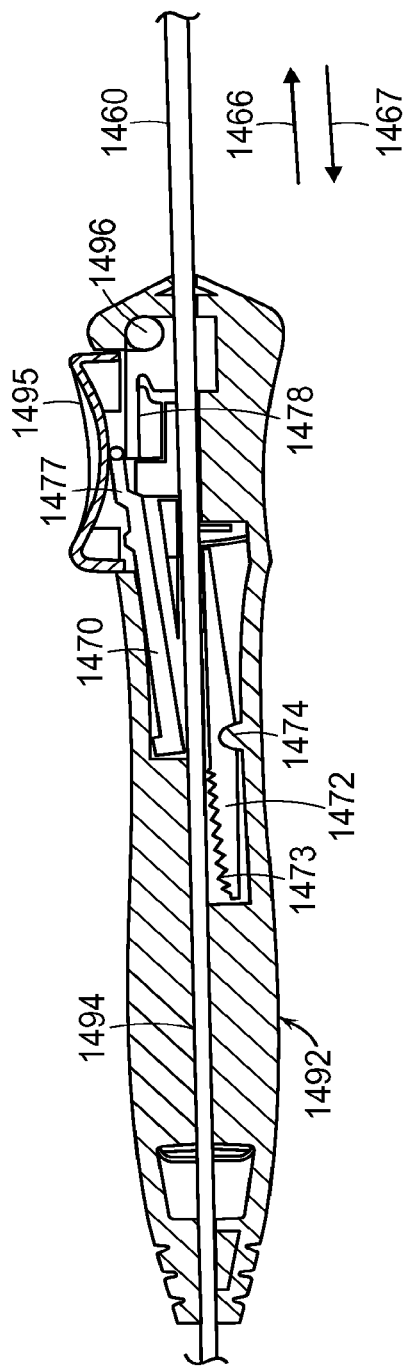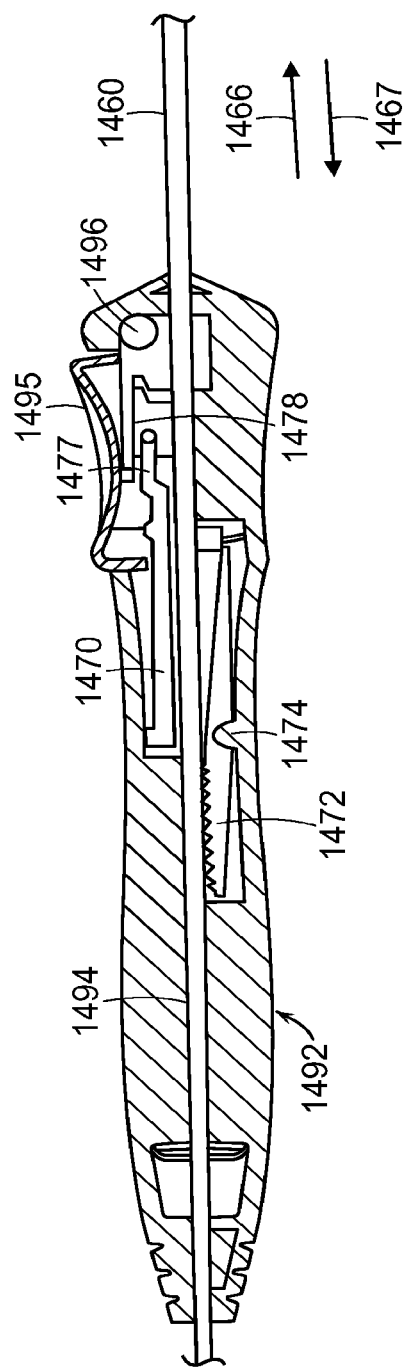
FIG. 9A
FIG. 9B

DEVICES AND METHODS FOR PLACING A GASTROINTESTINAL DEVICE

RELATED APPLICATION

This application claims the benefit of U.S. Provisional Application No. 62/116,000 filed Feb. 13, 2015. The entire teachings of the above application are incorporated herein by reference.

BACKGROUND OF THE INVENTION

Obesity is an overwhelming health problem. According to the Center for Disease Control (CDC), over sixty percent of the United States population is overweight, and almost twenty percent are obese. This translates into about 40 million adults in the United States with a Body Mass Index (BMI) of 30 or above. The BMI is defined as a person's weight (in kilograms) divided by height (in meters), squared. To be considered clinically, morbidly obese, one must meet one of three criteria: a Body Mass Index of more than 35, one hundred pounds overweight, or 100% above ideal body weight. There is also a category for the super-obese for those weighing over 350 lbs.

Although the physiology and psychology of obesity are complex, the medical consensus is that the cause is quite simple: over consumption of calories combined with a reduction in energy expenditures seen in modern society. While the treatment seems quite intuitive, the institution of a cure is a complex issue that has so far vexed the best efforts of medical science. Dieting is not an adequate long-term solution for most people. Once an individual has slipped past the BMI of 30, significant changes in lifestyle are the only solution.

There have been many attempts in the past to surgically modify patients' anatomies to attack the consumption problem by reducing the desire to eat. Stomach saplings, or gastroplasties, to reduce the volumetric size of the stomach, therein achieving faster satiety, were performed in the 1980's and early 1990's. Although able to achieve early weight loss, sustained reduction was not obtained. The reasons are not all known, but are believed related to several factors. One of which is that the stomach stretches over time increasing volume while psychological drivers motivate patients to find creative approaches to literally eat around the smaller pouch.

There are currently two surgical procedures that successfully produce long-term weight loss; the Roux-en-Y gastric bypass and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the duodenum makes it more difficult to digest fats, high sugar and carbohydrate rich foods. One objective of the surgery is to provide feedback to the patient by producing a dumping syndrome if they do eat these food products. Dumping occurs when carbohydrates directly enter the jejunum without being first conditioned in the duodenum. The result is that a large quantity of fluid is discharged into the food from the intestinal lining. The total effect makes the patient feel light-headed and results in severe diarrhea. For reasons that have not been determined the procedure also has an immediate therapeutic effect on diabetes, a co-morbidity associated with obesity.

Although the physiology seems simple, the exact mechanism of action in these procedures is not understood. Current theory is that negative feedback is provided from both regurgitation into the esophagus and dumping when large volumes of the wrong foods are eaten. Eventually, patients learn that to avoid both these issues they must be compliant with the dietary restrictions imposed by their modified anatomy. In the BPD procedure, large lengths of jejunum are bypassed resulting in malabsorption and therefore, reduced caloric uptake. In fact, the stomach is not reduced in size as much in the BPD procedure so that the patient is able to consume sufficient quantities of food to compensate for the reduced absorption. This procedure is reserved for the most morbidly obese as there are several serious side effects of prolonged malabsorption.

Unfortunately, these procedures carry a heavy toll. The morbidity rate for surgical procedures is alarmingly high with 11% requiring surgical intervention for correction. Early small bowel obstruction occurs at a rate of between 2-6% in these surgeries and mortality rates are reported to be approximately 0.5-1.5%. While surgery seems to be an effective answer, the current invasive procedures are not acceptable with these complication rates. Laparoscopic techniques applied to these surgeries provide fewer surgical complications but continue to expose these very ill patients to high operative risk in addition to requiring an enormous level of skill by the surgeon. Devices to reduce absorption in the small intestines have been proposed (see U.S. Pat. No. 5,820,584 (Crabb), U.S. Pat. No. 5,306,300 (Berry) and U.S. Pat. No. 4,315,509 (Smit)). However, these devices have not been successfully implemented.

Various gastrointestinal implants have been developed as potential solutions to these above problems. However, a need exists for methods and devices to place or position these implants within mammalian gastrointestinal tracts.

SUMMARY OF THE INVENTION

This invention is generally directed towards methods, devices, and systems for implanting or placing a gastrointestinal device (e.g., a gastrointestinal sleeve) into the gastrointestinal tract of a mammal (e.g., a human). The methods utilize, and the devices include, a container assembly and a gastrointestinal device having a proximal end that includes an anchor and a distal end that includes a sleeve. Furthermore, the invention is directed to catheter handles for a delivery system of a gastrointestinal device and methods of retaining or capturing an inner catheter for delivery of a gastrointestinal device.

In an embodiment according to the invention, there is provided a delivery system for placing a gastrointestinal device in a mammalian gastrointestinal tract. The system comprises a container assembly; a gastrointestinal implant device that includes a proximal end and a distal end stored within the container assembly, the proximal end including an anchor and the distal end including a floppy sleeve, coupled to the anchor and folded into the container assembly; and an inner extension to draw a portion of the sleeve from the anchor and from the container assembly as the anchor is retained therein. The inner extension comprises an atraumatic tip that comprises a guidewire rail.

The inner extension may comprise a catheter releasably secured to the distal end of the sleeve. The atraumatic tip may comprise a ball. The guidewire rail may comprise a channel that runs within the interior of the atraumatic tip. The guidewire rail may run from a distal center of the atraumatic tip to a proximal off-center side of the atraumatic tip.

In another embodiment according to the invention, there is provided a method for placing a gastrointestinal device in a mammalian gastrointestinal tract. The method comprises guiding a delivery system over a guidewire within the gastrointestinal tract by advancing an atraumatic tip over the guidewire as the guidewire runs through a guidewire rail of the atraumatic tip; and drawing the gastrointestinal device out of a container assembly using an inner extension from the container assembly, the inner extension comprising the atraumatic tip at a distal end of the inner extension.

In another embodiment according to the invention, there is provided a catheter handle for a delivery system of a gastrointestinal device. The catheter handle includes an inner catheter movable within the handle; an elongated element within the handle, the element surrounding a portion of the inner catheter, an inner diameter of the element being about the same as or greater than an outer diameter of the inner catheter. A button is on a side of the handle, the button configured to cause engagement of the inner catheter via the element when the button is depressed, thereby retaining or capturing the inner catheter within the handle.

In one example, the elongated element is a surround tube, surrounding at least a portion of the inner catheter, an inner diameter of the surround tube being about the same or greater than an outer diameter of the inner catheter. The button can be configured to bend the surround tube and non-plastically deform the inner catheter when the button is depressed, thereby retaining or capturing the inner catheter. In further, related embodiments, the surround tube may comprise a silicone tube. The button may comprise a rigid thermoplastic, such as, for example, Acrylonitrile Butadiene Styrene (ABS). The button may bend the surround tube between ends of the surround tube, the ends being held in place by the handle.

In another example, the elongated element is a lever including a lever jaw. The button on a side of the handle is configured to cause the lever to rotate about a pivot and the lever jaw to engage the inner catheter when the button is depressed, thereby retaining or capturing the inner catheter within the handle. The lever can define a lumen through which the inner catheter extends and the lever jaw can include directional teeth, e.g., to engage the inner catheter and aid in pushing the inner catheter retained by the handle. The lever may be configured to translate a force with which the button is depressed into a force with which the inner catheter is engaged at an amplification ratio (engagement force:depression force) in the range of about 1:1 to about 2:1, preferably in the range of about 1.3:1 to about 1.7:1. The catheter handle can further include a resilient element, e.g., a spring, configured to non-plastically deform when the button is depressed and to provide a restoring force to cause the lever jaw to disengage the inner catheter when the button is released.

In another example, the elongated element includes slots and the button includes ramped teeth aligned with the slots. The button on a side of the handle is configured to cause the ramped teeth to engage the inner catheter via the slots when the button is depressed and press the inner catheter against the element, thereby retaining the inner catheter within the handle. The slots, which may be ramped, can be transverse slots spaced along a length of the elongated element on two sides of the element. Further, slots on one side of the elongated element can be offset from the slots on the other side of the element. Further, ramped teeth and ramped slots may define multiple complementary features. The catheter handle can further include a resilient element configured to non-plastically deform when the button is depressed and to provide a restoring force to cause the ramped teeth to disengage the inner catheter when the button is released.

The inner catheter may include an inner extension catheter configured to draw a portion of a sleeve from an anchor and from the container assembly as the anchor is retained therein into a gastrointestinal tract. Alternatively, the inner catheter may include a delivery catheter configured to deliver a container assembly.

In another embodiment according to the invention, there is provided a method of retaining or capturing an inner catheter for delivery of a gastrointestinal device. The method includes surrounding a portion of an inner catheter that is movably disposed within a handle with an elongated element within the handle; depressing a button on a side of the handle, to engage the inner catheter via the elongated element; and retaining or capturing the inner catheter based on the resulting engagement of the inner catheter.

For example, the elongated element can be a surround tube, and depressing the button can bend the surround tube and non-plastically deform the inner catheter.

The elongated element can be a lever including a lever jaw, and depressing the button can cause the lever to rotate about a pivot and the jaw of the lever to engage the inner catheter.

The elongated element can include ramped slots and the button can include ramped teeth aligned with the slots. Depressing the button can cause the ramped teeth to engage the inner catheter via the slots and press the inner catheter against the element.

In further related embodiments, the method may further comprise delivering a container assembly into at least a portion of the gastrointestinal tract using the inner catheter. The method may further comprise drawing a portion of a sleeve from an anchor, and from a container assembly, as the anchor is retained therein, using the inner catheter.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 4A-4L illustrate a gastrointestinal implant delivery catheter system and a method of use.

FIGS. 9A-9B illustrate sectional views of another embodiment of a catheter pusher handle.

FIGS. 11A and 11B are perspective and sectional views, respectively, of the catheter pusher handle. FIG. 11C is a sectional view of the catheter pusher handle of FIG. 11A illustrating engagement of the inner catheter button. FIGS. 11D and 11E are front views of the catheter pusher handle of FIGS. 11B and 11C, respectively.

FIG. 11F shows the handle when the button is released and the inner catheter disengaged. FIG. 11G shows the handle when the button is depressed and the inner catheter engaged.

DETAILED DESCRIPTION OF THE INVENTION

A description of example embodiments of the invention follows.

This invention features devices and methods for implanting or placing gastrointestinal implant devices (e.g., intestinal sleeves) into mammals (e.g., a human). Several gastrointestinal implant devices (e.g., intestinal sleeves) have been developed and are suitable for implementation or placement within a gastrointestinal tract using the methods and devices of this invention. Some examples of such devices are described in U.S. Pat. Nos. 7,025,791; 7,122,058; 7,476,256; 7,766,973; 7,815,589; 7,815,591; and in U.S. patent application Ser. No. 10/810,317, filed Mar. 26, 2004, and entitled "Enzyme Sleeve;" U.S. patent application Ser. No. 10/811,293, filed Mar. 26, 2004, and entitled "Anti-Obesity Devices;" and U.S. Provisional Application No. 60/645,287, filed Jan. 19, 2005, entitled "Anchoring Devices." The teachings of each of these patents and applications are incorporated herein by reference.

FIGS. 1A-4L are prior art taken from U.S. Pat. No. 7,837,643 to Levine et al., the teachings of which are incorporated by reference in their entirety.

Figure 1A:
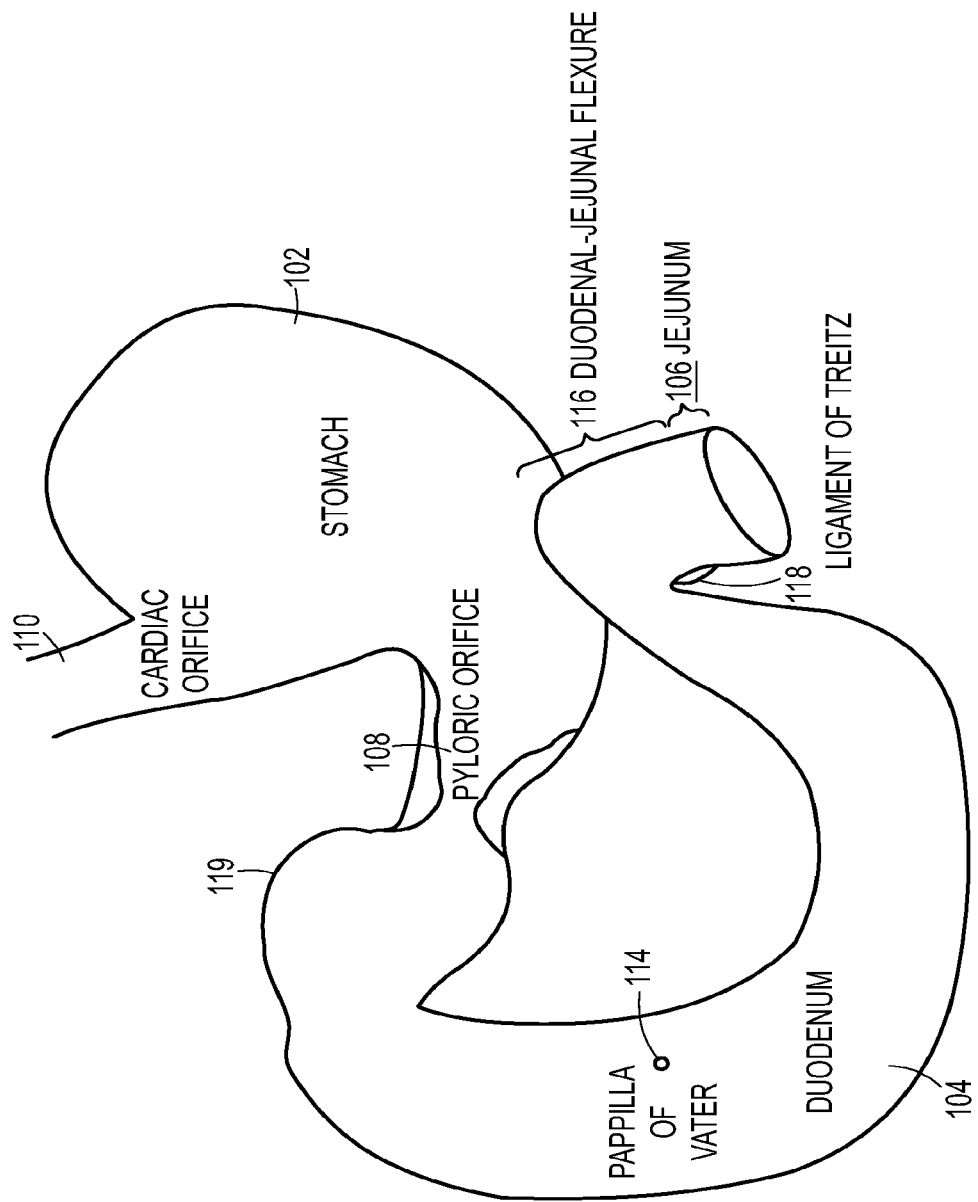
FIG. 1A is a sectional view of a portion of the digestive tract in a mammalian body.

FIG. 1A is a sectional view of a portion of the digestive tract in a mammalian body. Food to be digested enters the stomach 102 through the cardiac orifice 110 from the esophagus. Chyme, a semi-fluid, homogeneous creamy or gruel-like material produced by gastric digestion in the stomach exits the stomach through the pyloric orifice or pylorus 108 and enters the small intestine.

The pylorus 108 is a distal aperture of the stomach 102 surrounded by a strong band of circular muscle. The small intestine, about 15-20 feet in length, is a convoluted tube, extending from the pylorus 108 to the ileo-caecal valve where it terminates in the large intestine. The small intestine has three sections, the duodenum 104, jejunum 106 and the ileum (not shown in FIG. 1). The duodenum 104 makes up the first 10-12 inch section of the small intestine and tends to be the shortest, widest, and most fixed part of the small intestine.

The duodenum 104 has four sections which typically form a U shape: superior, descending, transverse, and ascending. The superior section is about two inches long and ends at the neck of the gall bladder. The superior section also defines a feature referred to as the duodenal bulb 119 that begins just distal to the pylorus 108 and extends for about 1 to 1.5 inches in an adult human. The duodenal bulb 119 defines a lumen therein that is slightly larger than the distal duodenum 104. Advantageously, the duodenal bulb 119 exhibits less motion than the pylorus 108 and even distal portions of the duodenum 104. Notably, the motion is substantially limited to contractions without having a significant linear component (i.e., no movement along the central axis of the intestine). The tissue of the intestinal wall of the pylorus 108, and to some extent that of the duodenal bulb 119, tends to be thicker than that of other portions of the small intestine, but the tissue thins as one moves away from the pylorus 108.

The descending section of the duodenum 104 is about three to four inches long and includes a nipple shaped structure, the papilla of Vater 114, through which pancreatic juice from the pancreas and bile produced by the liver and stored by the gall bladder enter the duodenum from the pancreatic and bile ducts. The pancreatic juice contains enzymes essential to protein digestion and bile dissolves the products of fat digestion. The ascending section is about two inches long and forms the duodenal-jejunal flexure 116 where it joins the jejunum 106, the next section of the small intestine. The duodenal-jejunal flexure 116 is fixed to the ligament of Treitz 118 (musculus supensionus duodeni). The juices secreted in the duodenum break the partially digested food down into particles small enough to be absorbed by the body. The digestive system is described in Gray's Anatomy ("Anatomy of the Human Body," by Henry Gray) and "Human Physiology," Vander, 3rd ed, McGraw Hill, 1980, the contents of which are incorporated herein by reference in their entirety.

This invention includes methods and devices for placing or implanting a gastrointestinal implant device in a mammal. For example, this invention includes methods and devices for implanting a gastrointestinal sleeve. In some embodiments, the gastrointestinal sleeve includes an anchor portion and a floppy, flexible, thin, conformable, and/or collapsible sleeve portion.

Figure 1B:
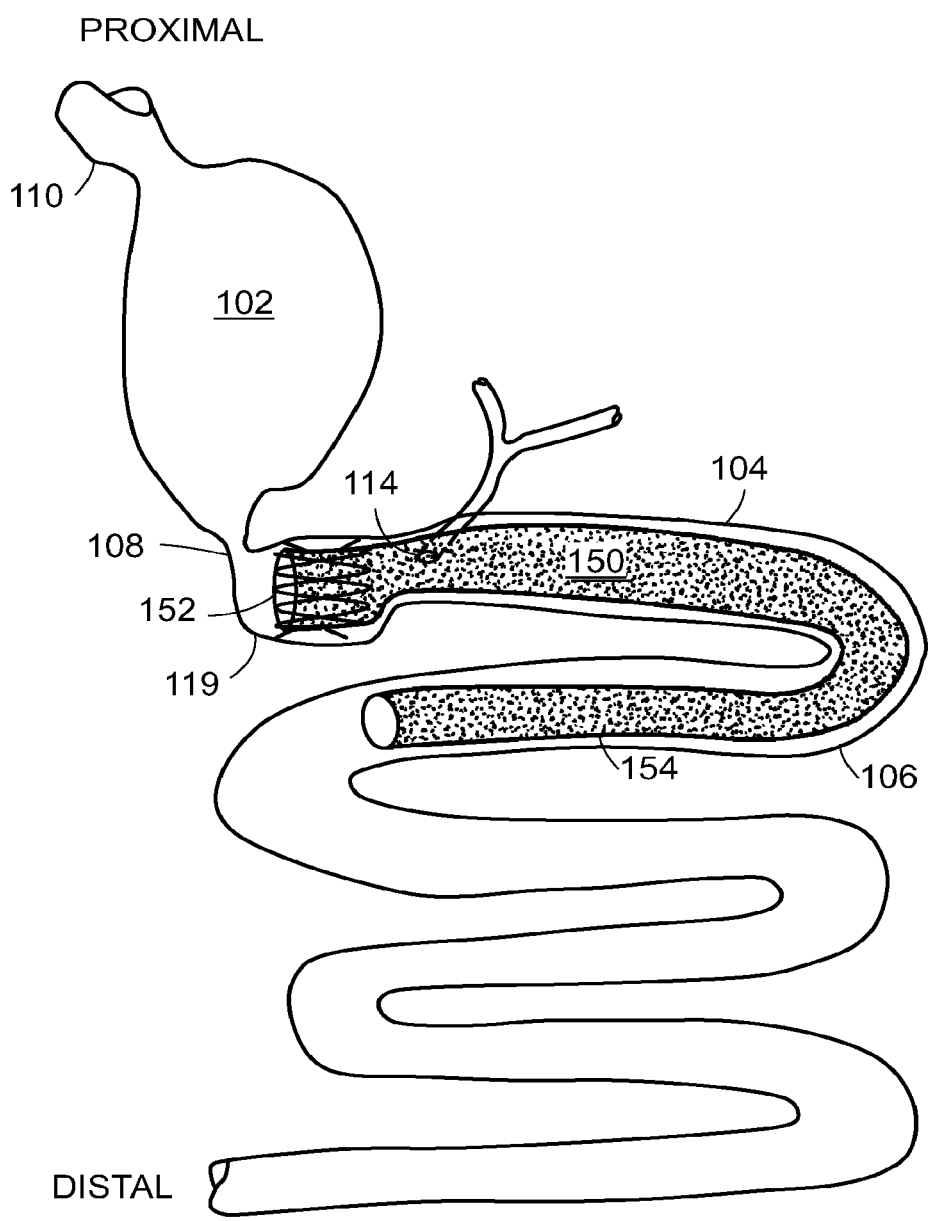
FIG. 1B illustrates a gastrointestinal implant device after it has been implanted into the gastrointestinal tract of a mammal.

FIG. 1B illustrates gastrointestinal implant device 150 after it has been implanted into the gastrointestinal tract of a mammal using embodiments of the methods and devices of this invention. Gastrointestinal implant device comprises a proximal portion or end that includes anchor 152 and a distal portion or end that includes a barrier or sleeve 154. When implanted, as shown in FIG. 1B, the central axis of anchor 152 is substantially aligned with the central axis of the duodenum, allowing chyme to pass through device 150. Additionally, anchor 152 minimizes trauma to the tissue by providing sufficient flexibility and compliance, minimizes the likelihood of tissue erosion, and provides a solid anchoring point to the tissue.

Anchor 152 can be removably attached within the body using the methods described herein, including the use of barbs attached to, and/or formed on, the anchor itself. In some embodiments, the anchor is attached or secured within the gastrointestinal tract without the use of barbs. When implanted, anchor 152 allows sleeve 154 to be securely implanted within the duodenum, preferably providing a fluid seal at the proximal end.

In some embodiments, the device is anchored in the bulbous duodenum. For purposes of anchoring a gastrointestinal device, the bulbous duodenum offers several advantages over other areas in of gastrointestinal tract. First, the duodenal bulb is proportionally sized to capture an anchor. That is, it provides a cavity having a relatively large diameter bounded by anatomies having smaller diameters in both the proximal and distal directions. Thus, the duodenal bulb is naturally configured to retain a suitably shaped anchor. Additionally, the duodenal bulb is relatively less active than either the pylorus or the distal portions of the duodenum. Movement of the surrounding tissue can act to dislodge an anchor over time. The duodenal bulb, at least in part, acts as a holding area for chyme received from the stomach. Thus, the duodenal bulb provides a more stable anchoring platform as there is relatively less movement than at other portions of the gastrointestinal tract. Still further, the tissue of at least the proximal portion of the duodenal bulb is thicker than the tissue of the distal duodenum, thus, the duodenal bulb provides a better anchoring platform as it is adapted to retain fasteners (e.g., barbs).

Figure 2A:
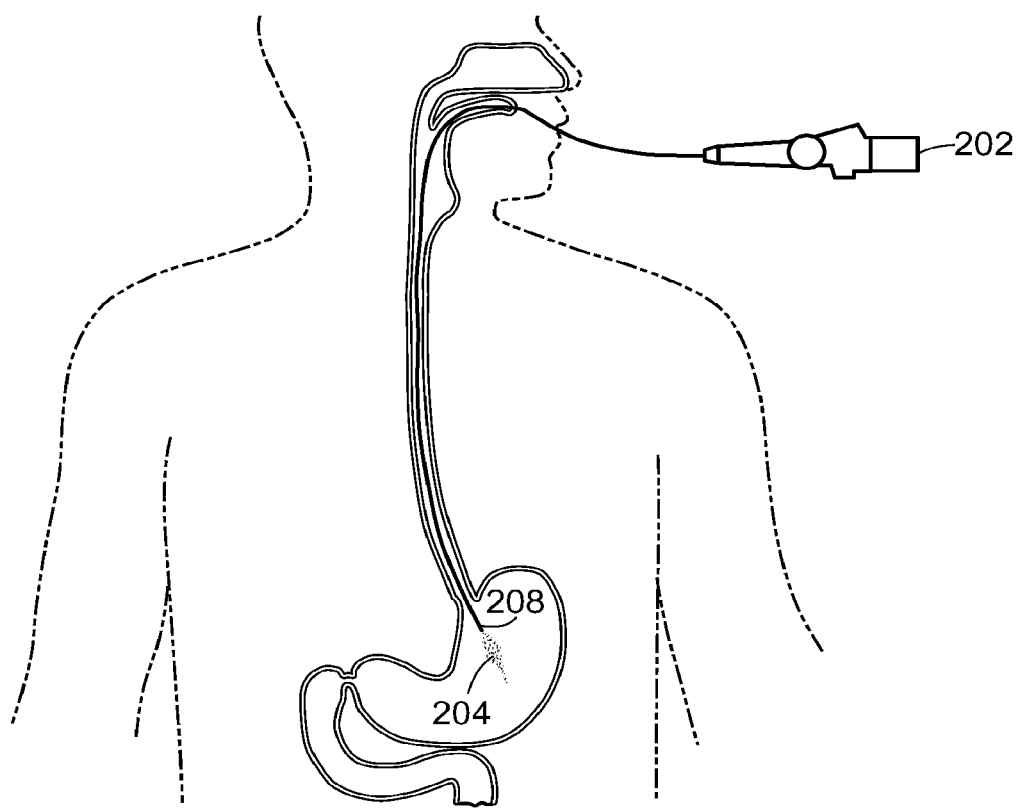
FIGS. 2A-2N are a series of sequential diagrams illustrating methods of delivering a gastrointestinal implant device.
Figure 2B:
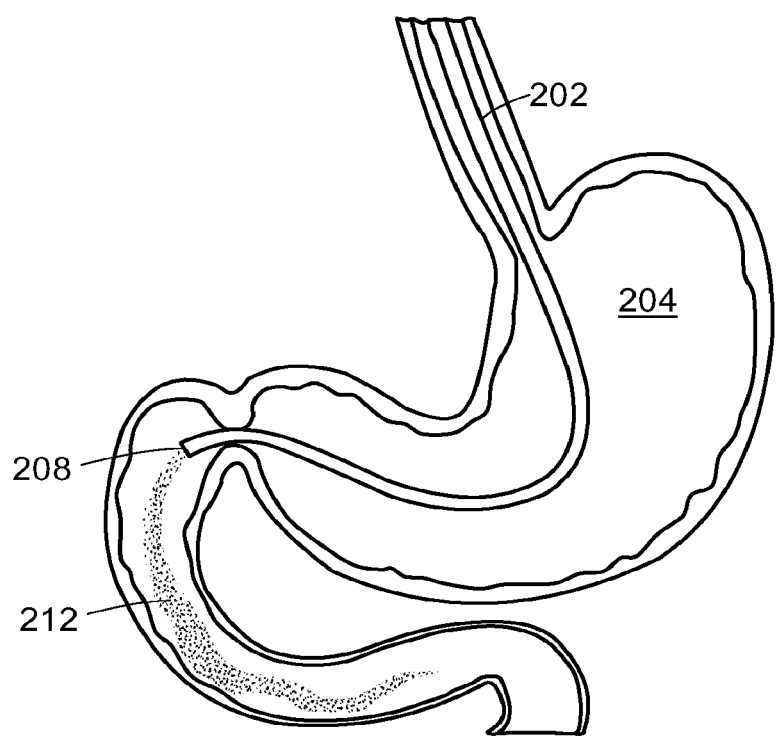
Figure 2C:
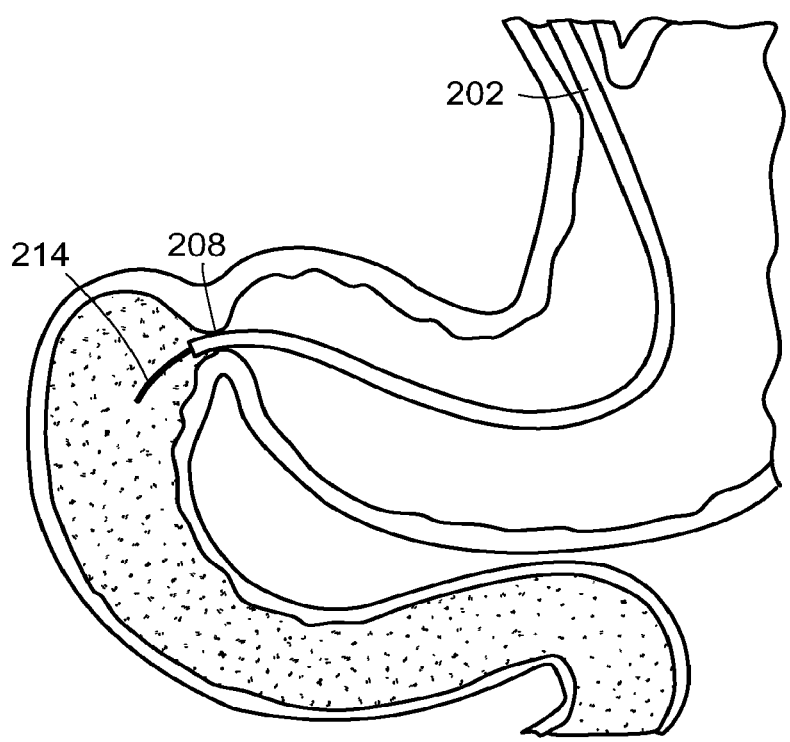
Figure 2D:
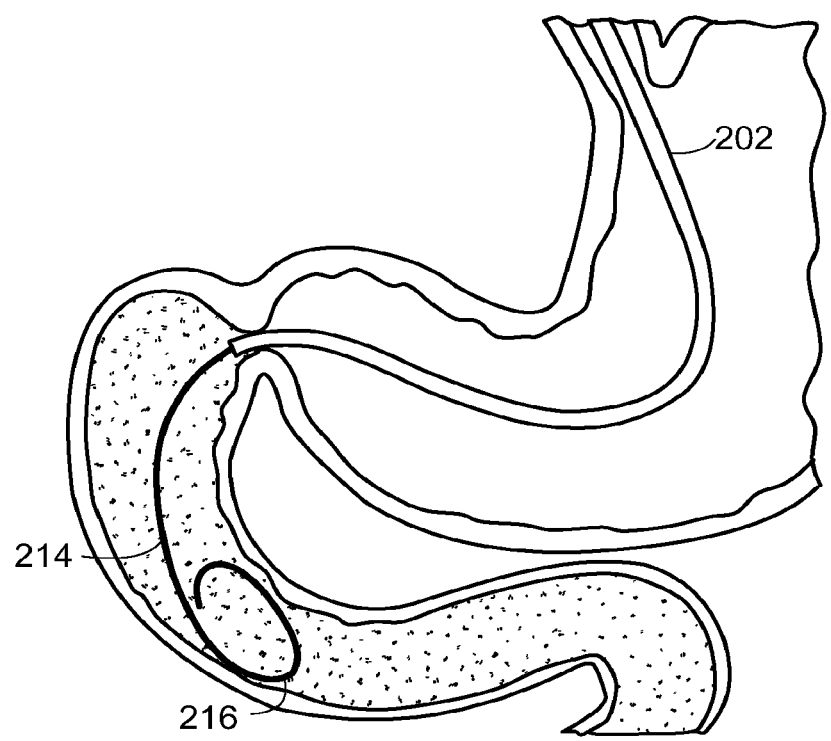
Figure 2E:
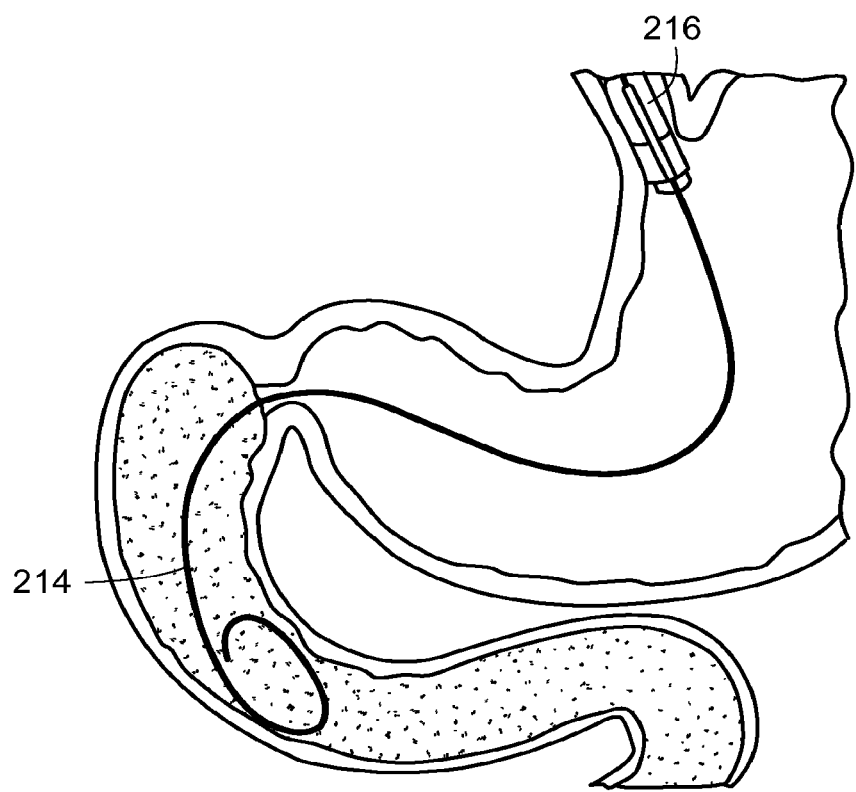
Figure 2F:
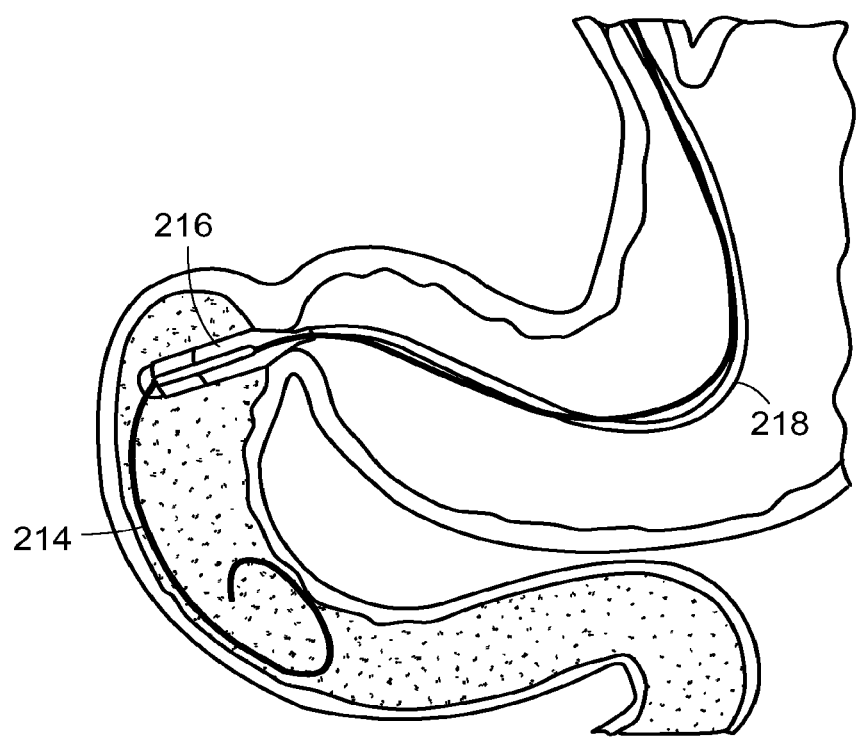
Figure 2G:
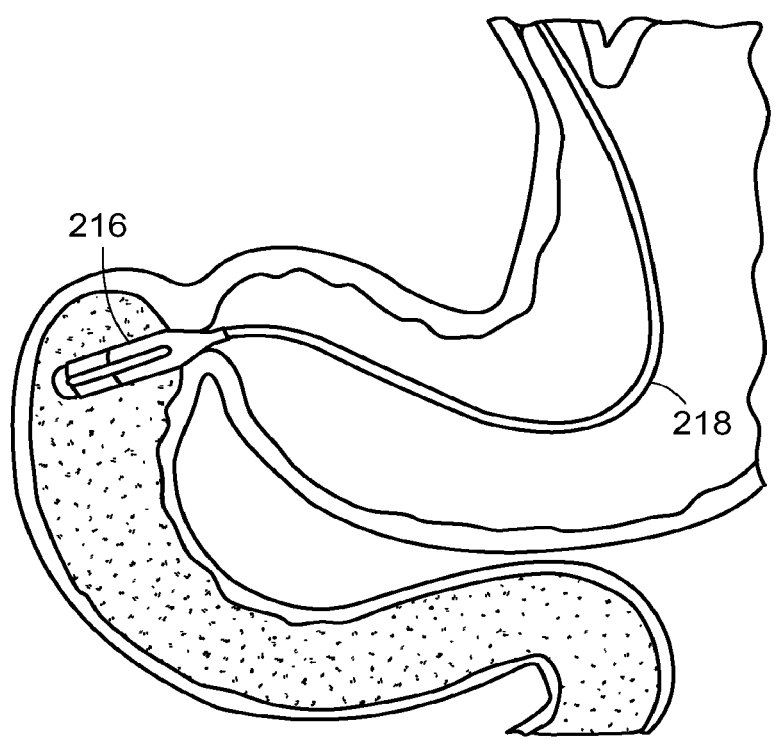
Figure 2H:
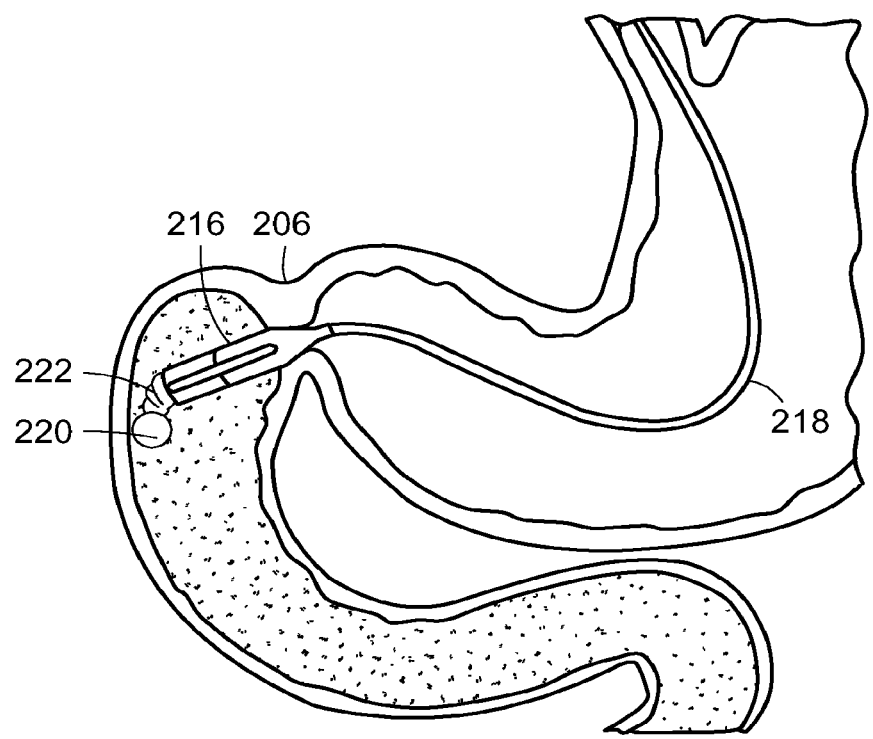
Figure 2I:
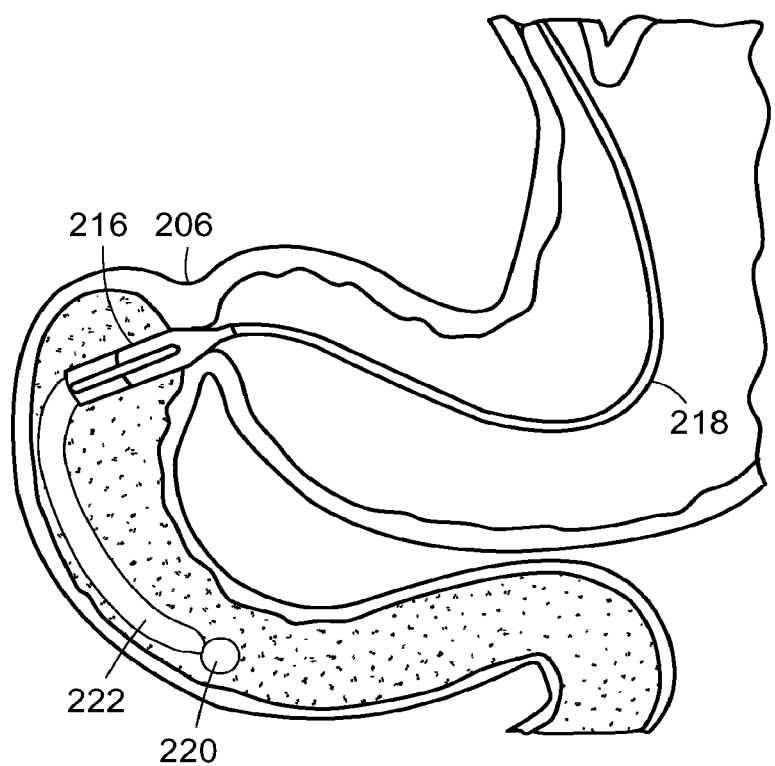
Figure 2J:
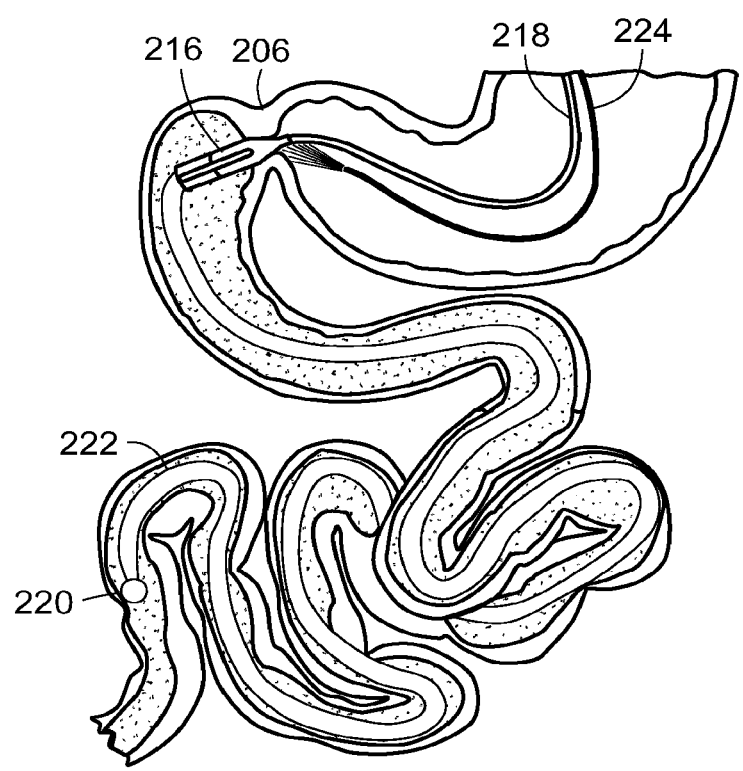
Figure 2K:
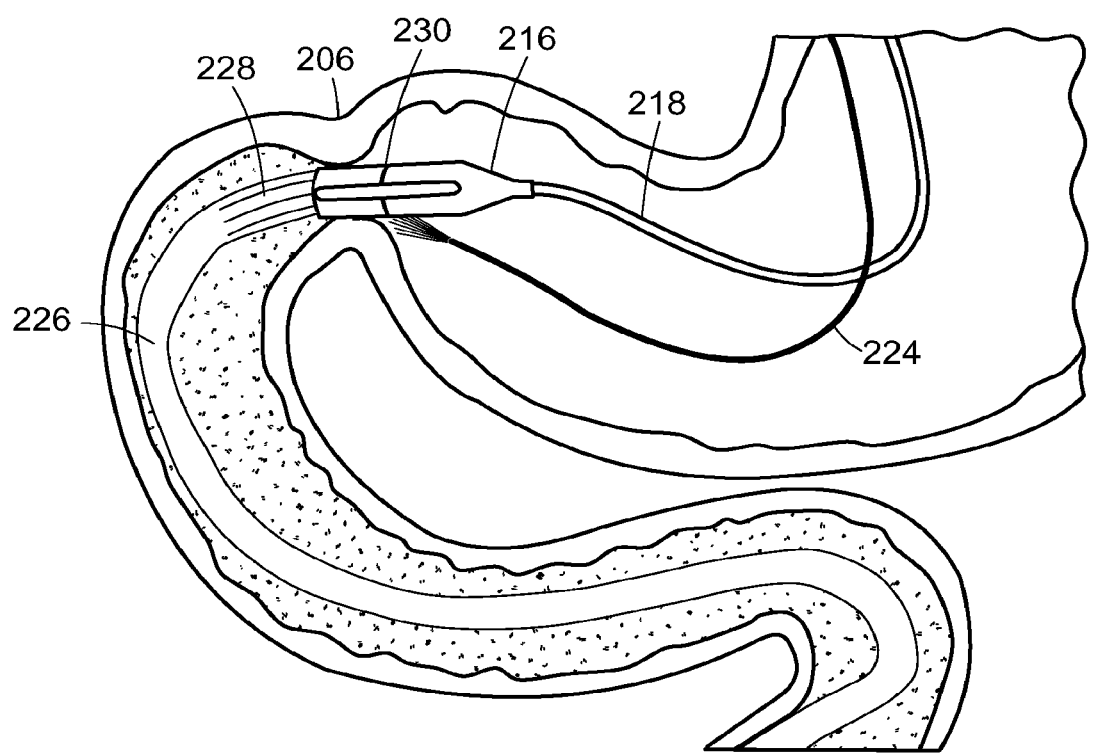
Figure 2L:
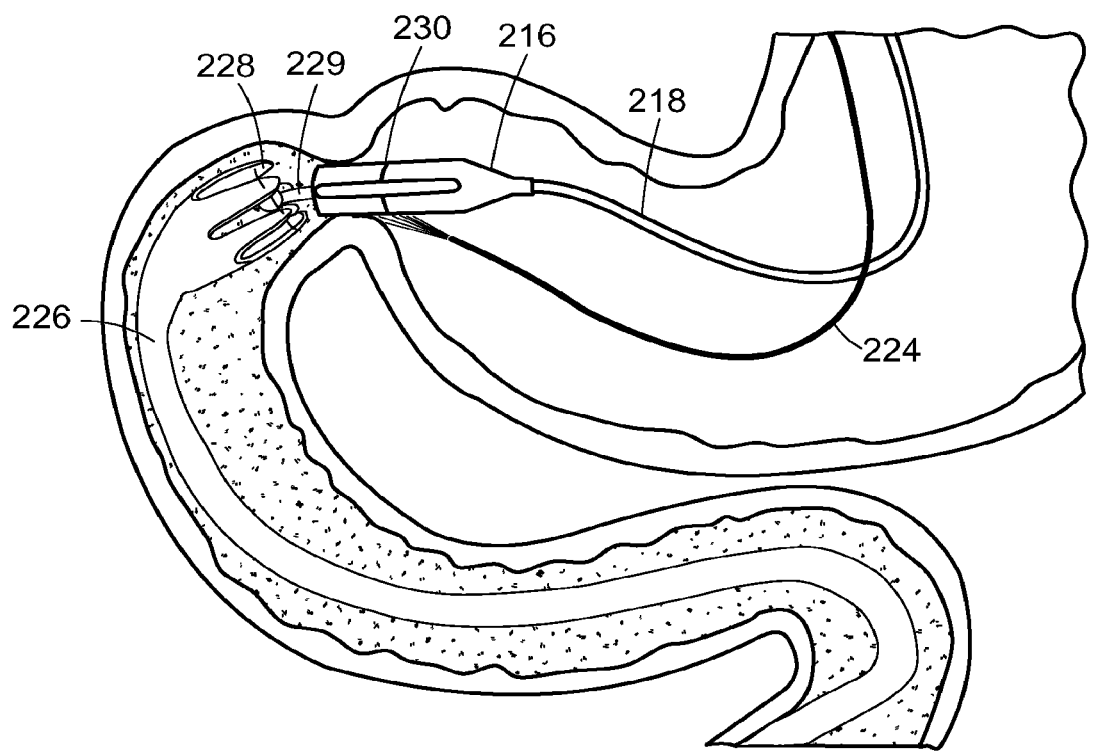
Figure 2M:
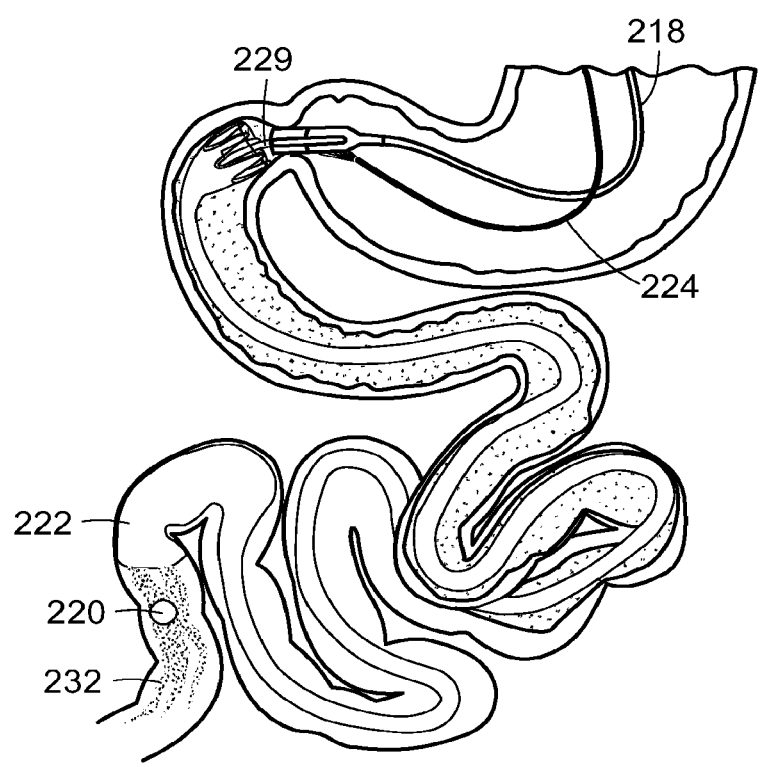
Figure 2N:
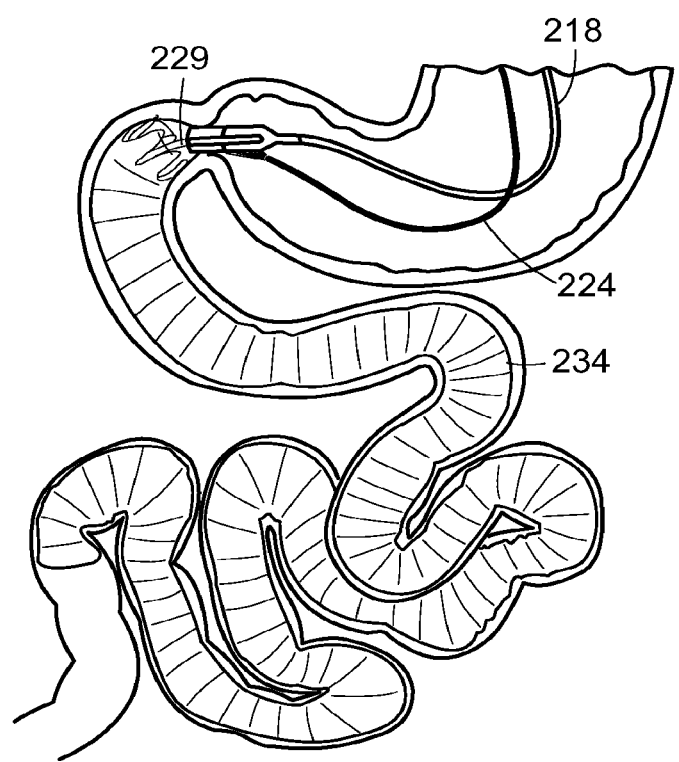

FIGS. 2A-2N are a series of sequential diagrams illustrating multiple embodiments of methods of the invention. In FIG. 2A, gastro-scope 202 (e.g., a 9.8 millimeter endoscope) is directed through the mouth of a patient, and into stomach 204. Distal end 208 of gastro-scope 202 is directed through pyloric orifice 206 and into proximal duodenum 210, as illustrated in FIG. 2B.

Optionally, a proximal portion of the small intestine (e.g., the duodenum) is expanded in order to create a working space for the practitioner. One method of expanding a proximal portion of the small intestine is to direct a fluid into the duodenum via a working channel in the gastro-scope. Examples of suitable fluids include gases (e.g., air, nitrogen, and/or carbon dioxide) or liquids (e.g., water and/or saline). In some embodiments, the fluid is a liquid mixture of saline and a contrast medium. Examples of suitable contrast mediums include a fluorescent material, a radiopaque material, or a contrast medium commonly used for intravenous urography (e.g., preparations of diatrizoate sodium and diatrizoate meglumine). In still further embodiments, the liquid is a mixture of about 75% saline and about 25% RENOGRAFIN™ (available from Bracco Diagnostics, Inc. Corporation, East Princeton, New Jersey).

The exact amount of fluid needed to sufficiently expand the duodenum will depend on variables such as the size of the patient's gastrointestinal tract, the preferences of the practitioner, and/or the length of the gastrointestinal device to be delivered. In some embodiments, at least 60 milliliters of a fluid are used to expand the duodenum. In further embodiments, at least 200 milliliters of a fluid are used to expand the duodenum. 200 milliliters of a fluid would be useful for delivering, for example, a gastrointestinal sleeve that is about two feet in length. In further embodiments, at least 500 milliliters of a fluid are used to expand the duodenum. In still further embodiments, about 600 milliliters of a fluid are used to expand the duodenum which would be useful for delivering, for example, a gastrointestinal sleeve that is about 4 feet in length.

FIG. 2B illustrates fluid 212 as it leaves distal end of 208 of gastro-scope 202. Optionally, the intestinal expansion process is monitored using fluoroscopy to ensure that the fluid is filling the intestines and not flowing proximally into the stomach. FIG. 2C illustrates the duodenum after it has been expanded to a desired extent with fluid 212.

After the small intestine has been expanded to the desired extent, a length of guidewire 214 is directed through the working channel of gastro-scope 202, out of the distal end 208, and into the proximal portion of the duodenum, as illustrated in FIGS. 2C-2D. An example of a suitable guidewire is about a 13-foot length of super-stiff 0.035 inch guidewire. Guidewire 214 is directed through gastro-scope 202 until the distal end of guidewire 214 forms a loop in the duodenum, as shown in FIG. 2D. Optionally, the presence and/or location of the loop is confirmed under fluoroscopy. Once a sufficient length of guidewire 214 is in the desired location, gastro-scope 202 can be removed while guidewire 214 is held in position.

Once the guidewire is in the desired location and the gastro-scope has been removed, a delivery catheter is directed into the duodenum, as illustrated in FIGS. 2E-2F. The leading or distal end of outer catheter 218 is attached, assembled to, or comprises a capsule or container assembly that includes capsule or container 216. Container 216 defines a guidewire lumen along its side. The proximal end of guidewire 214 is directed through the guidewire lumen, and catheter 218 is advanced or directed along guidewire 214 to a point distal from the pylorus and into a desired position in the gastrointestinal tract (e.g., a position distal to the pylorus in the proximal duodenum). Optionally, the location of capsule 216 is confirmed using fluoroscopy.

Figure 7A:
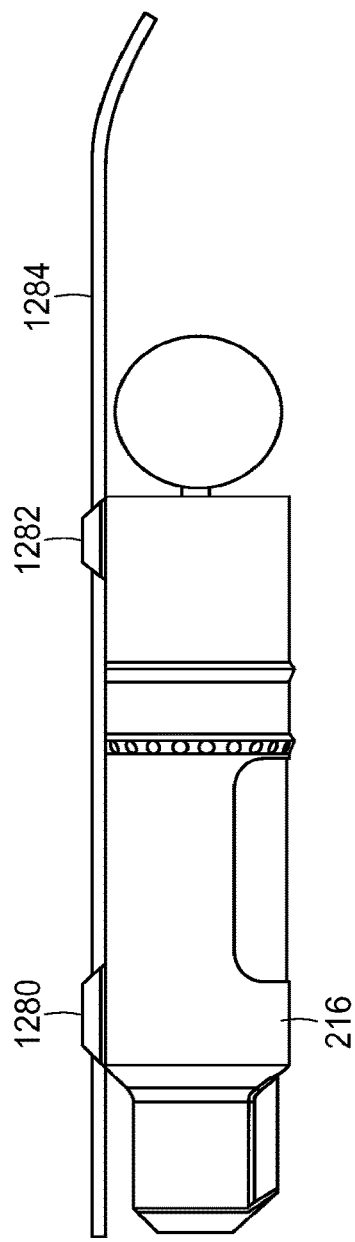
FIGS. 7A-7B illustrate a distal end of a catheter system.
Figure 7B:
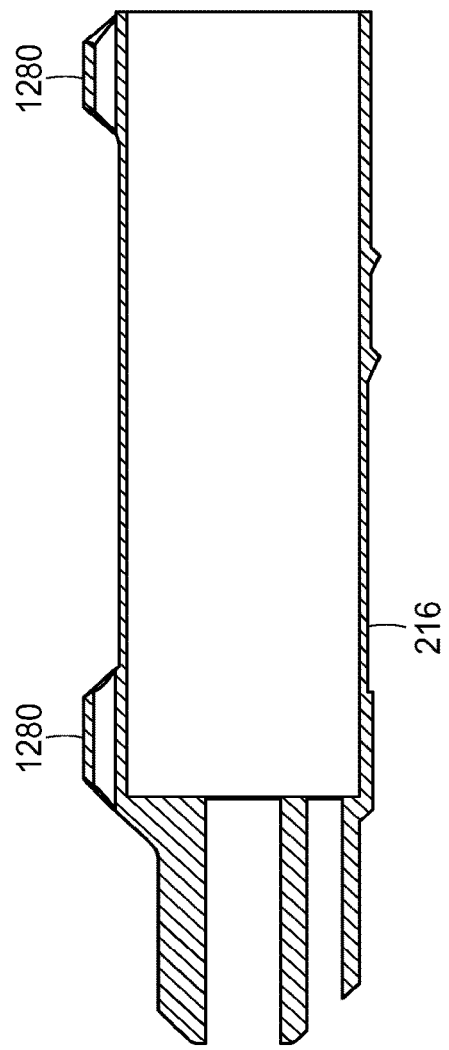

Referring to FIGS. 7A-7B, a delivery system capsule or container assembly 216 can comprise an integrated guidewire lumen or guidewire rails 1280, 1282. The guidewire lumen or guidewire rails 1280, 1282 are on the outer diameter of the capsule or off center (to a central axis of the capsule) (FIG. 7B). During a delivery procedure, the guidewire 1284 is placed in the patient and the capsule is advanced over the guidewire 1284 via the guidewire rails 1280, 1282 (FIG. 7A), for example into the esophagus and/or the duodenum.

However, in the embodiment of FIGS. 7A-7B, because the delivery system capsule is off center relative to the guidewire, there can be difficulty in advancing the capsule into the esophagus and/or the duodenum. A user typically manipulates the radial orientation of the delivery system capsule and uses the scope to move and reposition the capsule.

Figure 8A:
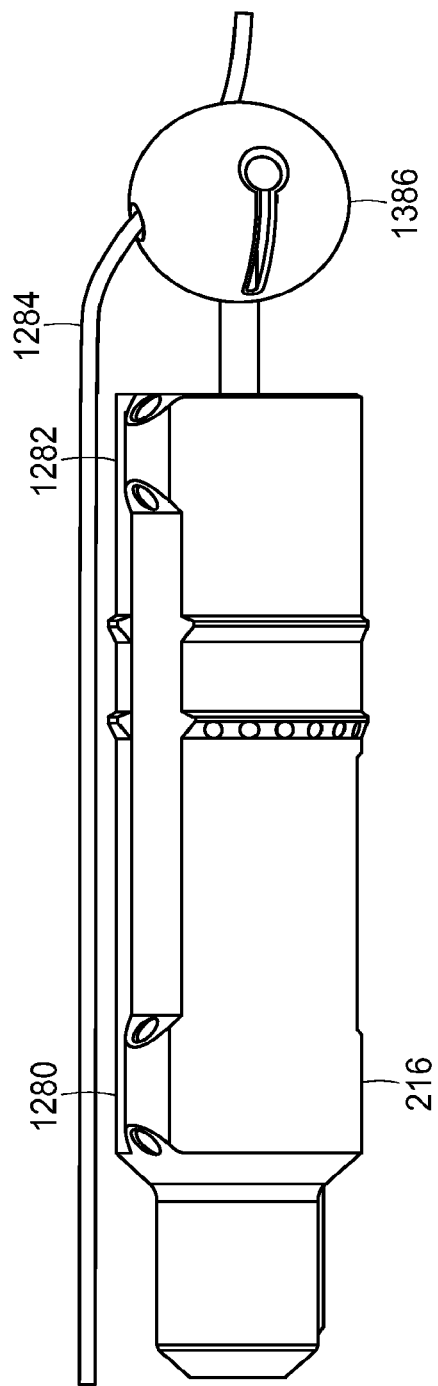
FIGS. 8A-8B illustrate an embodiment of a guidewire system at a distal end of a catheter system.
Figure 8B:
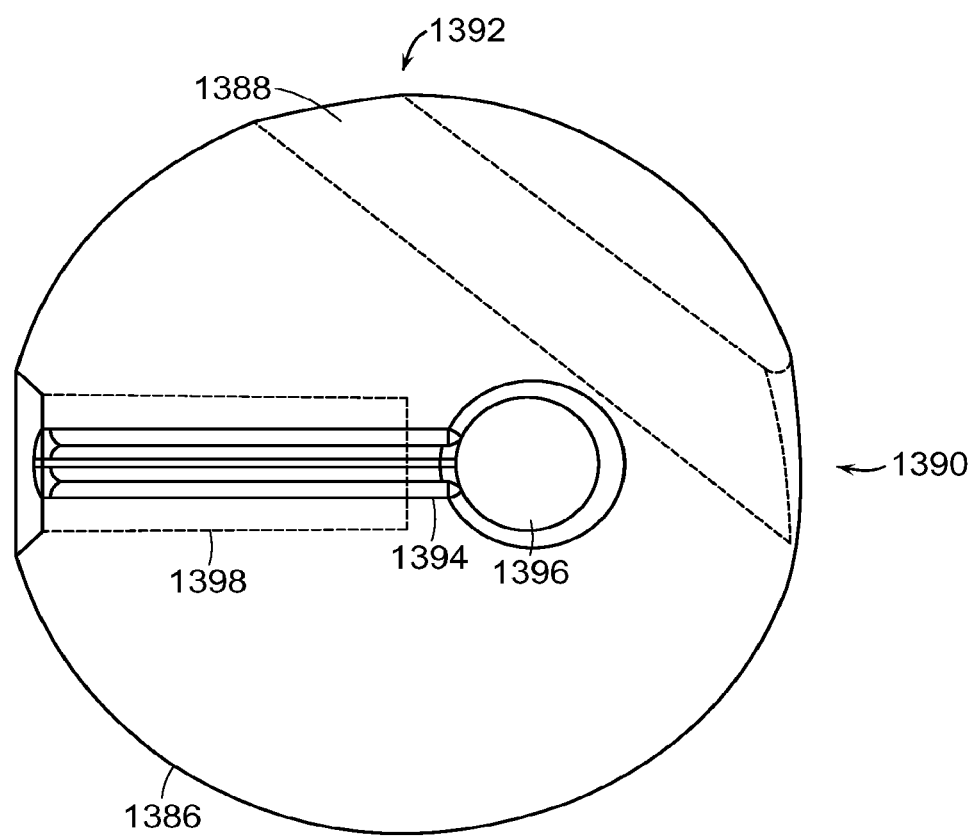

Alternatively, referring to FIGS. 8A-8B, in an embodiment according to the invention, a delivery system capsule or container 216 can comprise an inner catheter guide ball 1386 at the distal end of container 216. The guide ball forms an atraumatic tip at the distal end of the delivery system. The guide ball can be releasably attached to the distal end of the inner catheter (inner extension), as described, for example, with respect to ball 402 of FIG. 4K. The inner catheter guide ball 1386 includes an integrated guidewire rail 1388 that runs within the interior of the ball (FIG. 8B). The guidewire ball rail 1388 is angled from approximately a distal center side 1390 to a proximal off-center side 1392 of the ball. During a delivery procedure, after the guidewire is placed in the desired location in the patient, the guidewire ball 1386 is advanced over the guidewire, through the guidewire ball rail 1388 (FIG. 8B). Since the guidewire ball rail 1388 is substantially on center, the delivery system capsule 216 naturally advances into the esophagus and duodenum without the need for extra manipulation steps by the user. In this aspect, the guidewire lumen or rails 1280, 1282 found along the side of container assembly are therefore not required and may or may not be used for advancement and placement of container assembly (see FIG. 8A). Additional features of the guide ball 1386 are blind hole 1398 for receiving a distal end of the catheter, and channel 1394 and through hole 1396 for receiving a loop (e.g., a wire loop) for use with a ball release mechanism as described elsewhere herein.

Alternatively, in some embodiments of the invention, the container assembly is advanced into the stomach and the guidewire is removed. A gastro-scope is used to direct the container assembly partially or entirely through the pylorus and into the small intestine.

Once container 216 is at the desired location in the duodenum, guidewire 214 can be removed from the gastrointestinal tract, as illustrated in FIG. 2G. Optionally, prior to insertion, a lubricating jelly is applied to the surface of those portions of catheter 218 that are inserted into the gastrointestinal tract (e.g., container 216 and the distal portion of outer catheter 218).

The container holds or houses parts or all of a gastrointestinal implant device (e.g., a gastrointestinal sleeve). The gastrointestinal implant device includes a distal portion and a proximal portion. The distal portion includes a gastrointestinal sleeve and the proximal portion of the device includes an anchor for securing the device within the gastrointestinal tract (e.g., in the proximal duodenum). In some embodiments, the container holds or houses the proximal portion of the gastrointestinal device. In other embodiments, the container holds or houses both the distal and proximal portions. In still further embodiments, the container holds or houses the entire gastrointestinal device. Some or all of the sleeve portion can be folded and stored in the container with the anchor.

After container 216 is at the desired location in the proximal duodenum, a distal portion 222 of the sleeve is removed from the container and directed into a location in the gastrointestinal tract that is distal from the container, as illustrated in FIGS. 2H-2J. Outer catheter 218 defines an inner catheter lumen (not illustrated in FIGS. 2H-2J) and an inner catheter (not illustrated in FIGS. 2H-2J), to which ball 220 is releasably attached, is directed through the inner catheter lumen and into locations of the gastrointestinal tract that are distal from container 216 and pylorus 206.

Distal portion 222 of the sleeve is releasably secured to the leading or distal portion of the inner catheter so that as the inner catheter is advanced through the distal intestine, distal portion 222 is also advanced. In this manner, distal portion 222 is directed to locations in the gastrointestinal tract that are distal from container 216 and into the distal intestines (e.g., into the jejunum).

As the inner catheter is advanced through the inner catheter lumen and into the distal intestine, the proximal portion (not illustrated in FIGS. 2H-2J) of outer catheter 218 is held in place to ensure that capsule 216 remains in the duodenum and does not move proximally into the stomach. The proximal portion 226 of the gastrointestinal sleeve (not illustrated in FIGS. 2H-2J) is releasably secured or attached to container 216 by a locking means (e.g., by an anchor locking wire) to ensure that the anchor does not emerge from container 216 and deploy before the distal portion 222 of the sleeve is extended to a desired location in the distal intestines.

The distal end of the inner catheter includes or is attached to an atraumatic tip (e.g., atraumatic ball 220), which minimizes or eliminates tissue trauma as the inner catheter is advanced into the distal intestines. The exact location to which distal portion 222 is advanced into the distal intestines will vary with the needs of the patient and the demands of the given procedure. The inner catheter also includes a stiffening wire that provides sufficient linear or column strength to the inner catheter to facilitate navigation of the distal intestines. Optionally, fluoroscopy is used to track the progress of the advancement.

After the desired length of sleeve has been delivered, endoscope 224 is optionally directed into the stomach to visually inspect the proximal end of delivery capsule 216 to ensure that it is in the desired position and/or to monitor the subsequent anchor deployment process, as illustrated in FIG. 2J. Optionally, the inner catheter includes markings which are useful for monitoring the advancement of the inner catheter. For example, the outer wall of the inner catheter can include a series of indicia which the practitioner can view as he slides portions of the inner catheter into and out of the outer catheter. In addition or alternatively, the inner catheter can include one or more radiopaque markings that can be viewed on an x-ray image or one or more markings that are visible via fluoroscopy.

After the distal portion of the sleeve is advanced to a desired location in the distal intestines, the anchor is deployed from the container and secured to a desired position within the gastrointestinal tract, as illustrated in FIGS. 2K-2L. The anchor locking means (not illustrated in FIGS. 2K-2L) is released to allow the anchor to be subsequently removed from container 216. For example, the anchor locking means can include a locking wire that releasably secures the anchor within container 216 and pulling the locking wire proximally detaches the anchor so that the anchor can be removed from the container at some subsequent time.

Container 216 includes visual marker 230 (e.g., a black ring) that can be used to determine if the capsule is in a desired location before anchor 228 is fully removed from container 216 and secured at a desired location in the gastrointestinal tract. For example, delivery catheter 218 is pulled proximally until visual marker 230 is proximal to pylorus 206 and visible in the stomach to endoscope 224. In this manner, the practitioner can ensure that the anchor will deploy at the desired anchoring position when it is removed from container 216.

Once container 216 is in the desired location, outer catheter 218 is held in position and the inner catheter is advanced further distally to pull the sleeve and anchor 228 from container 216. Optionally, the anchor is pushed out of the container using a means for displacing an anchor from the container assembly (e.g., an anchor plunger).

As shown in FIGS. 2K-2L, anchor 228 is removed from container 216 and deployed, thereby securing the proximal portion of the device in the gastrointestinal tract (e.g., at the duodenal bulb). For example, anchor 228 can secure the device with the use of barbs which extend into the muscle tissue of the proximal duodenum.

After anchor 228 is deployed and the device secured within the gastrointestinal tract, endoscope 224 is optionally removed and/or the stiffening wire is pulled proximally through a main stiffening wire lumen defined by inner catheter 229 and removed from the gastrointestinal tract. After the stiffening wire has been removed, the sleeve is optionally expanded or inflated by directing fluid 232 through the main stiffening wire lumen defined by inner catheter 229, as illustrated in FIG. 2M. The fluid causes a distal portion 222 of sleeve to expand and separate or disengage the distal portion of inner catheter 229, as illustrated in FIG. 2M. Suitable fluids include those discussed previously for use in expanding the duodenum. For example, the sleeve can be inflated by directing at least 180 milliliters of a saline solution or a dilute RENOGRAFIN™/saline solution. Atraumatic ball 220 and distal portion 222 are released from the inner catheter by pulling the locking wire (not illustrated in FIG. 2M) proximally until a release mark on the wire is visible at the proximal end of outer catheter 218.

Inner catheter 229 and outer catheter 218 are removed, as illustrated in FIG. 2N. Optionally, the position of the device can be monitored with fluoroscopy while inner catheter 229 and outer catheter 218 are removed from the gastrointestinal tract. Atraumatic ball 220 is moved distally via natural peristalsis and is excreted from the gastrointestinal tract.

Optionally, the endoscope is positioned across the pylorus and a fluid (e.g., a gas or liquid, such as air, nitrogen, carbon dioxide, saline, or dilute RENOGRAFIN™) is directed into the duodenum to confirm patency of the sleeve. FIG. 2N illustrates gastrointestinal device 234 placed in the gastrointestinal tract and the removal of the endoscope.

Figure 3A:
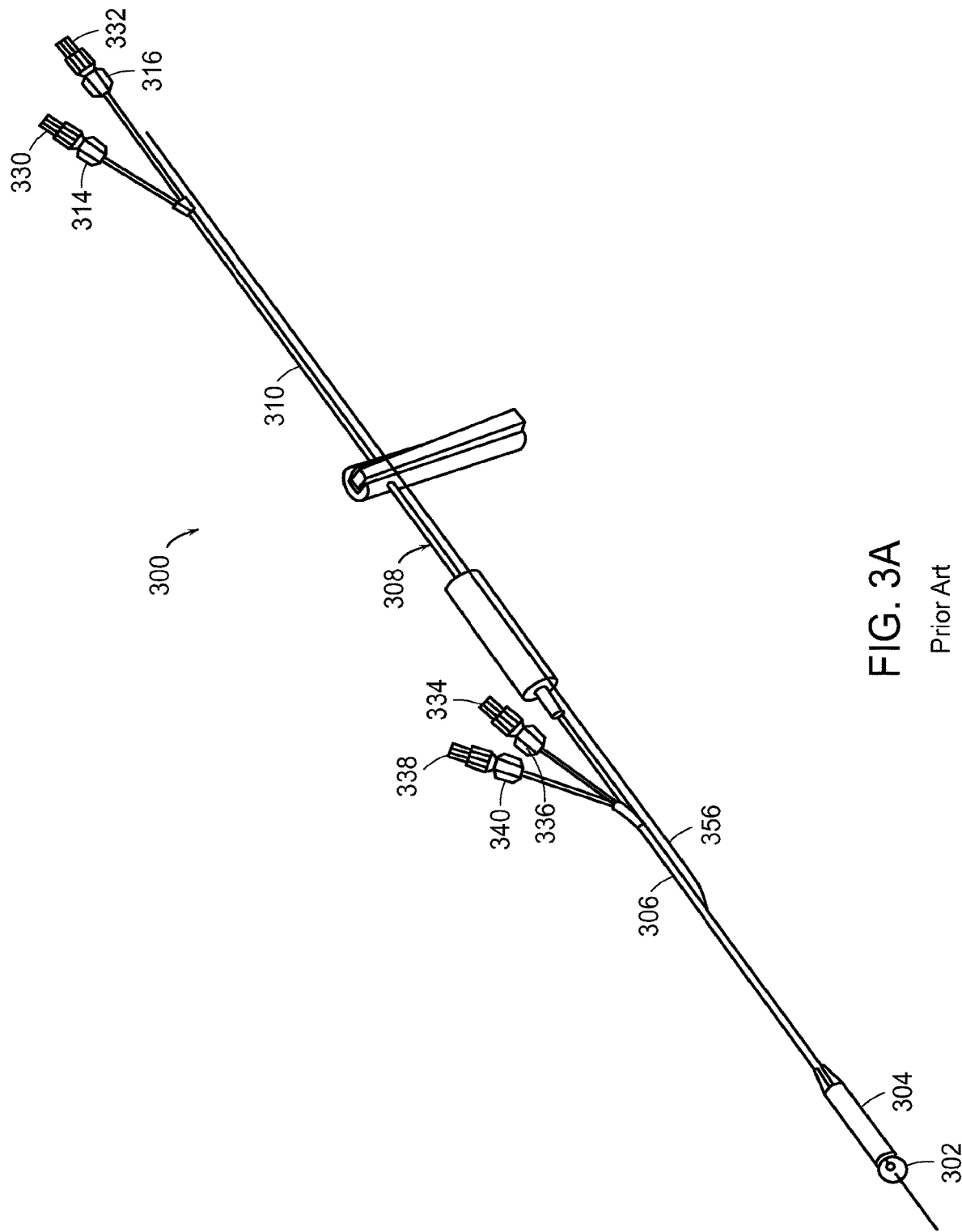
FIGS. 3A-3H illustrate a schematic view of assembled delivery catheter systems for delivery of gastrointestinal implant devices (e.g., gastrointestinal sleeves).

In some embodiments of the invention, the gastrointestinal implant devices are implanted via catheter-based placements methods (e.g., within endoluminal catheter). FIGS. 3A-3H illustrates multiple embodiments of this invention that include schematic views of various aspects of assembled delivery catheter system 300 for delivery of a gastrointestinal implant device (e.g., a gastrointestinal sleeve). As shown in FIG. 3A, delivery catheter system 300 includes an atraumatic tip comprising atraumatic ball 302, a container assembly that includes capsule or container 304, outer catheter 306, inner catheter pusher 308, and inner catheter 310.

Inner and outer catheters 310, 306 and container 304 are made from materials commonly used to form catheters. For example, inner catheter 310 can be made of a polyether block amide (e.g., PEBAX® 7233, available from Arkema Group, Paris, France). In some embodiments, outer catheter 306 is made of high density polyethylene and/or container 304 is made of hard plastic (e.g., acetal or polycarbonate). Preferably, catheters 310, 306 are made from materials having frictional properties that facilitate the movement of catheter 310 relative to catheter 306 and facilitate the movement of inner catheter 310 and container 304 in the gastrointestinal tract.

Figure 3B:
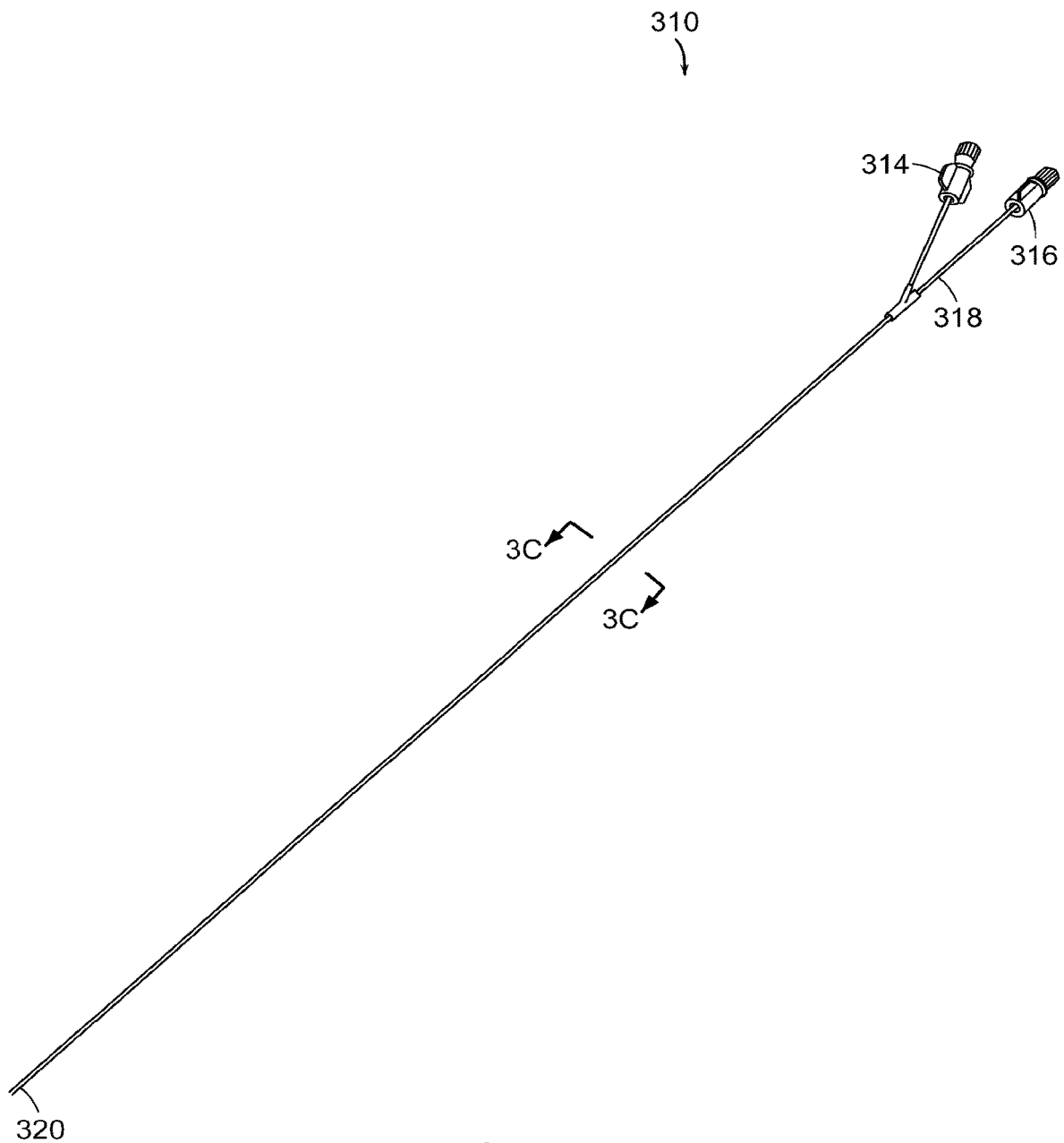
Figure 3C:
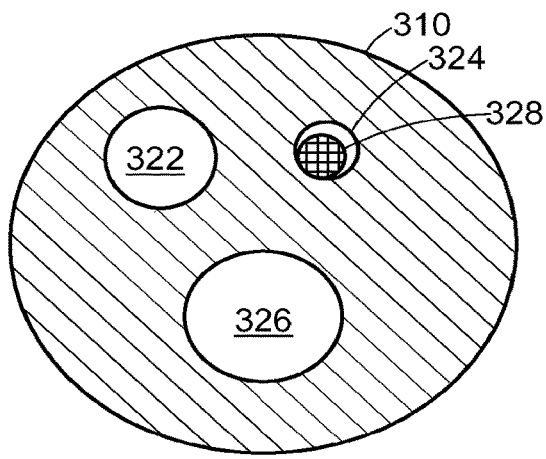

FIG. 3B illustrates a schematic diagram of inner catheter 310. Inner catheter 310 includes atraumatic ball locking wire port 314 and stiffening wire port 316 at proximal end 318. FIG. 3C illustrates a cross-sectional view of FIG. 3B through one section of inner catheter 310 that is between proximal end 318 and distal end 320. Inner catheter 310 defines ball locking wire lumen 322, tension wire lumen 324, and stiffening wire lumen 326. Locking wire lumen 322 and stiffening wire lumen 326 extend along the length of, and within, inner catheter 310. Locking wire lumen 322 extends from ball locking wire port 314 to distal end 320. Stiffening wire lumen 326 extends along the length of, and within, inner catheter 310, from stiffening wire port 316 to distal end 320. Tension wire 328 is located within tension wire lumen 324. The distal and proximal ends of tension wire 328 are attached to the inner walls of tension wire lumen 324, thereby securing tension wire 328 within inner catheter 310. For example, tension wire 328 can be attached to the inner walls of tension wire lumen 324 with adhesives, heat setting, or via coextruding inner catheter 310 and tension wire 328. Tension wire 328 provides structural support to inner catheter 310. For examples, tension wire 328 can prevent catheter 310 from undergoing undesired stretching or elongating.

Turning back to FIG. 3A, system 300 includes ball locking wire knob 330 and stiffening wire knob 332. Ball locking wire knob 330 extends from ball locking wire port 314 to distal end 302 via ball locking wire lumen 322 (illustrated in FIG. 3C) defined by inner catheter 310. Stiffening wire knob 332 extends from stiffening wire port 316 to distal end 302 via stiffening wire lumen 326 (illustrated in FIG. 3C) defined by inner catheter 310.

Figure 3E:
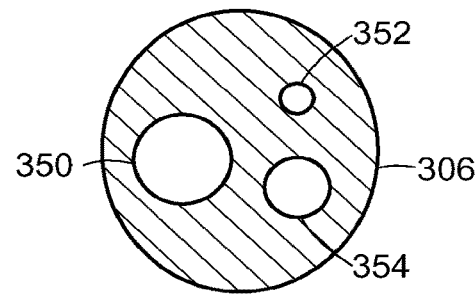
Figure 3H:
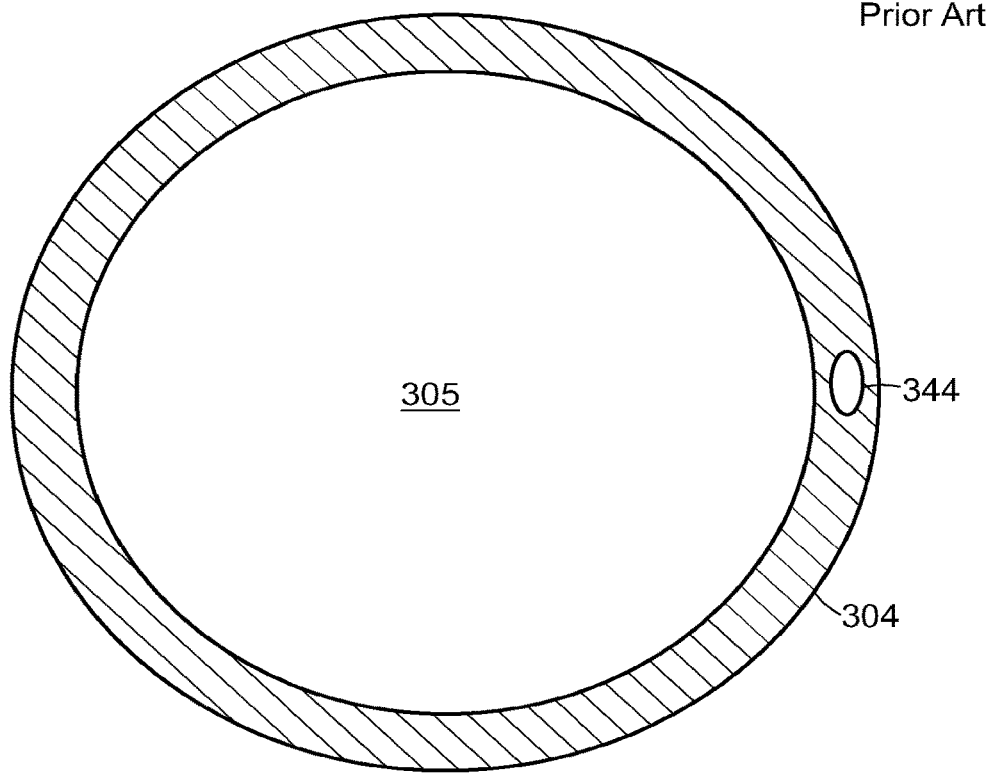
Figure 3D:
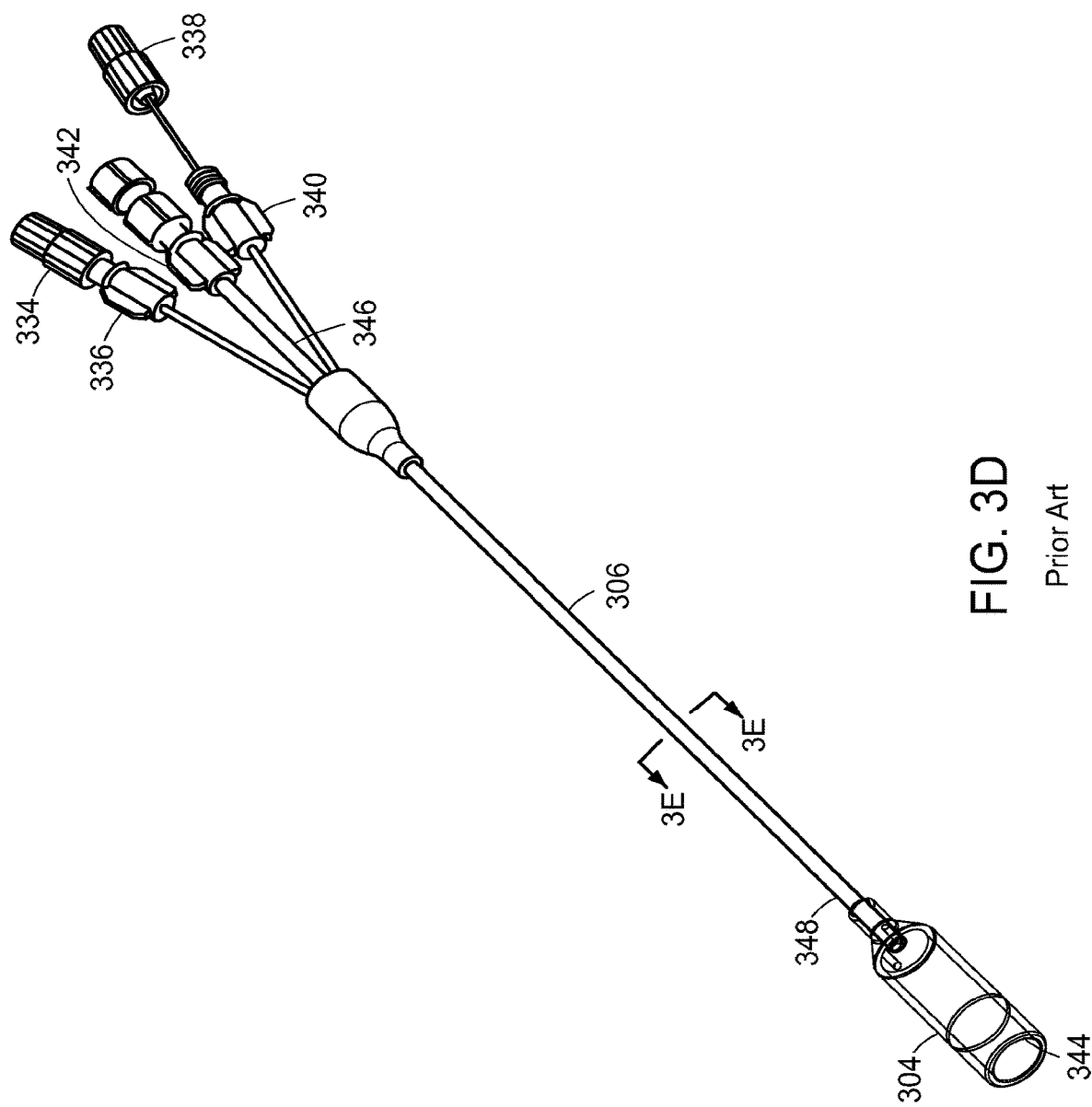

FIG. 3D illustrates a schematic diagram of outer catheter 306 and container 304. Container 304 defines guidewire lumen 344. Guidewire 356 (illustrated in FIG. 3A) extends along inner and outer catheters 310, 306 and through container 304 via guidewire lumen 344.

Outer catheter 306 includes anchor locking wire port 336, anchor plunger port 340, and attachment port 342 at proximal end 346. FIG. 3E illustrates a cross-sectional view of FIG. 3D through one section of outer catheter 306 that is between proximal end 346 and distal end 348. Outer catheter 306 defines inner catheter lumen 350, anchor locking wire lumen 352, and anchor plunger lumen 354. Anchor locking wire lumen 352 extends along, and within, outer catheter 306, from anchor locking wire port 336 to distal end 348. Anchor plunger lumen 354 extends along, and within, outer catheter 306, from anchor plunger port 340 to distal end 348.

Turning back to FIG. 3A, system 300 includes anchor locking wire 334, a means for displacing an anchor from the container assembly that includes anchor plunger 338, and guidewire 356. Anchor locking wire 334 extends from anchor locking wire port 336 to container 304 via anchor locking wire lumen 352 (illustrated in FIG. 3E) defined by outer catheter 306. Anchor plunger 338 extends from anchor plunger port 340 to container 304 via anchor plunger lumen 354 (illustrated in FIG. 3E) defined by outer catheter 306.

Figure 3F:
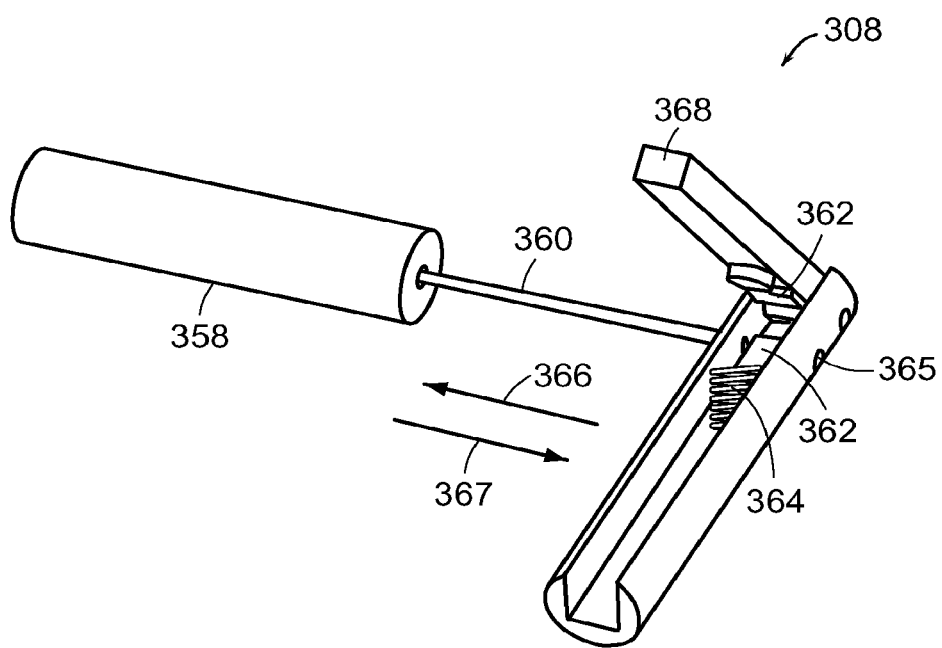

System 300 includes inner catheter pusher 308. Inner catheter pusher 308 is assembled or attached to outer catheter 306. FIG. 3F illustrates a schematic view of inner catheter pusher 308. Pusher 308 includes pusher handle 358, slide tube 360, and locking handle 368. Pusher handle 358 assembles or attaches pusher 308 to outer catheter 306 (as illustrated in FIG. 3A), thereby connecting pusher 308 to outer catheter 306. Pusher 308 defines inner catheter orifice 365, and a slide tube lumen that extends through handle 358, slide tube 360, and locking handle 368. Locking handle 368 is attached to slide tube 360 and includes inner catheter locking pads 362 and handle return spring 364. When assembled in system 300, inner catheter 310 extends through slide tube 360 and handle 368 via orifice 365 and the slide tube lumen.

In operation, depressing locking handle 368 causes locking pads 362 to securely grip a portion of inner catheter 310 relative to handle 368 and slide tube 360. Applying force in direction 366 while handle 368 is depressed moves handle 368, tube 360, and inner catheter 310 relative to handle 358, thereby directing a length of inner catheter 310 into the inner catheter lumen defined by the outer catheter. After pressure is released from handle 368, handle return spring 364 causes locking pads 362 to disengage from inner catheter 310. Once disengaged from inner catheter 310, handle 368 is moved along direction 367, and the process can then be repeated. In this manner, inner catheter 310 can be advanced distally through inner catheter lumen 350 defined by outer catheter 306. Slide tube 360 provides rigid support to inner catheter 310 to prevent inner catheter 310 from kinking during advancement.

Figure 3G:
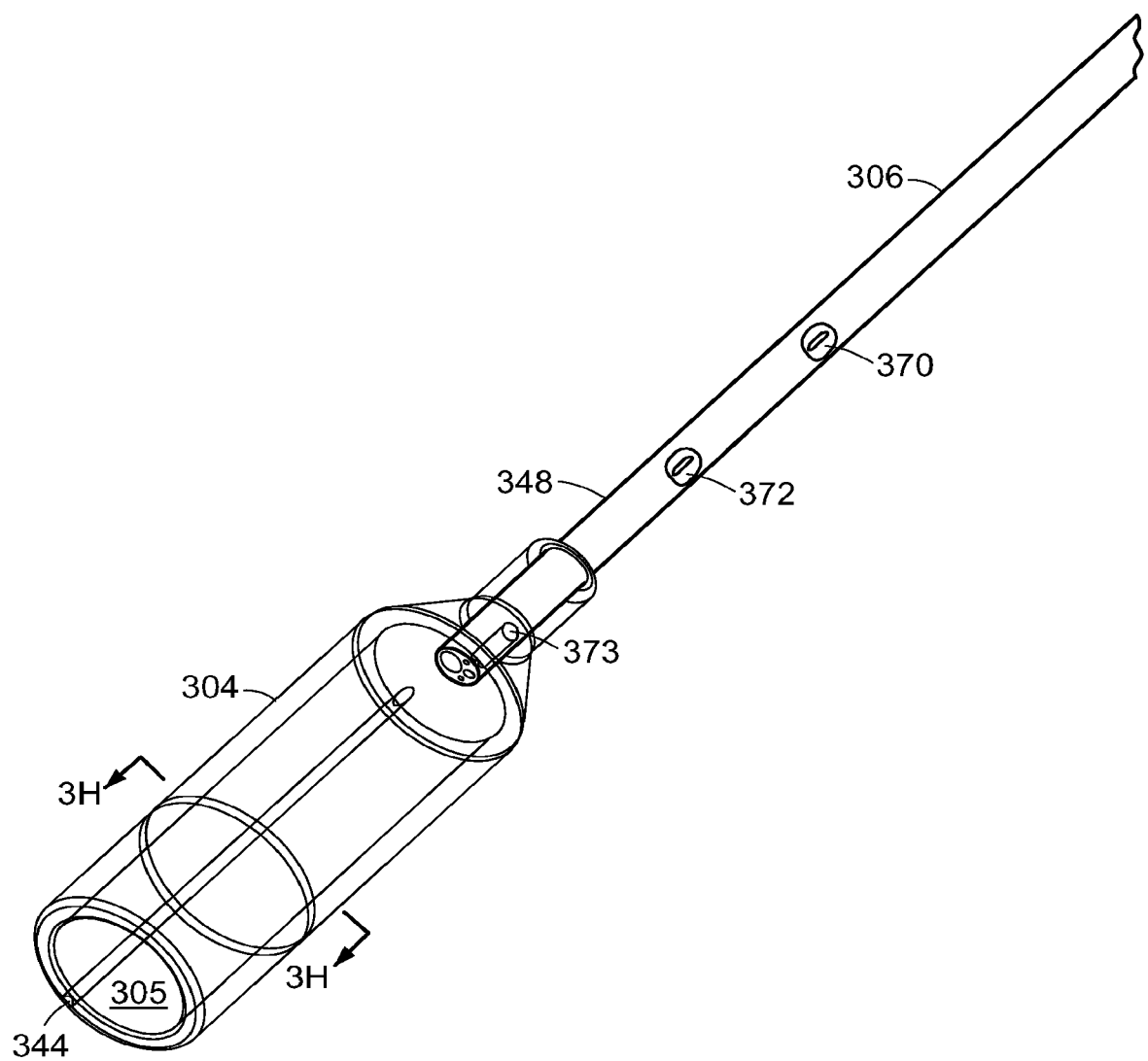

FIG. 3G illustrates a schematic diagram of a portion of system 300 that includes outer catheter 306 and container 304. Container 304 defines guidewire lumen 344 and is assembled or attached to distal end 348 of outer catheter 306. Container 304 also defines anchor locking wire port 373. Catheter 306 defines anchor locking wire ports 370 and 372 which intersect with anchor locking wire lumen 350 (not illustrated in FIG. 3G for clarity) defines by outer catheter 306. Optionally, interior walls of container 304 are lined with metal (e.g., with a steel liner). FIG. 3H illustrates a cross-sectional view of FIG. 3G through one section of container 304. Container 304 defines guidewire lumen 344 as well as inner chamber 305.

FIGS. 4A-4L illustrate additional embodiments of the present invention that include gastrointestinal implant delivery catheter system 400 and a method of use. For purposes of clarity, FIGS. 4A-4L do not illustrate the various parts and portions of a mammalian gastrointestinal tract.

System 400 includes an atraumatic tip comprising atraumatic ball 402, a container assembly that includes capsule or container 404, outer catheter 406, inner catheter pusher 408, inner catheter 410, and guidewire 412.

In some embodiments of this invention, system 400 is used to place or install a gastrointestinal implant device (e.g., a gastrointestinal sleeve) into the digestive tract of a mammal. Briefly, a gastrointestinal sleeve is releasably secured to the distal end of inner catheter 410 with a locking wire and then the sleeve and an anchor portion is placed or stored within container 404 of a container assembly. Guidewire 412 is directed into a desired location within a gastrointestinal tract of a mammal (e.g., in a proximal portion of the small intestine). After guidewire 412 is in the desired location, container 404 is directed along the guidewire into a desired location within the mammal's gastrointestinal tract (e.g., the duodenum). The distal end of inner catheter 410, along with the secured portion of the gastrointestinal sleeve, is advanced within the gastrointestinal tract to a location that is distal from container 404, thereby extending or unfurling at least a portion of the gastrointestinal sleeve. During some or all of the unfurling portion of the procedure, the anchor and the proximal portion of the sleeve is releasably secured within the container assembly with a locking wire. Once the sleeve has been extended to the desired extent (e.g., into the jejunum), the anchor portion is unlocked from the container assembly and removed from the container. The anchor can be removed from container 404 by, for example, again advancing inner catheter 410 and the releasably secured distal end of the sleeve, thereby pulling the unlocked anchor from container 404. Optionally, the anchor is removed from container 404 with the use of a means for displacing an anchor from the container assembly that includes anchor plunger 411. The anchor is secured at desired location within the gastrointestinal tract of the mammal (e.g., in the duodenum). Any portion of the gastrointestinal implant device that is still secured to system 400 is detached, and the system is removed from the mammal.

Figure 4A:
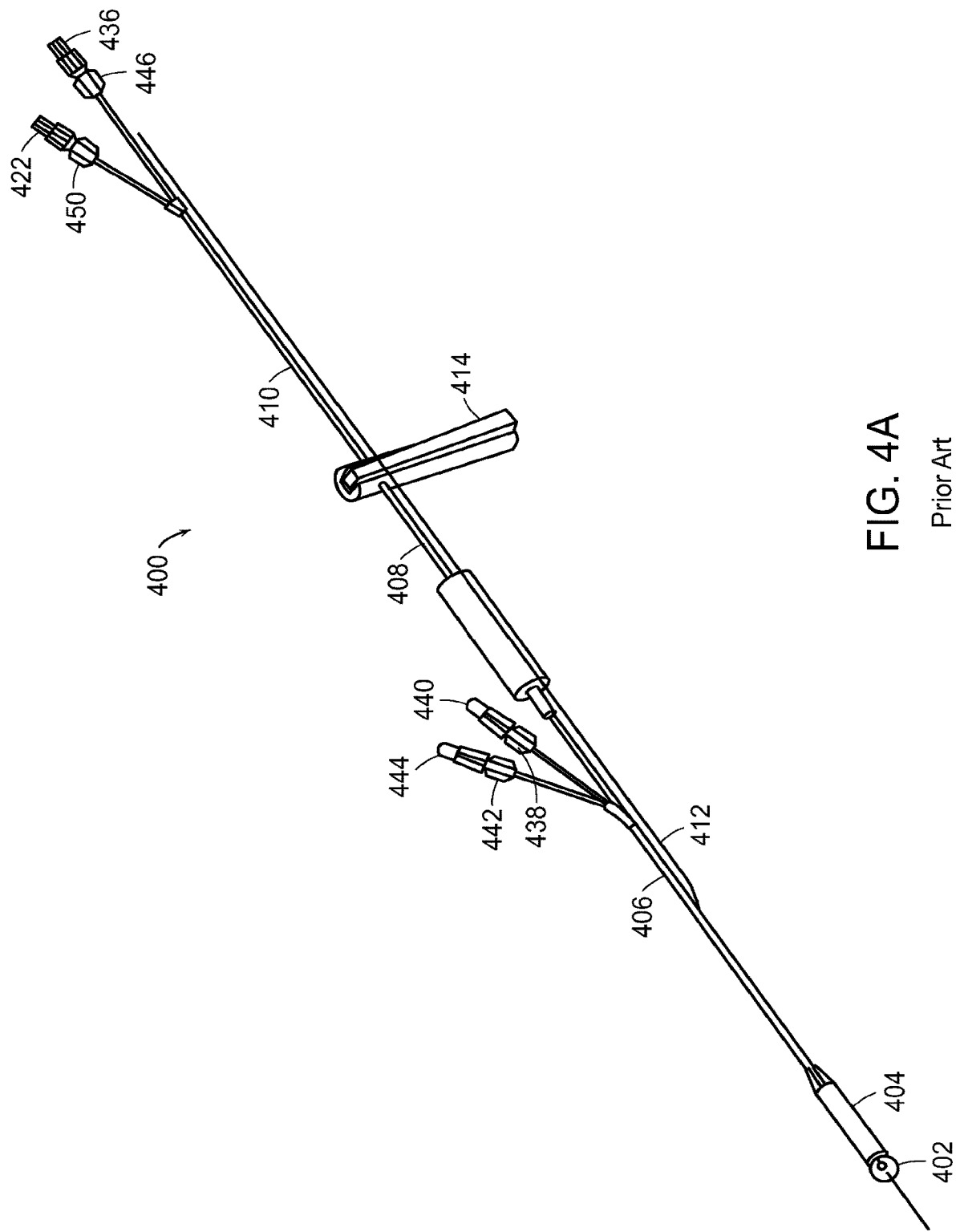

FIG. 4A illustrates system 400 with a gastrointestinal sleeve (not visible in FIG. 4A) stored within a container assembly that includes container 404. The sleeve includes a distal portion and a proximal portion. The proximal portion of the sleeve includes an anchoring device for securing the sleeve to a location within the gastrointestinal tract of a mammal. The anchor is placed or stored within a chamber defined by container 404. Some or all of the sleeve is folded and stored within the chamber as well. The distal portion of the sleeve is releasable secured to the distal end of inner catheter 410, and the anchor is releasably secured to container 404.

After the distal end of guidewire 412 is directed to a desired location within the gastrointestinal tract of a mammal, the proximal end of guidewire 412 is directed through a guidewire lumen defined by container 404. Once assembled to guidewire 412, outer catheter 406 is advanced to direct container 404 along guidewire 412 and to a desired location within the gastrointestinal tract of the mammal. After container 404 has been advanced to the desired location, guidewire 412 is removed from the gastrointestinal tract of the mammal. FIGS. 2E-2K illustrate advancement of a container along a guidewire and into the gastrointestinal tract of a mammal.

Figure 4B:
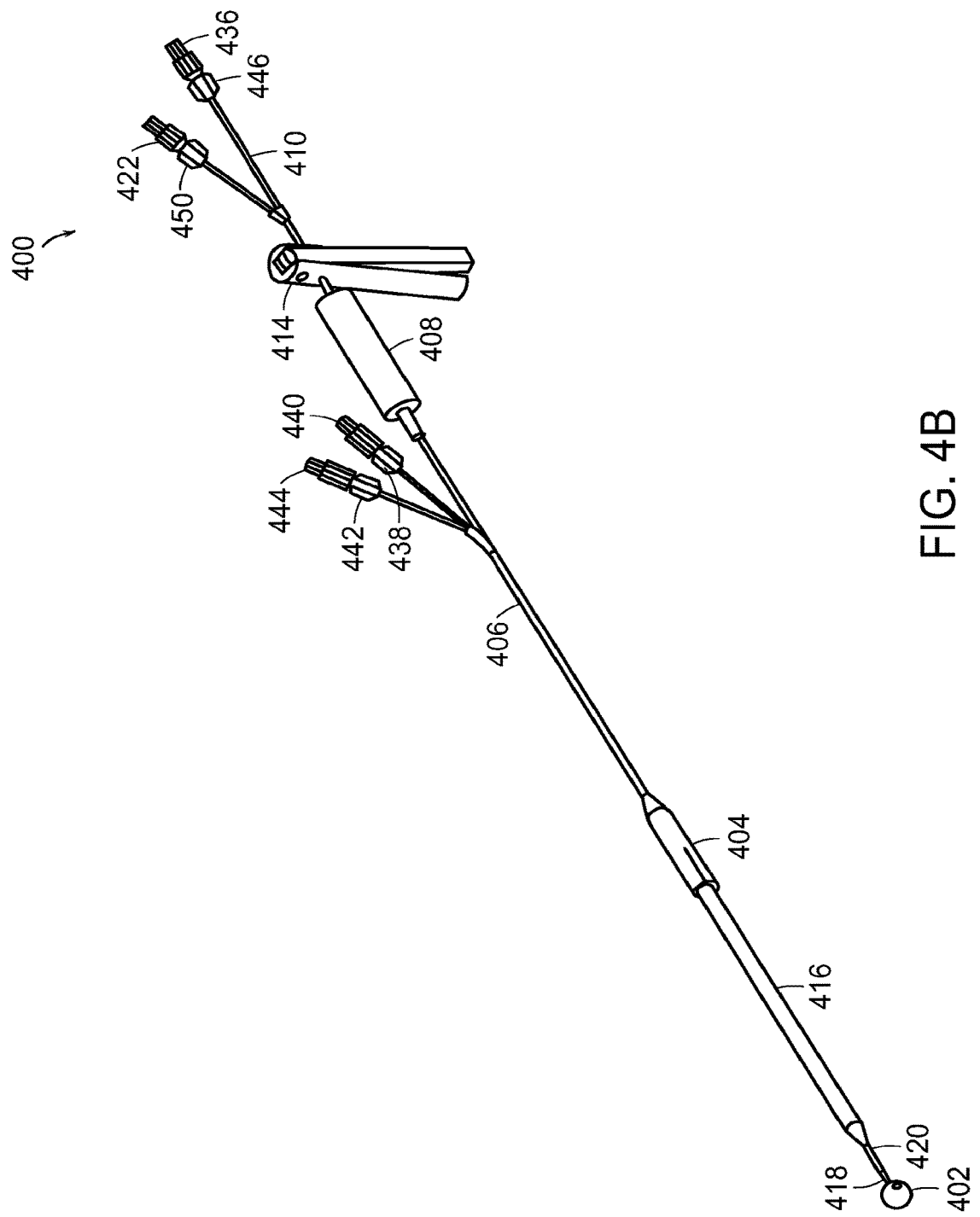

Inner catheter pusher 408 is used to direct a distal end of inner catheter 410 into a desired location in the gastrointestinal tract that is distal to container 404. Locking handle 414 is depressed, thereby causing the pads (not illustrated in FIG. 4A) of pusher 408 to securely grip inner catheter 410. Handle 414 is slid distally, thereby directing a length of inner catheter 410 into the inner catheter lumen (not illustrated in FIG. 4A) defined by outer catheter 406 and causing the distal end 418 of inner catheter 410 to emerge from the distal end of container 404, as shown in FIG. 4B. Distal portion 420 of sleeve 416 is attached to distal end 418 of inner catheter 410 and is advanced with the inner catheter (FIGS. 2H-2J illustrate advancement of an inner catheter and a distal portion of a sleeve). Locking handle 414 is released and the process repeated until a desired length of inner catheter 410 and intestinal sleeve 416 has been advanced. FIG. 4B illustrates system 400 after a length of sleeve 416 has been advanced.

Figure 5A:
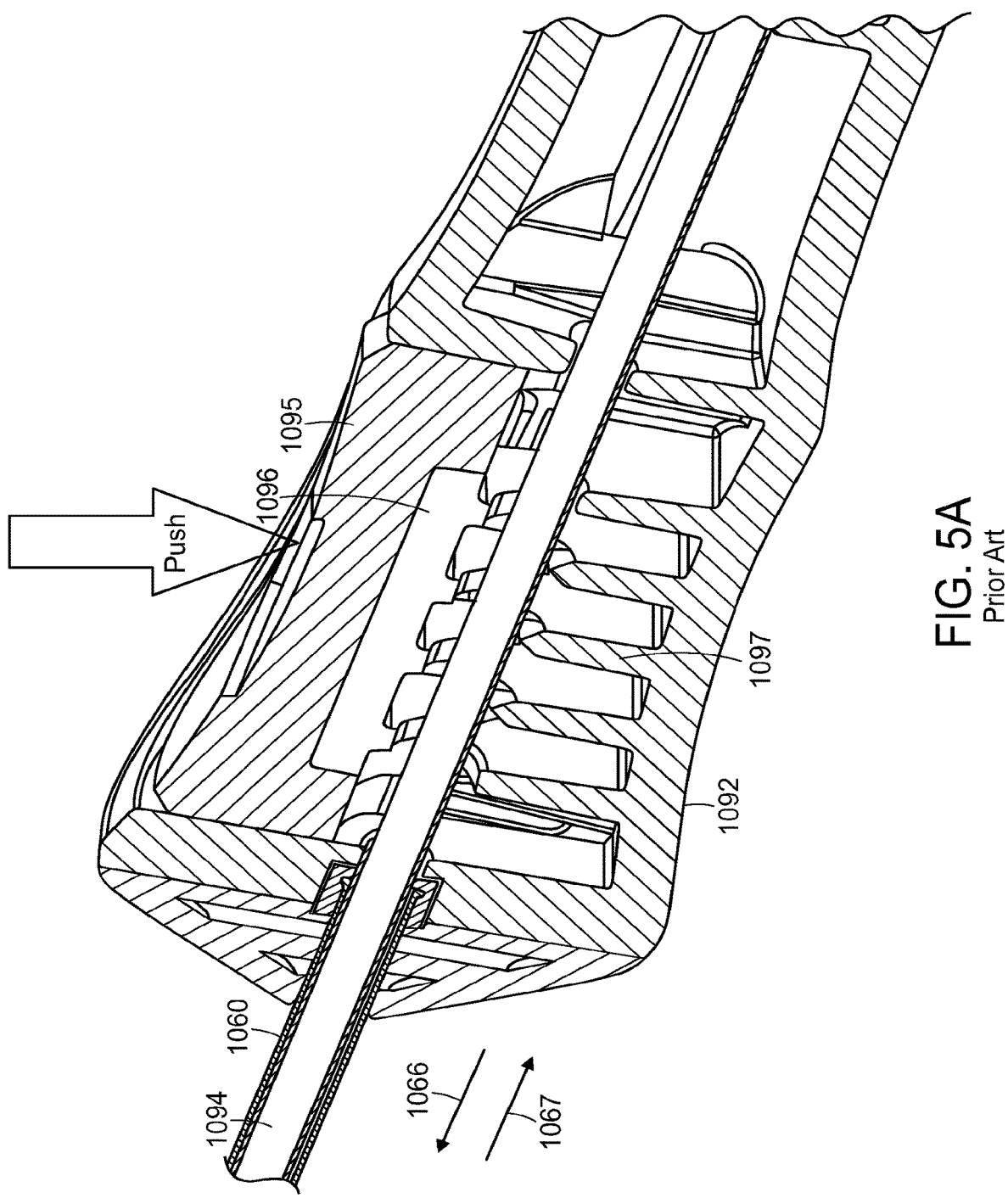
FIGS. 5A-5B illustrate cross-sectional views of a prior art catheter pusher handle.
Figure 5B:
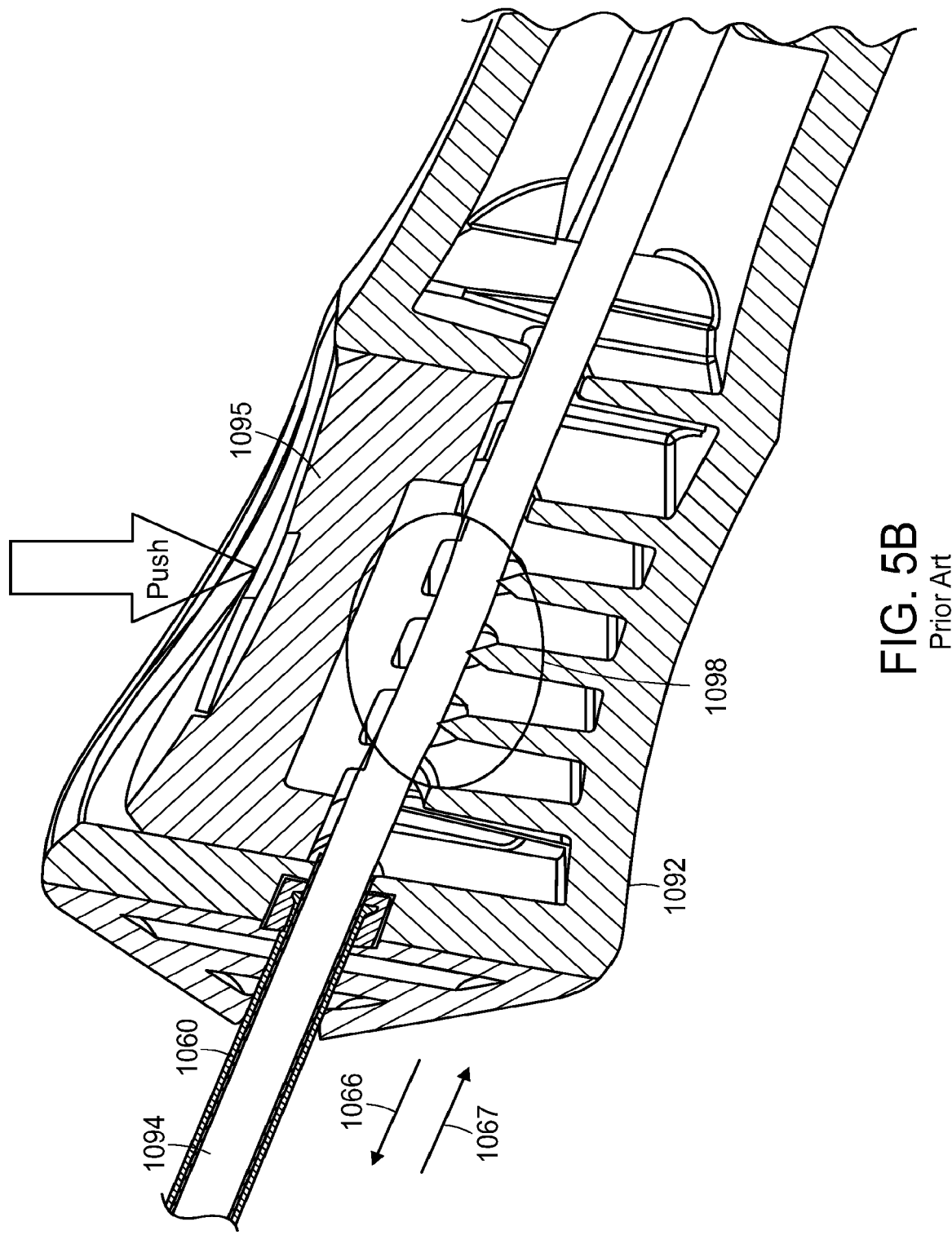

FIGS. 5A-5B illustrate a prior art catheter pusher handle for a delivery system of a gastrointestinal implant device. An inner catheter 1094 can be captured or retained by depressing a (silicone) button 1095 on catheter handle 1092. Depression of the button pushes on an insert 1096 (FIG. 5A). Acrylonitrile Butadiene Styrene (ABS), a styrene plastic, or other like material can be used for the insert 1096. Depression of the button 1095 on the insert 1096 pinches the inner catheter 1094 between the insert 1096 and the bottom 1097 of the handle 1092 (FIG. 5B).

Applying force in direction 1066 while button 1095 is depressed moves handle 1092, slide tube 1060, and inner catheter 1094, thereby directing a length of inner catheter 1094 along direction 1066, e.g., into an inner catheter lumen defined by an outer catheter. After pressure is released from button 1095, insert 1096 disengages from inner catheter 1094. Once disengaged from inner catheter 1094, handle 1092 is moved along direction 1067, and the process can then be repeated. In this manner, inner catheter 1094 can be advanced distally, e.g., through an inner catheter lumen defined by outer catheter, such as described, for example, with respect to FIGS. 3A and 4A-4B. Slide tube 1060 provides rigid support to inner catheter 1094 to prevent inner catheter 1094 from kinking during advancement.

However, a potential drawback of the embodiment of FIGS. 5A-5B is that, during less than ideal delivery conditions, the silicone button 1095 requires high mechanical force (e.g. by the user) to positively engage the inner catheter 1094 at one or more pinch points 1098. If positive button engagement is not achieved, the inner catheter 1094 does not advance and the ABS insert 1096 and handle bottom 1097 can cause marks (e.g., chatter marks) on the inner catheter. Chatter marks on the inner catheter may lead to other catheter malfunctions, such as, for example, increased friction and catheter buckling.

Figure 6A:
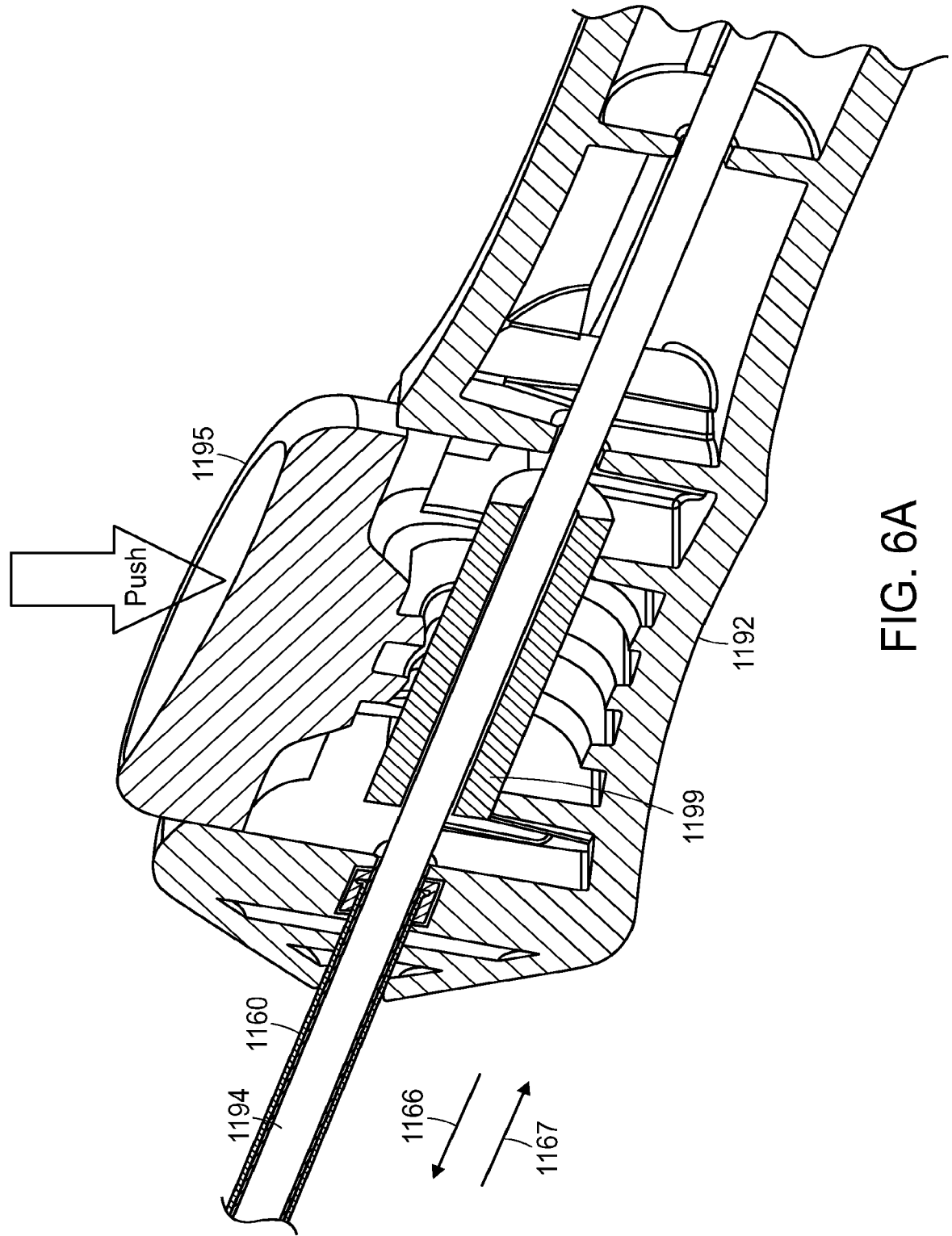
FIGS. 6A-6B illustrate cross-sectional views of an embodiment of a catheter pusher handle.
Figure 6B:
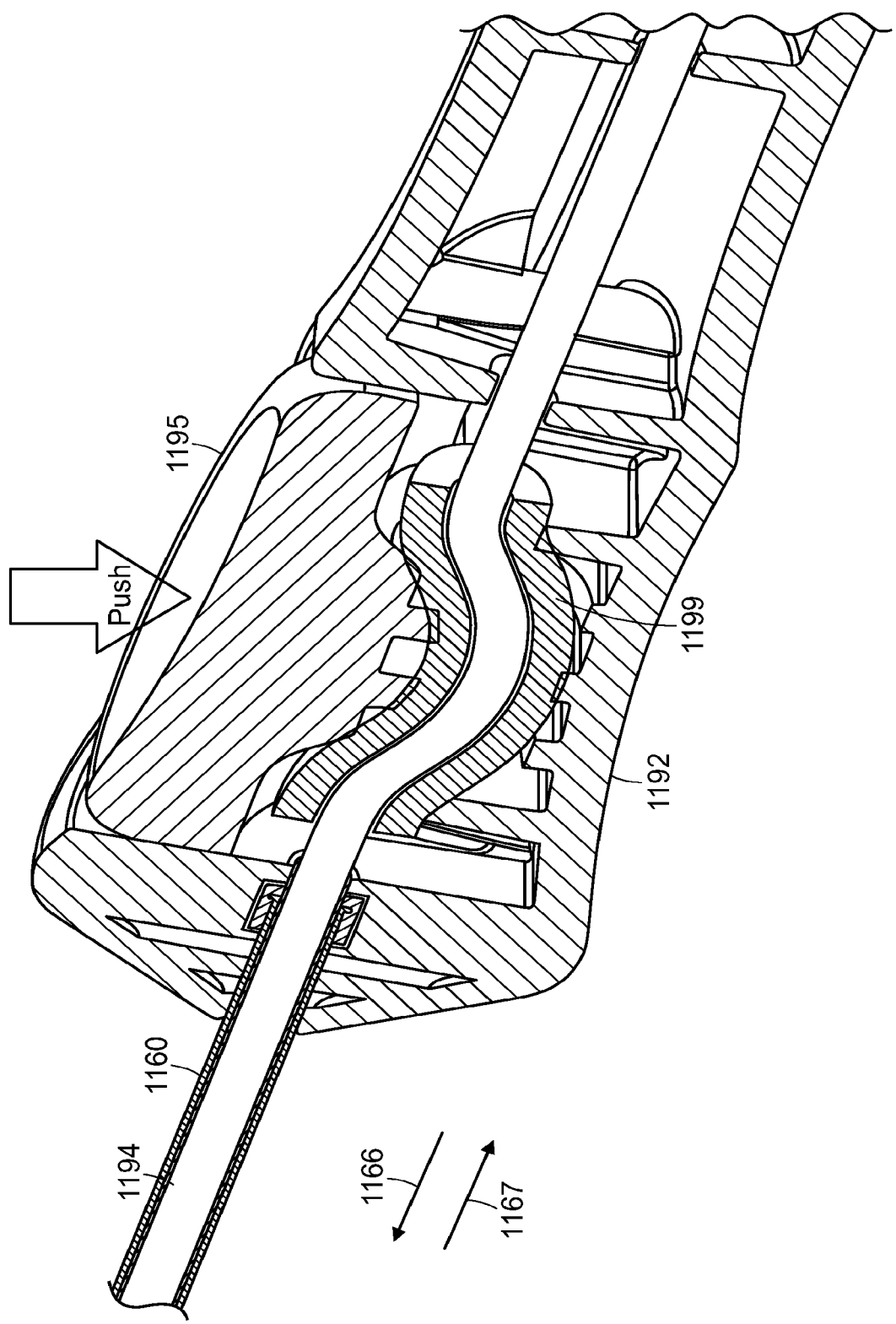

FIGS. 6A-6B illustrate an alternative embodiment of a catheter handle according to the invention. Inner catheter 1194 is movable within elongated handle 1192, which extends along a length of inner catheter 1194. The inner catheter 1194 can be captured (e.g., retained, engaged) by depressing a button 1195 (e.g., a button made of a hard thermoplastic, such as ABS) on handle 1192, illustrated in FIGS. 6A-6B. Depression of the button 1195 by a user can push and bend a tube 1199 (e.g., a silicone tube) (FIG. 6B). As shown, the tube 1199 is an elongated element that is housed within the catheter handle. The tube 1199 surrounds a portion of the inner catheter 1194 running through a center channel. Engagement of the tube 1199 with the inner catheter 1194 is achieved through friction and non-plastic deformation. The inner diameter of the tube 1199 can be approximately equal to or greater than the outer diameter of the inner catheter 1194. Such a configuration can allow for the inner catheter 1194 to freely move within the tube 1199 when the button 1195 is not depressed (e.g., to minimize resistance or friction). The inner catheter 1194 is deformed but not damaged when the button is depressed. Deformation caused to the tube 1199 and inner catheter 1194 stays within the elastic limits of the tube and inner catheter. Once the ABS button 1195 is released, the external force exerted on the tube 1199 is removed, returning the tube 1199 and the inner catheter 1194 to nondeformed states.

Similar to the catheter pusher handles described above, applying force in direction 1166 while button 1195 is depressed moves handle 1192, slide tube 1160, and inner catheter 1194, thereby directing a length of inner catheter 1194 along direction 1166. After pressure is released from button 1195, tube 1199 and inner catheter 1194 return to nondeformed states, inner catheter 1194 and handle 1192 can be moved along direction 1167, and the process can then be repeated. Slide tube 1160 provides rigid support to inner catheter 1194 to prevent the catheter from kinking during advancement. In this manner, inner catheter 1194 can be advanced distally.

Figure 9C:
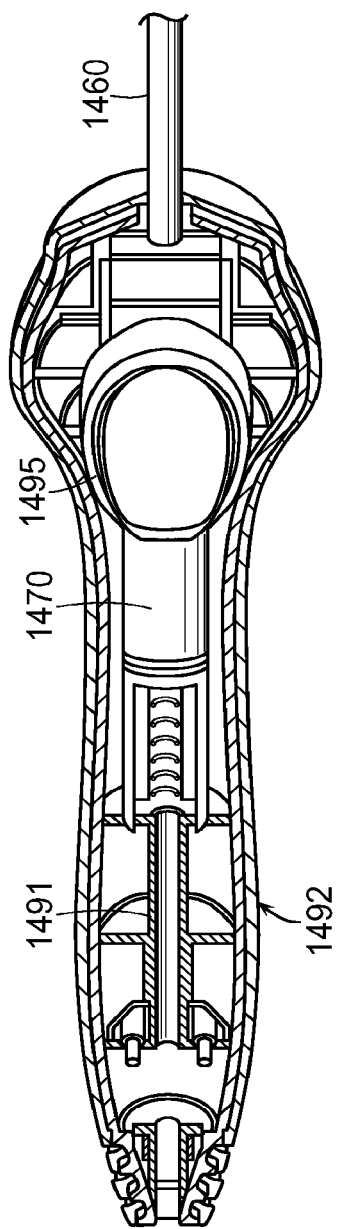
FIG. 9C is a top perspective view of the catheter pusher handle of FIGS. 9A-9B having a portion of the handle removed.
Figure 10A:
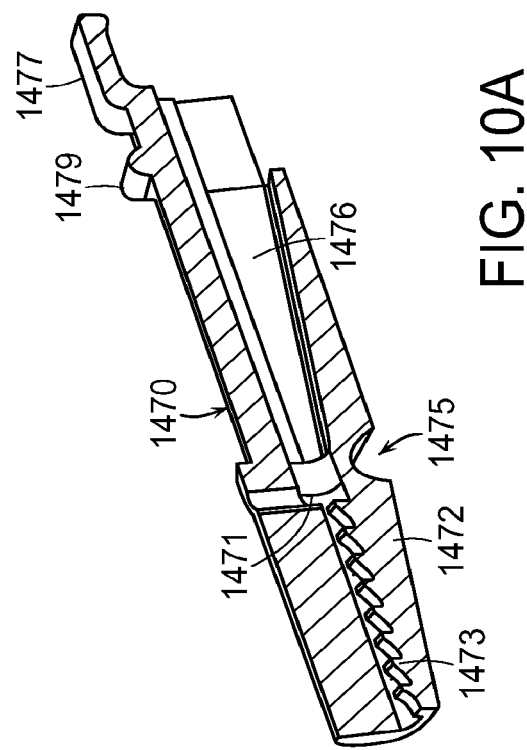
FIGS. 10A-10C are sectional views and FIG. 10D is a perspective view of a lever of the catheter handle of FIGS. 9A-9C.

FIGS. 9A-9C illustrate another embodiment of a catheter pusher handle. Catheter handle 1492 includes a lever 1470 including a lever jaw 1472 with directional teeth 1473. The lever 1470 is an elongated element housed within handle 1492. Inner catheter 1494 extends through and is movable within the handle and a lumen 1476 defined by the lever 1470 (see also FIG. 10A). Button 1495 includes a hinge 1496 that is seated in a groove of resilient element 1478. When button 1495 is depressed, it presses on lever 1470 and causes lever 1470 to rotate about a pivot 1474. This causes the lever jaw 1472 to engage a portion of the inner catheter 1494, thereby retaining or capturing the inner catheter 1494. Engagement of the inner catheter is achieved through directional teeth 1473. The teeth aid in retaining the inner catheter within the handle. A resilient element 1478, e.g., a spring, is configured to non-plastically deform when the button 1495 is depressed. Resilient element 1478 provides a restoring force to cause the lever jaw to disengage the inner catheter when the button is released. Note that in FIG. 9B, resilient element 1478 is shown in a non-deformed state for illustration purposes only. When button 1495 is depressed, the portion of resilient element 1478 near tab 1477 of lever 1470 is bent down below tab 1477.

Applying force in direction 1466 while button 1495 is depressed moves handle 1492, slide tube 1460, and inner catheter 1494, thereby directing a length of inner catheter 1494 along direction 1466, e.g., into an inner catheter lumen defined by an outer catheter (see, for example, FIGS. 3A, 4A-4B and 14 and associated description). After pressure is released from button 1495, lever jaw 1472 disengages from inner catheter 1494. Once the lever jaw is disengaged from inner catheter 1494, handle 1492 can be moved along direction 1467, and the process can then be repeated. In this manner, inner catheter 1494 can be advanced distally, along direction 1466. Slide tube 1460, which may be a metal tube, provides rigid support to inner catheter 1494 to prevent inner catheter 1494 from kinking during advancement. As shown, slide tube 1460 extends into handle 1492 but not into lumen 1476 (FIG. 10A) of lever 1470. Slide tube may extend into lever 1470 to a position just distal of resilient element 1478.

FIG. 9C is a top perspective view of handle 1492 with a top part of the handle removed. Also removed is inner catheter 1494. As shown, handle 1492 includes a longitudinal channel 1491 to guide the inner catheter.

FIGS. 10A-10D illustrate detailed views of the lever 1470. As shown, lever 1470 includes lumen 1476 for receiving the inner catheter (FIG. 9A) and a notch 1475 to seat pivot 1474. Lumen 1476 includes a circular passage 1471 near notch 1475. The diameter of passage 1471 can be equal to or greater than an outer diameter of the inner catheter (see also FIGS. 9A-9B). Lever jaw 1472 is positioned proximal from notch 1475. A tab 1477 extends distally from the body of the lever 1470. Tab 1477 cooperates with resilient element 1478 (FIG. 9A). Lever 1470 includes a boss 1479 that protrudes from a top surface of lever 1470, near tab 1477, and that is configured to cooperate with button 1495, as illustrated FIG. 9A. The lever 1470 can be configured to translate a force with which the button 1495 is depressed into a force with which the inner catheter is engaged at an amplification ratio (engagement force:depression force) in the range of about 1:1 to about 2:1. In one embodiment, the amplification ratio is about 2:1.

Figure 10B:
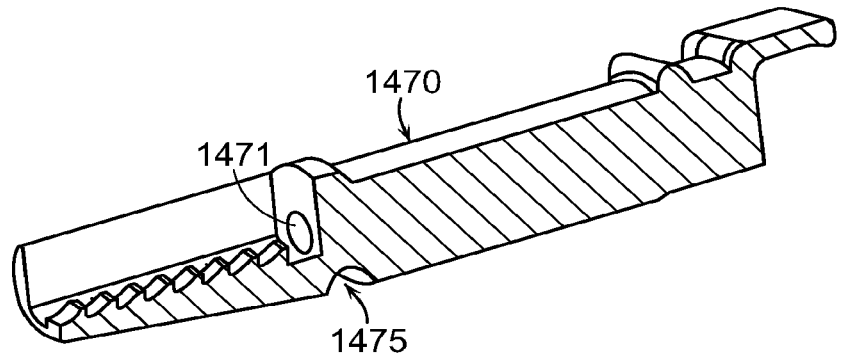
Figure 10C:
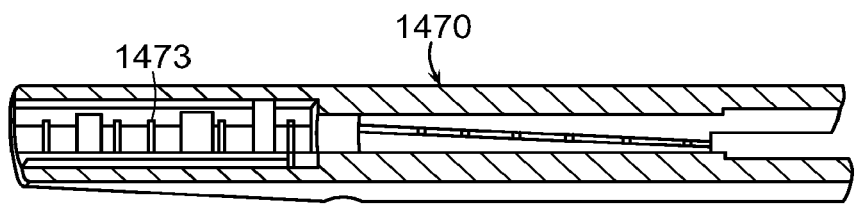
Figure 10D:
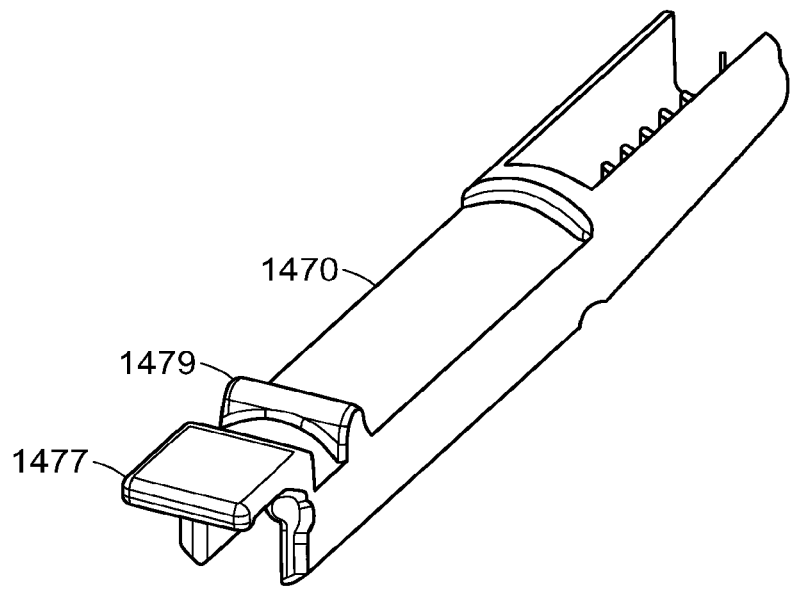

As illustrated in FIGS. 10B and 10C, directional teeth 1473 of lever 1470 can have a curved top surface to improve engagement with the outer surface of the inner catheter.

Figure 11A:
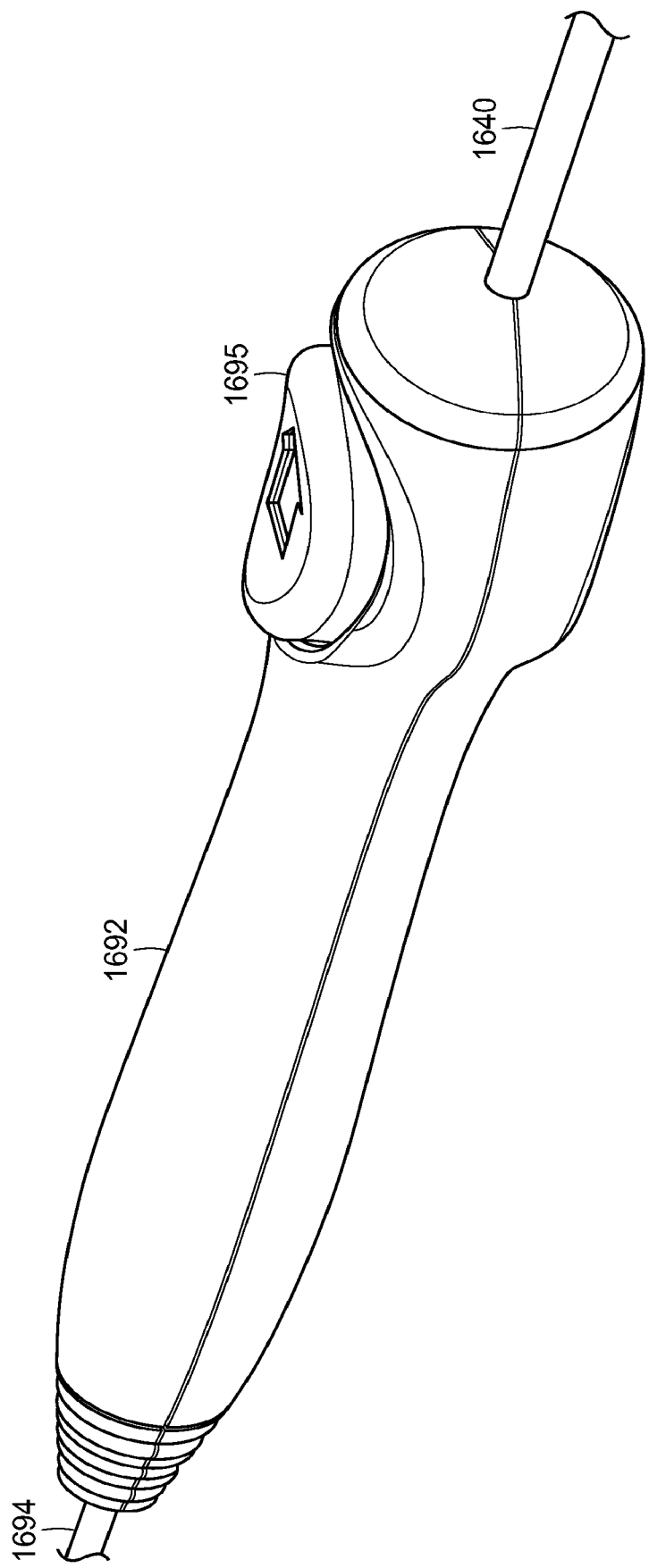
FIGS. 11A-11E illustrate yet another embodiment of a catheter pusher handle.
Figure 11B:
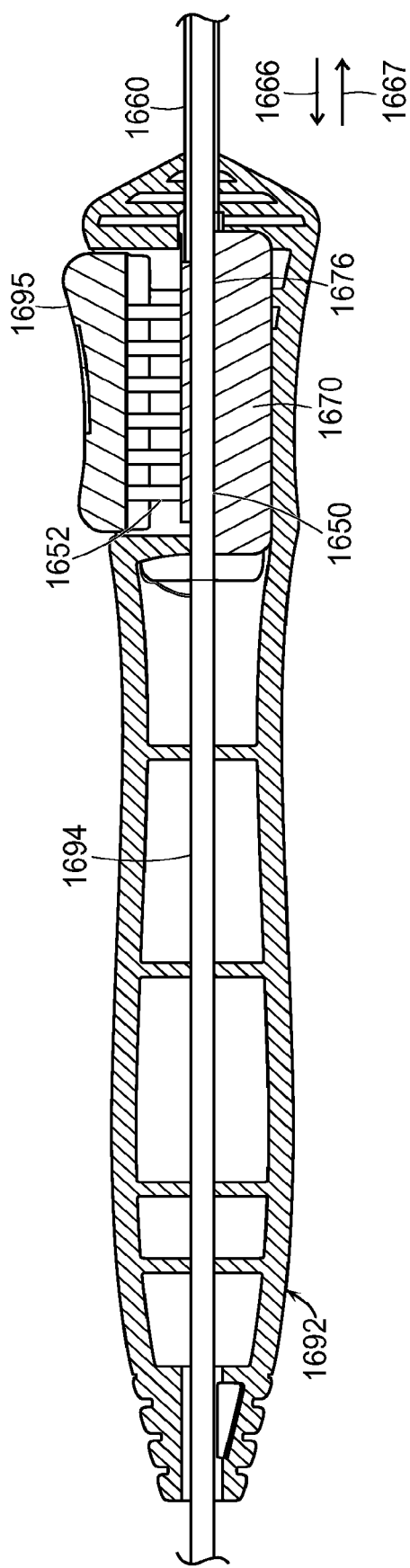
Figure 11C:
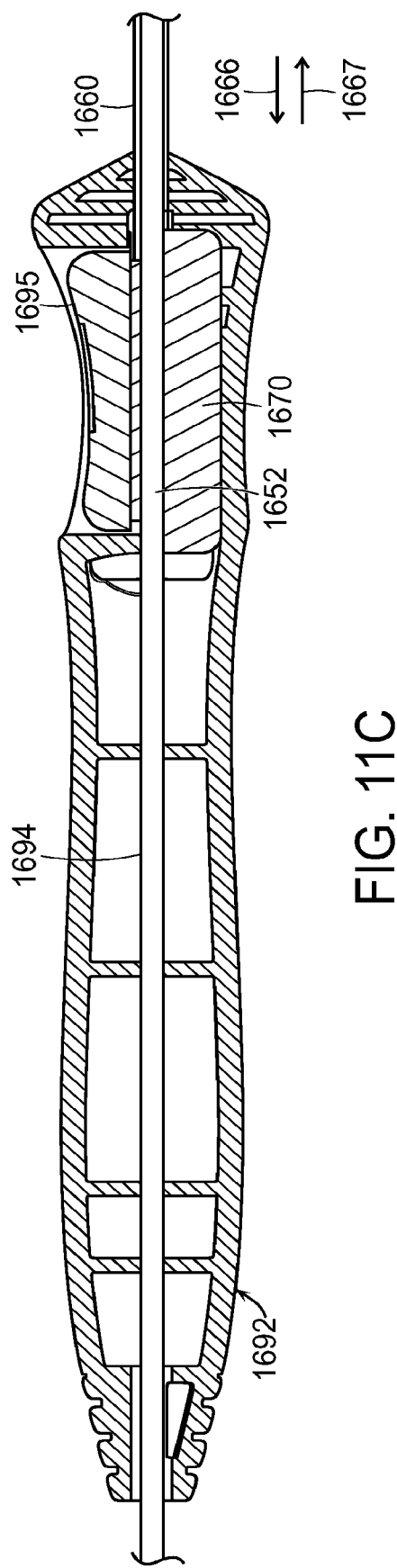

FIGS. 11A-11G illustrate yet another embodiment of a catheter pusher handle. As shown in FIG. 11A-11C, catheter handle 1692 includes a button 1695 on a side of the handle and an elongated element 1670 housed within handle 1692. Inner catheter 1694 extends through and is movable within the handle, lumen 1676 defined by the element 1670, and slide tube 1660. As shown, elongated element 1670 is an insert positioned within handle 1692 such that lumen 1676 is aligned with a major longitudinal axis of the handle. The elongated element 1670 includes ramped slots 1650 and the button 1695 includes ramped teeth 1652 aligned with the slots (see also FIGS. 11F and 11G). When the button 1695 is depressed (FIG. 11C), it causes the ramped teeth 1652 to engage the inner catheter 1694 via the slots 1650 and press the inner catheter against the element 1670, thereby retaining the inner catheter within the handle.

As illustrated in FIG. 11C, applying force in direction 1666 while button 1695 is depressed moves handle 1692, slide tube 1660, and inner catheter 1694, thereby directing a length of inner catheter 1694 along direction 1666, e.g., into an inner catheter lumen defined by an outer catheter (see, for example, FIGS. 3A, 4A-4B and FIG. 14 and associated description). After pressure is released from button 1695, ramped teeth 1652 disengage from inner catheter 1694 and handle 1692 can be moved along direction 1667. The process of capturing and advancing the inner catheter using handle 1692 can then be repeated. In this manner, inner catheter 1694 can be advanced distally, along direction 1666. Slide tube 1660, which may be a metal tube, provides rigid support to inner catheter 1694 to prevent inner catheter 1694 from kinking during advancement.

Figure 11D:
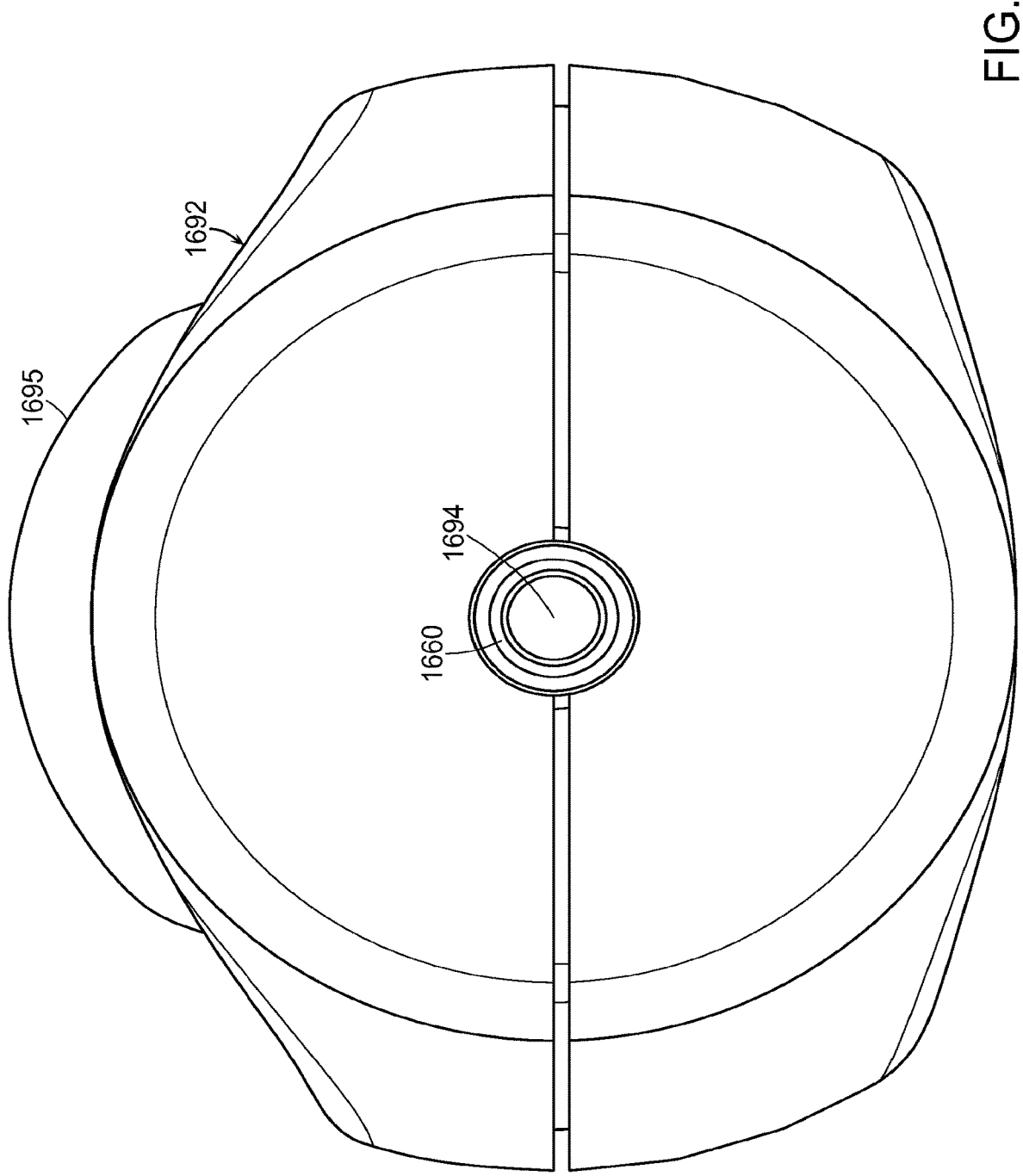
Figure 11E:
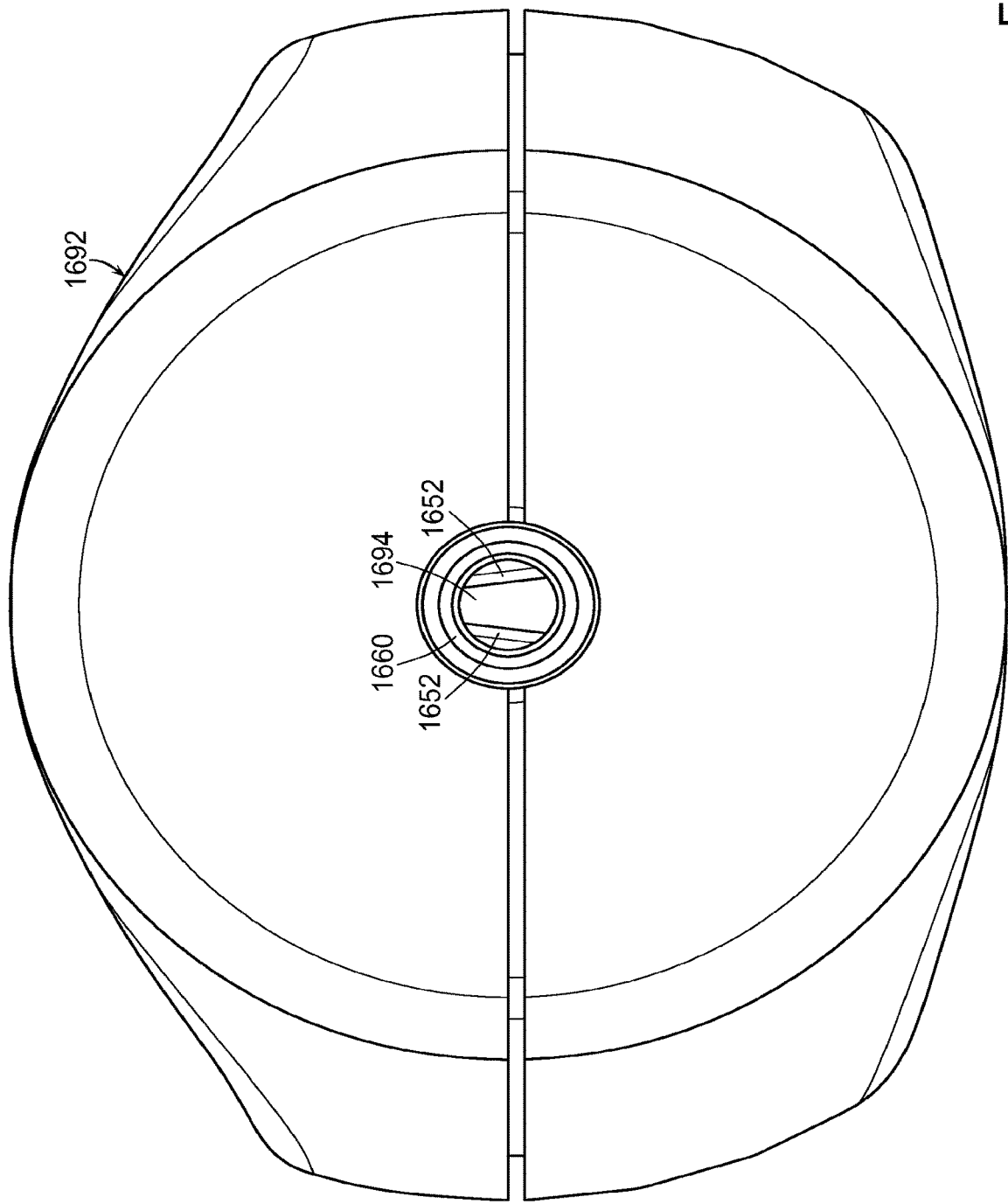

FIGS. 11D and 11E are frontal views of the catheter handle illustrated in FIGS. 11B and 11C, respectively. FIG. 11E illustrates engagement of the inner catheter 1694 by ramped teeth 1652, which are arranged in V-shaped manner and engage the inner catheter from opposite sides of the catheter.

Figure 11F:
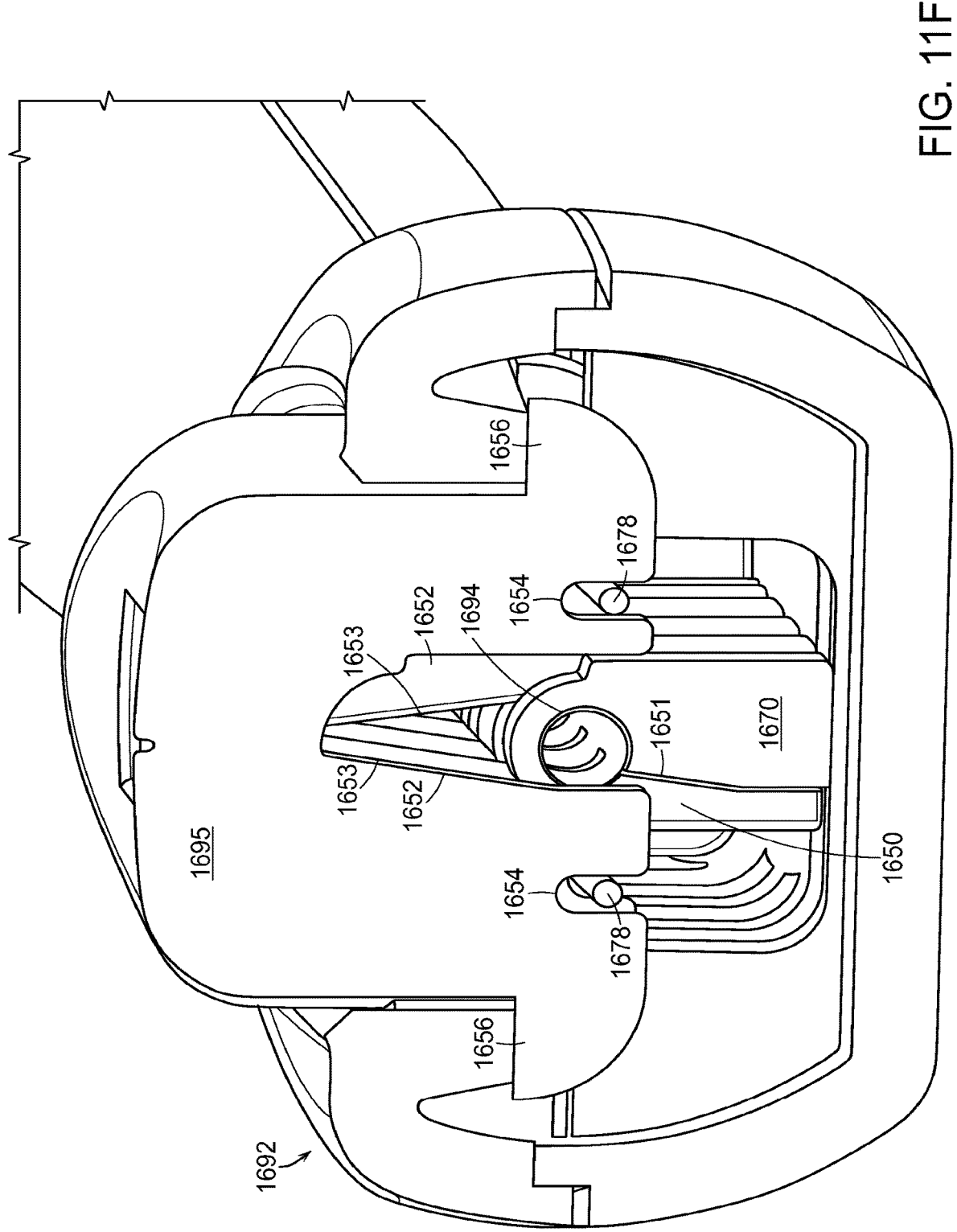
FIGS. 11F-11G illustrate sectional views of the catheter pusher handle of FIG. 11A.
Figure 11G:
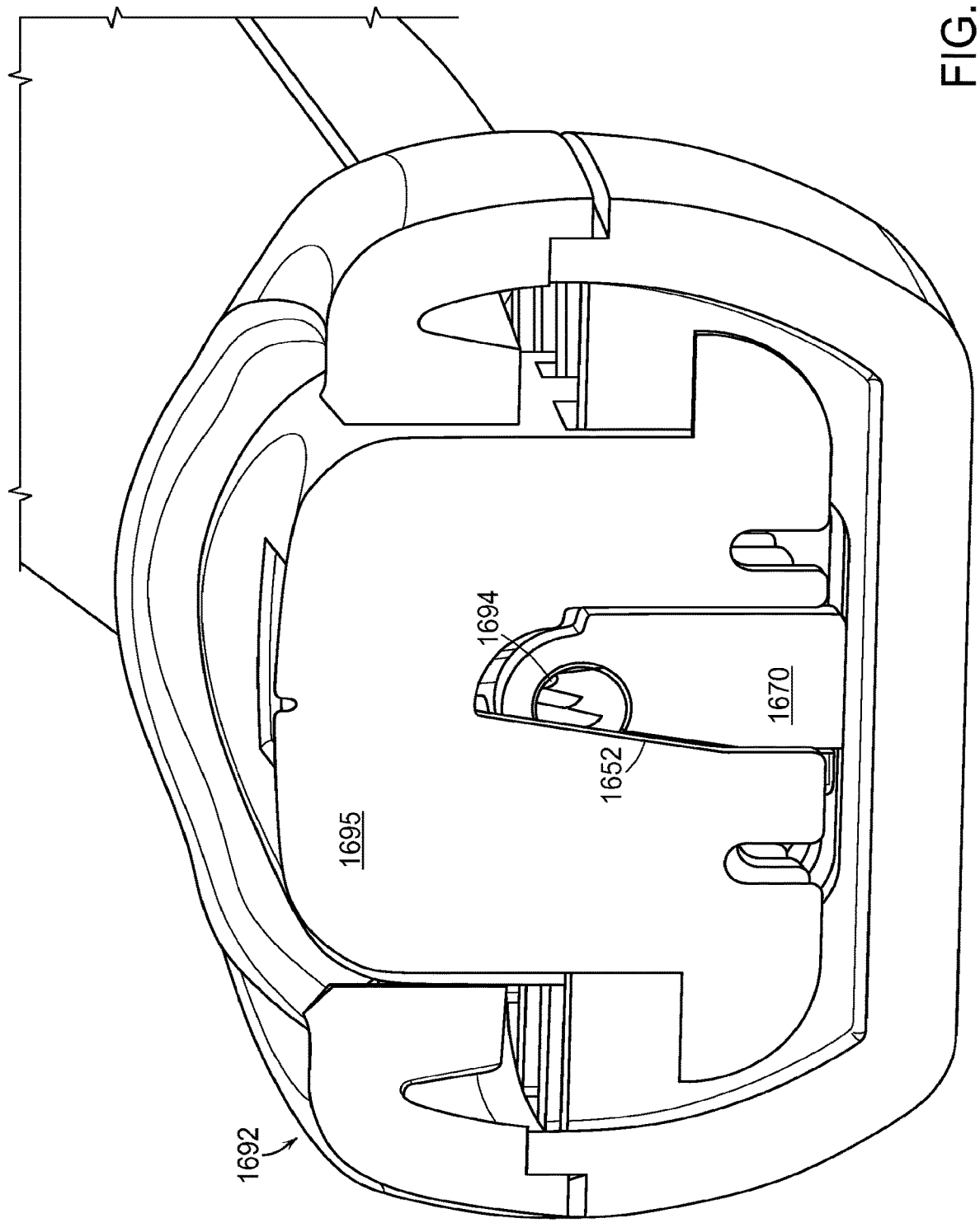

FIGS. 11F-11G illustrate sectional views of the catheter pusher handle of FIG. 11A. One or more resilient elements 1678, e.g., springs, wires and the like, are provided. The one or more resilient elements are configured to non-plastically deform when the button 1695 is depressed and to provide a restoring force to cause the ramped teeth 1652 of the button to disengage the inner catheter 1694 when the button is released. The button 1695 includes feet 1656 to prevent the button from falling out of the housing of the handle. The feet 1656 may also guide movement of the button relative to the housing when the button is depressed and provide a stop against the action of the resilient element when the button is released. Further, the teeth 1652 and slots 1650 may define multiple complementary features. For example, each of the teeth 1652 of button 1695 defines a ramped surface 1653 and each of the slots 1650 defines a ramped surface 1651 that is complementary to a ramped surface 1653.

Figure 11H:
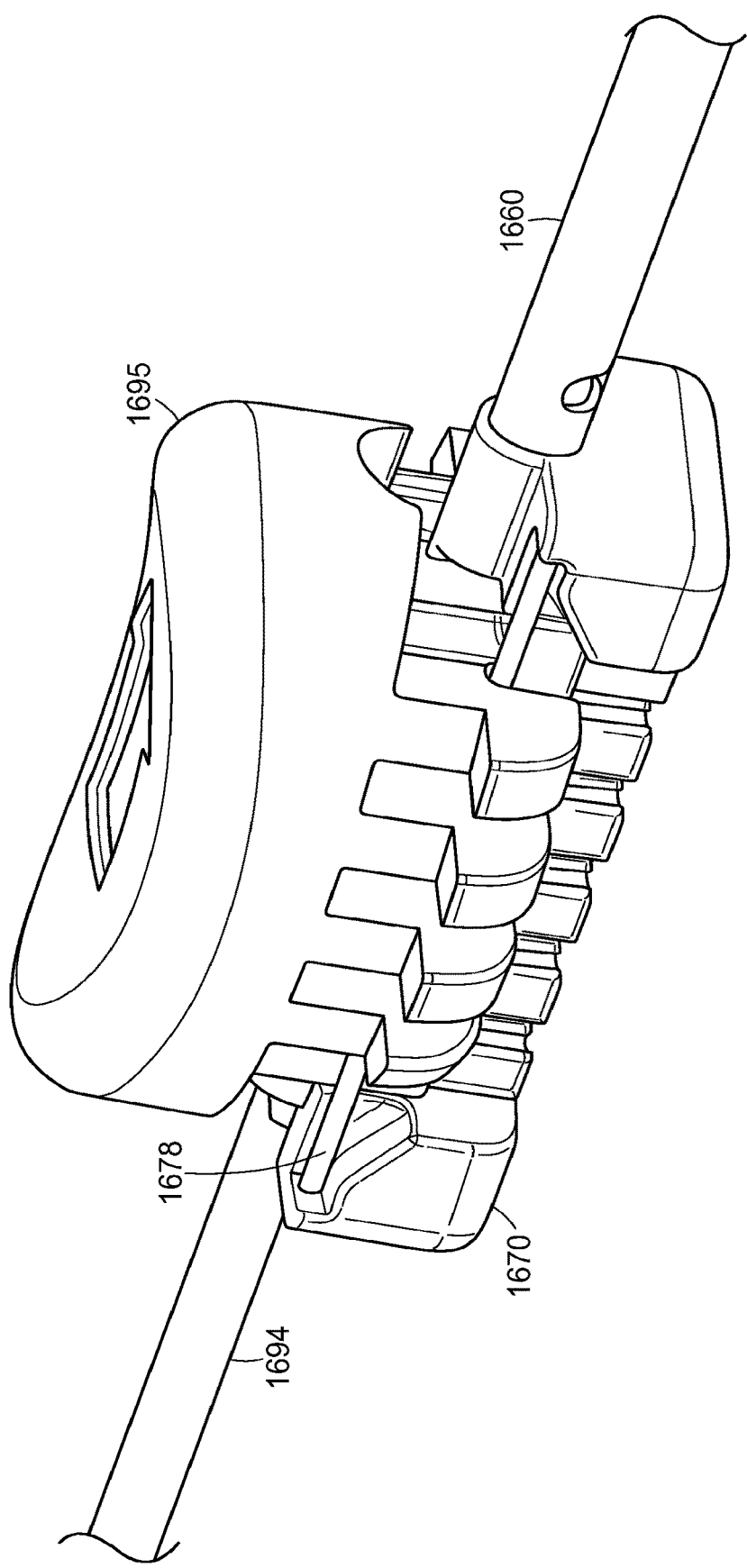
FIG. 11H illustrates a detail view of elements of the catheter pusher handle of FIG. 11A with the housing of the handle removed.

As further illustrated in the detail view of FIG. 11H, the resilient elements 1678 can be two rods placed between the button 1695 and elongated element 1670. The rods extend through channels 1654 in the button and are supported at respective ends by the elongated element. Depressing the button bends the rods between ends of the rods. When the button is released, the rods tend to return to their original configuration. This provides the restoring force that can cause the ramped teeth to disengage from the inner catheter.

Figure 12A:
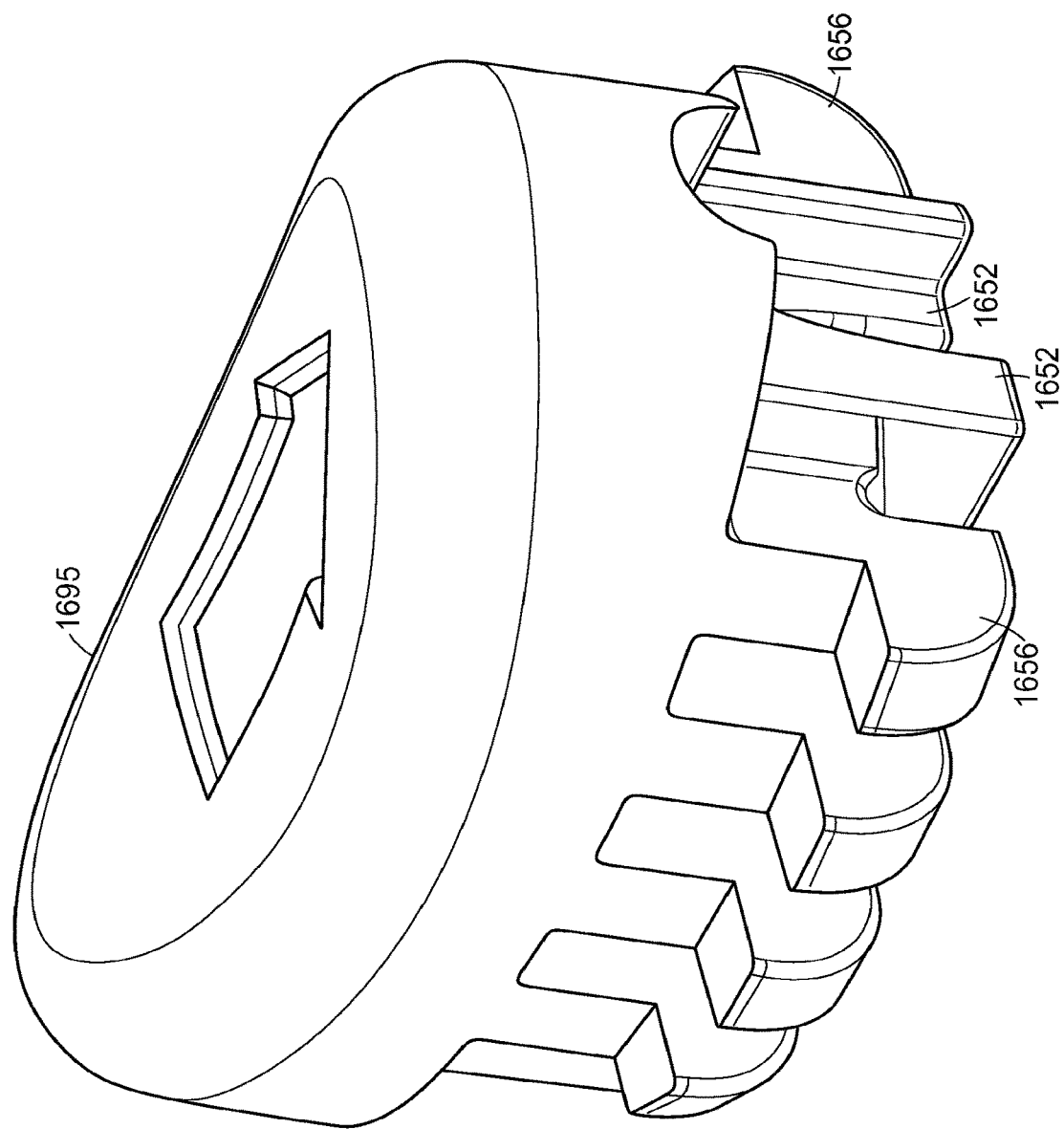
FIGS. 12A-12C are top perspective, bottom perspective, and frontal views, respectively, of the button of the catheter pusher handle of FIG. 11A.
Figure 12B:
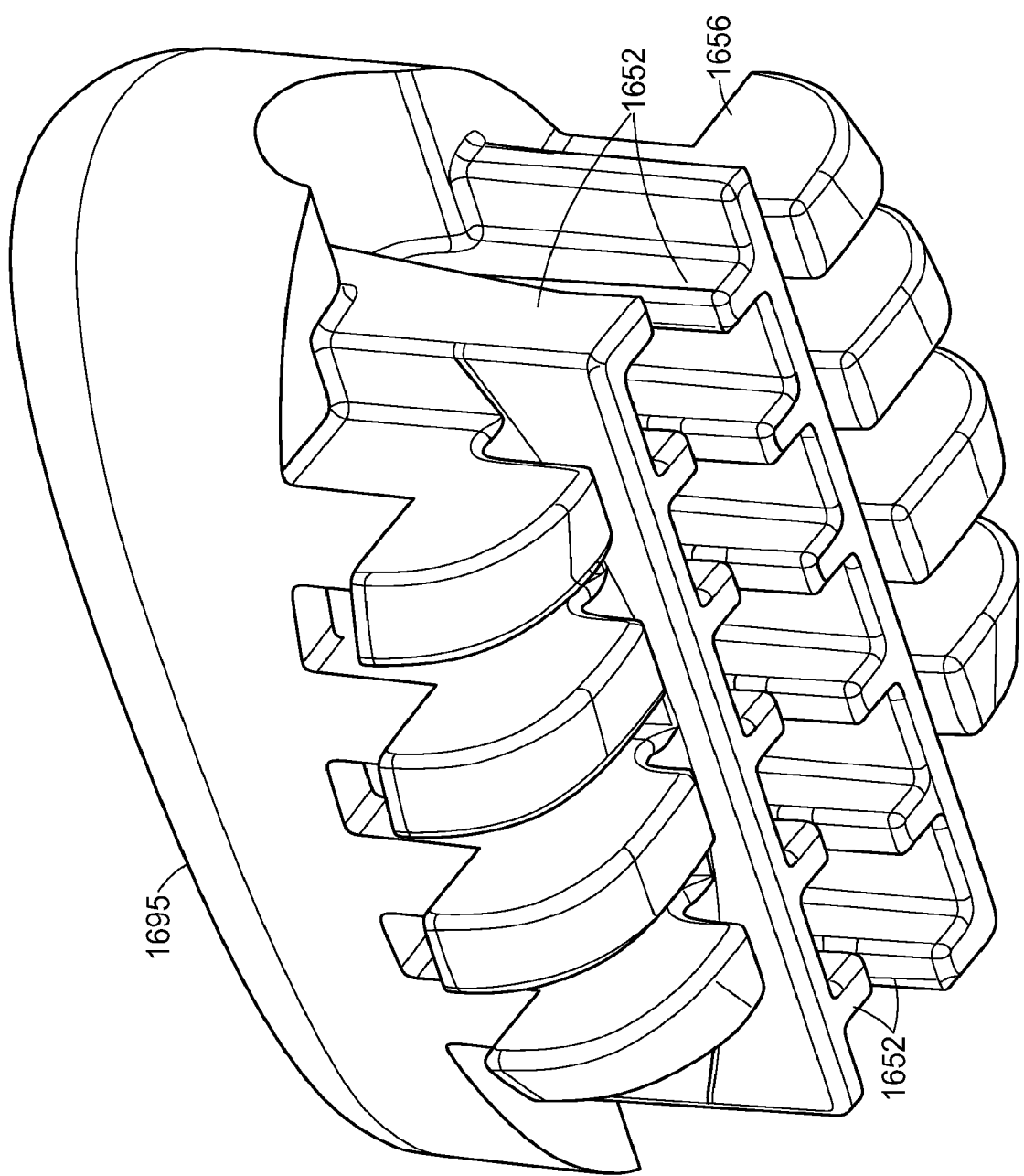
Figure 12C:
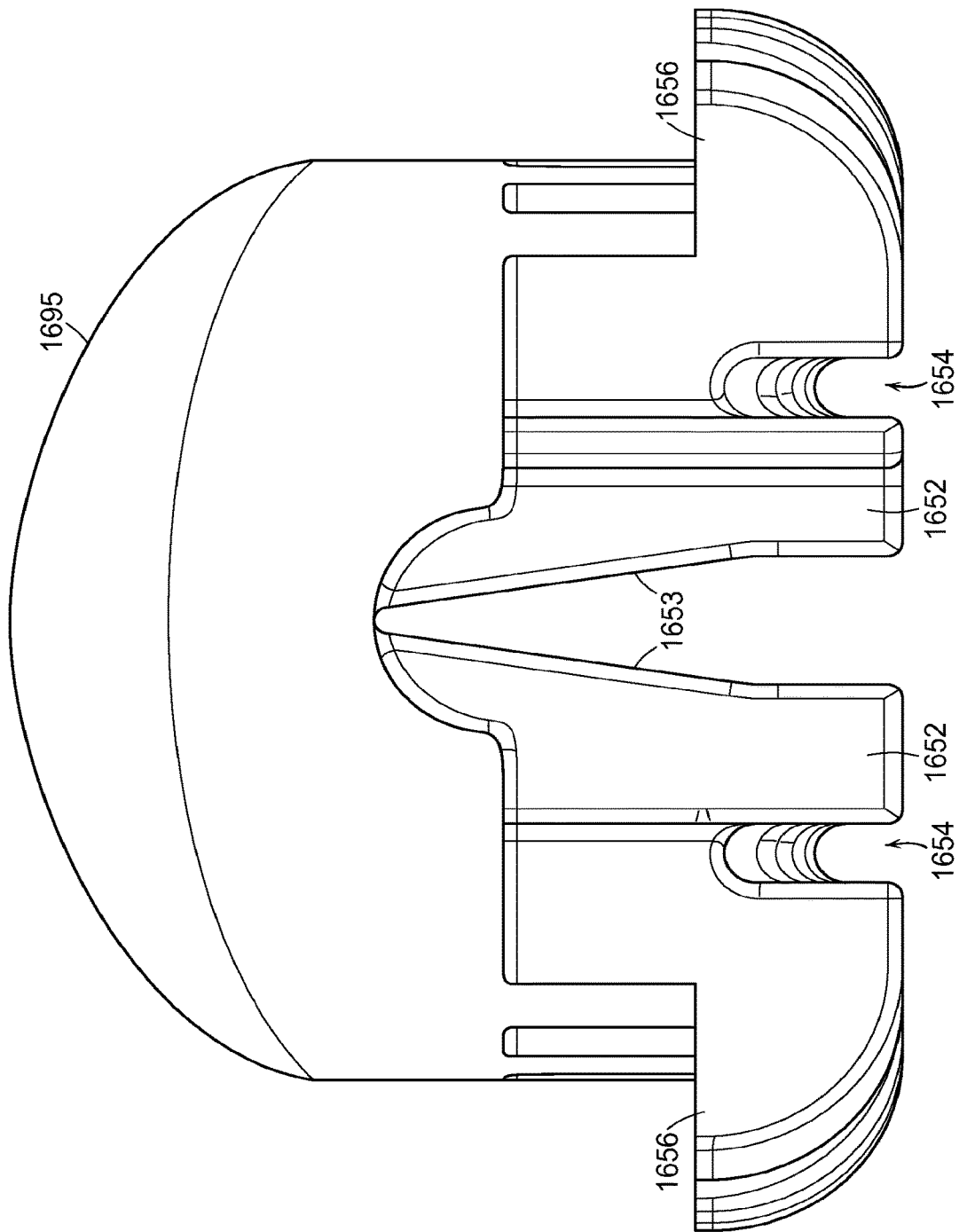

FIGS. 12A-12C are top perspective, bottom perspective, and frontal views, respectively, of the button 1695 of the catheter pusher handle 1692 of FIG. 11A. Shown are the ramped teeth 1652, each of which includes a ramped surface 1653. Also shown are channels 1654 for receiving resilient element 1678. The channels are formed in a bottom portion of the button 1695, between ramped teeth 1652 and feet 1656. The button 1695 and element 1670 (FIG. 13) can be made from any material suitable for transmitting force to the catheter, including plastics, such as ABS, or like materials, as described herein for other buttons and inserts.

Figure 13:
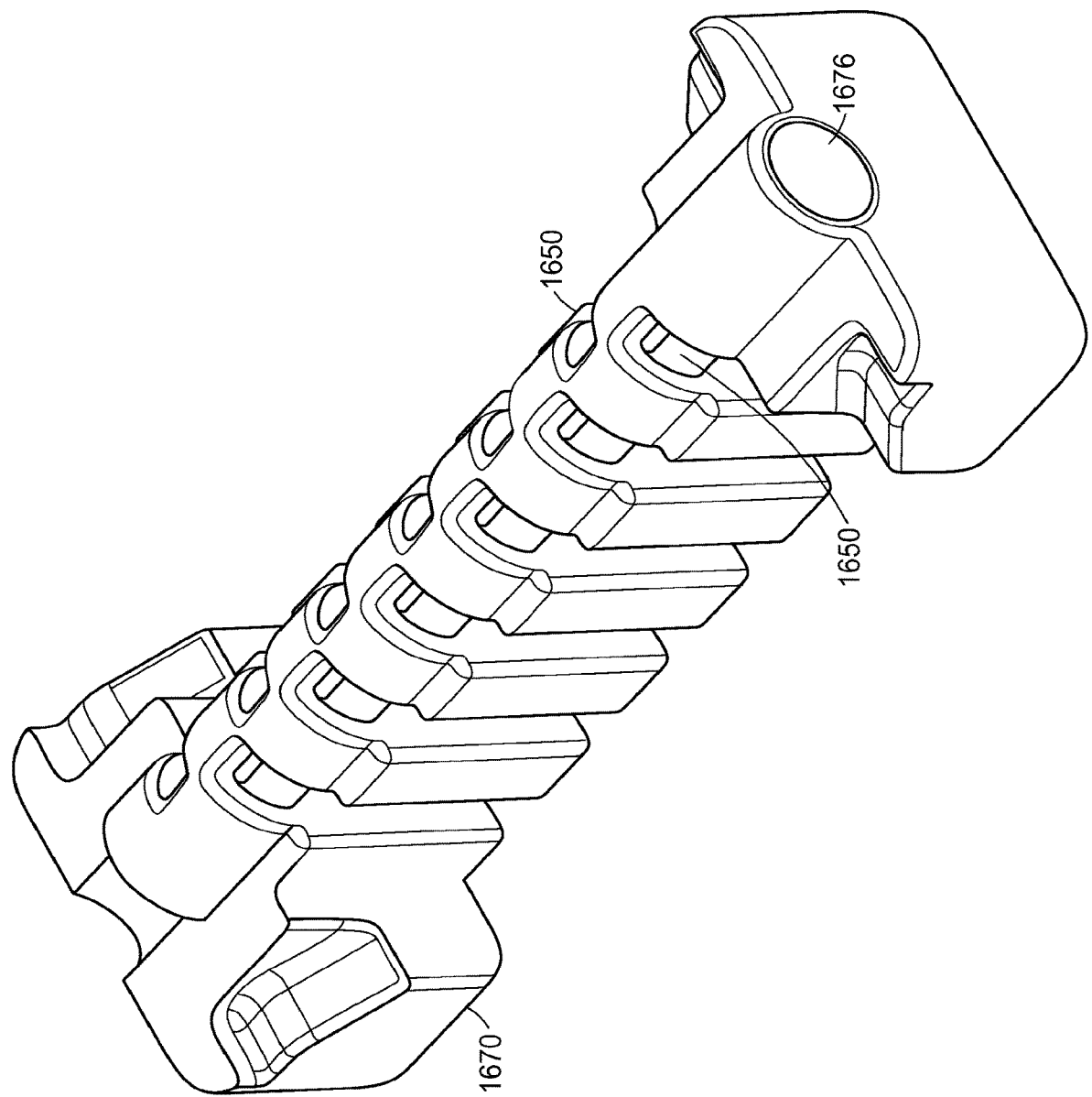
FIG. 13 is a perspective view of an elongated element of the handle of FIG. 11B.

FIG. 13 is a perspective view of the elongated element 1670 of the handle of FIGS. 11A-C. The ramped slots 1650 can be transverse slots, as shown, spaced along a length of the elongated element 1670 on two sides of the element. Further, ramped slots 1650 on one side of the elongated element 1670 can be offset from the ramped slots on the other side of the element. As shown, there can be six slots on each side of the element. Each slot communicates with lumen 1676 of element 1670. Lumen 1676 is configured to receive the inner catheter and the slots 1650 are configured to receive the ramped teeth of the button. Elongated element 1670 can be formed separately from the housing of handle 1692 (FIG. 11B) and may be fixedly attached to the housing. Alternatively, elongated element 1670 can be part of the handle housing, e.g., integrally formed with the housing. An advantage to having the elongated element 1670 formed as a separate part from the housing of the handle is ease of manufacture.

Figure 14:
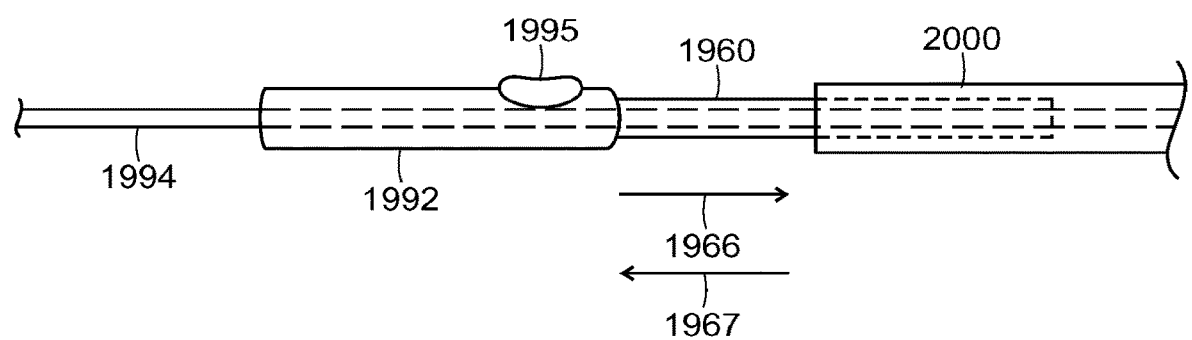
FIG. 14 illustrates advancement of an inner catheter into an outer catheter using a catheter pusher handle having a button on a side of the handle.

FIG. 14 illustrates advancement of an inner catheter 1994 into an outer catheter 2000 using a catheter pusher handle 1992 having a button 1995 on a side of the handle. Applying force in direction 1966 while button 1995 is depressed moves handle 1992, slide tube 1960, and inner catheter 1994, thereby directing a length of inner catheter 1994 along direction 1966, e.g., into an inner catheter lumen defined by an outer catheter 2000, or a handle of an outer catheter. After pressure is released from button 1995, the inner catheter 1994 is no longer retained in the handle, and handle 1992 and slide tube 1960 can be moved along direction 1967. One can then repeat the process of capturing and advancing the inner catheter using handle 1992. In this manner, inner catheter 1994 can be advanced distally, along direction 1966. Slide tube 1960, which may be a rigid tube, such as a metal tube, provides rigid support to inner catheter 1994 to prevent inner catheter 1994 from kinking during advancement of the inner catheter. Typically, slide tube 1960 is attached to the handle so that slide tube and handle move together. As shown, slide tube 1960 slides into the outer catheter 2000, or into the handle of the outer catheter, as the inner catheter is advanced.

In some embodiments, the inner catheter includes an atraumatic tip (e.g., a releasable or deflatable atraumatic ball tip) which facilitates the advancement of the inner catheter through the gastrointestinal tract (e.g., through the proximal intestines). The atraumatic tip allows the inner catheter to be advanced through a gastrointestinal tract, while reducing or eliminating damage or irritation to tissue. The atraumatic tip guides the inner catheter through the distal intestines. The atraumatic ball is in the range of between about 5 millimeters and about 20 millimeters. Preferably, the ball tip is in the range of between about 6.4 millimeters and about 19.2 millimeters in diameter. Most preferably, the atraumatic ball is about 12.7 millimeters in diameter.

Figure 4C:
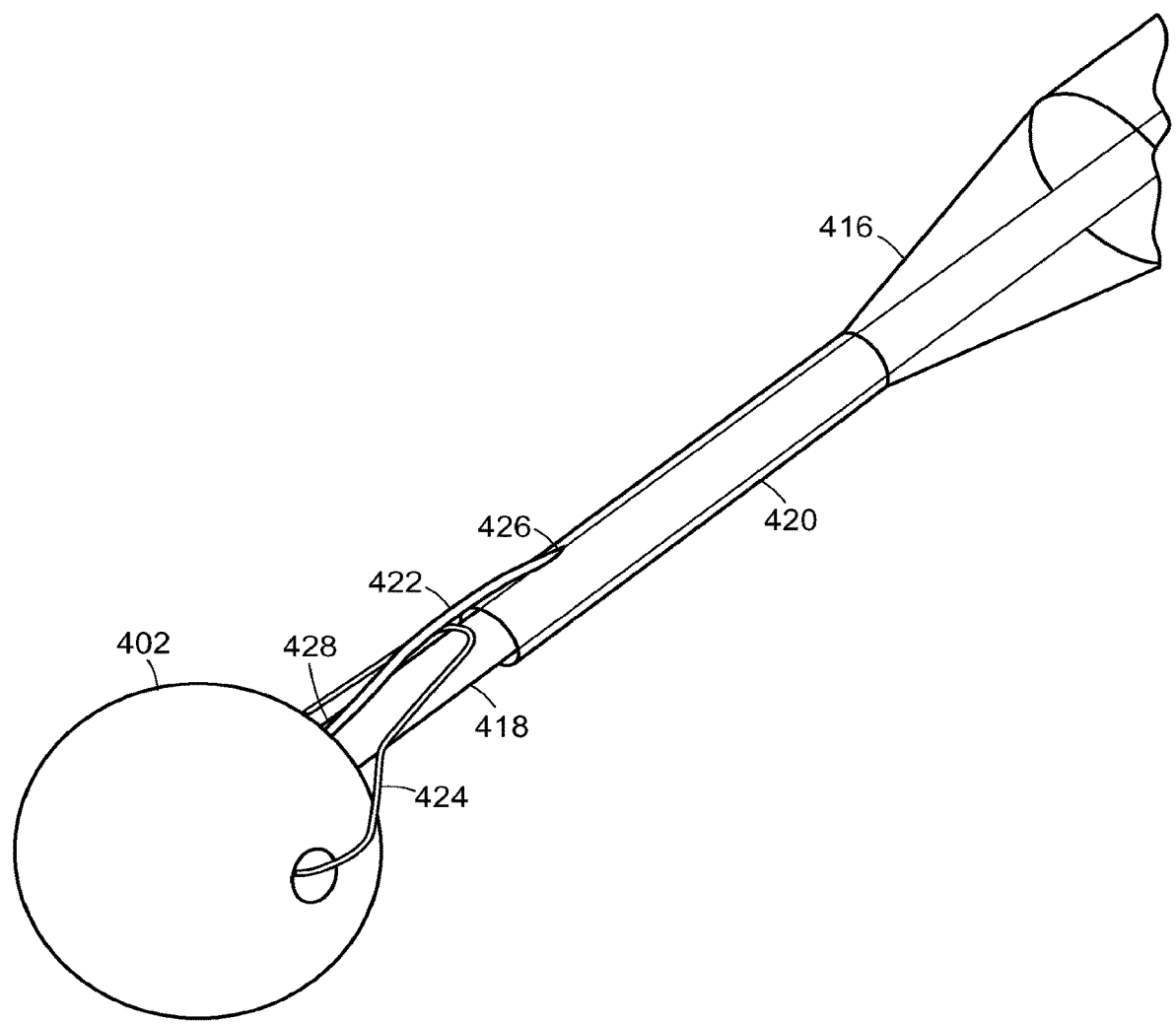

FIG. 4C shows a schematic diagram of the advanced atraumatic tip and distal end 418 of system 400 illustrated in FIG. 4B. Atraumatic ball 402 is secured to ball retaining wire 424. Ball locking wire 422 emerges from a locking wire lumen defined by inner catheter 410 at ball locking wire port 426, extends across a length of inner catheter 410, and passes into the locking wire lumen through ball locking wire port 428. The portion of locking wire 422 that extends between locking wire ports 426 and 428 passes through one or more perforations in distal portion 420 of sleeve 416 as well as through ball retaining wire 424, thereby removably securing both distal portion 420 and atraumatic ball 402 to distal end 418 of inner catheter 410.

Figure 4D:
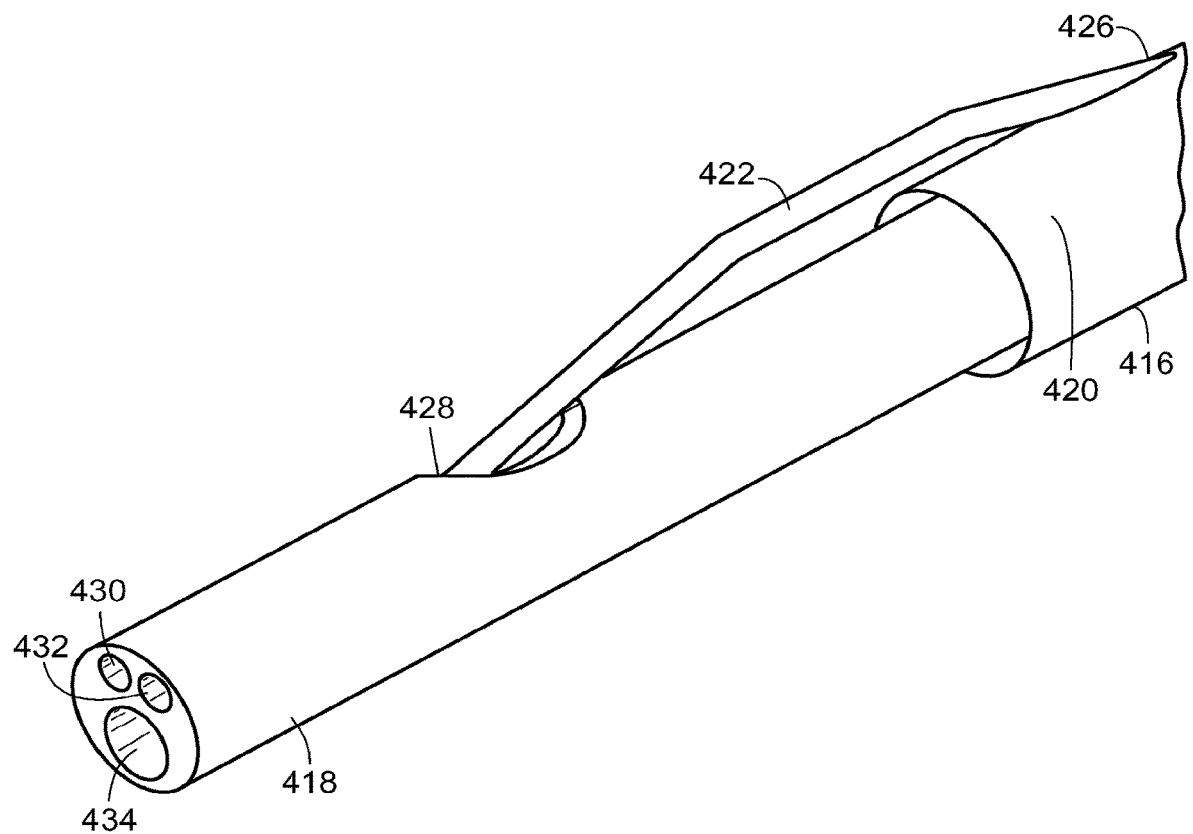

FIG. 4D illustrates a schematic view of distal end 418 of inner catheter 410 of system 400 with atraumatic ball 402 and retaining wire 424 omitted for clarity. Inner catheter 410 defines ball locking wire lumen 430, stiffening wire lumen 434, and tension wire lumen 432. Ball locking wire 422 exits ball locking wire lumen via locking wire port 426, extends through distal portion 420 of sleeve 416, and passes back into ball locking wire lumen 430 through locking wire port 428.

Figure 4E:
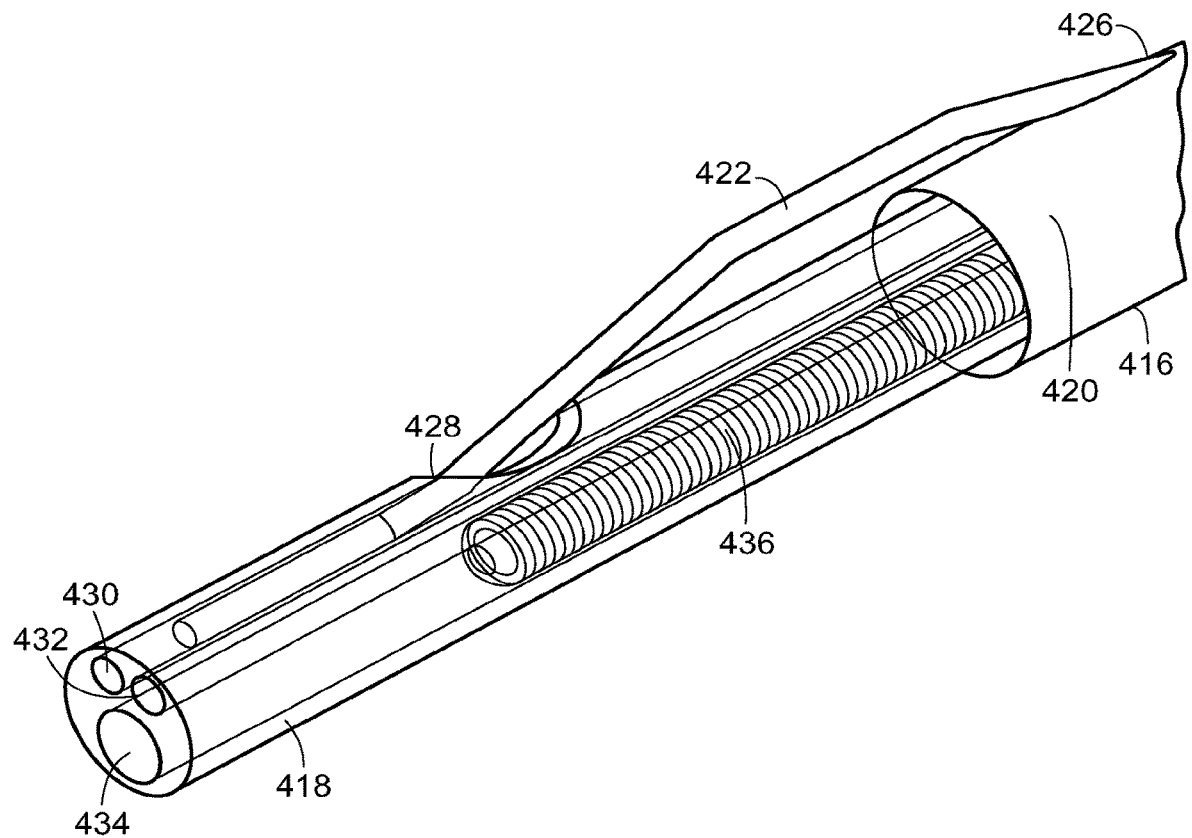

FIG. 4E illustrates a cut-away view of the schematic shown in FIG. 4D. Stiffening wire 436 lies within stiffening wire lumen 434. Stiffening wire 436 facilitates the advancement of the inner catheter through the gastrointestinal tract (e.g., through the proximal intestines) by, for example, providing a desirable amount of rigidity to the inner catheter so that it can negotiate the gastrointestinal tract. In further embodiments, the stiffening wire includes a distal portion that is less rigid than other, more proximal, portions. Inclusion of such a stiffening wire provides an inner catheter that has a distal portion that is less rigid than other, more proximal, portions. In some embodiments of the invention, the stiffening wire is used to eject the releasable ball from the end of the inner catheter by advancing the stiffening wire distally relative to the inner catheter. Optionally, the practitioner of the invention can remove the stiffening wire prior to removal of the inner and/or outer catheters, thereby reducing the rigidity of the inner catheter.

Inner catheter 410 defines tension wire lumen 432. The tension wire provides structural support to inner catheter 410 to prevent unwanted deformations of catheter 410 during insertion or maneuverings within a gastrointestinal tract. For example, the tension wire can be included to prevent inner catheter 410 from elongating or stretching. Such elongating or stretching can cause locking wire 422 to emerge from port 428 prematurely, thereby releasing distal ball 402 and distal portion 420 from distal end 418 at undesirable portions of a placement procedure.

Figure 4F:
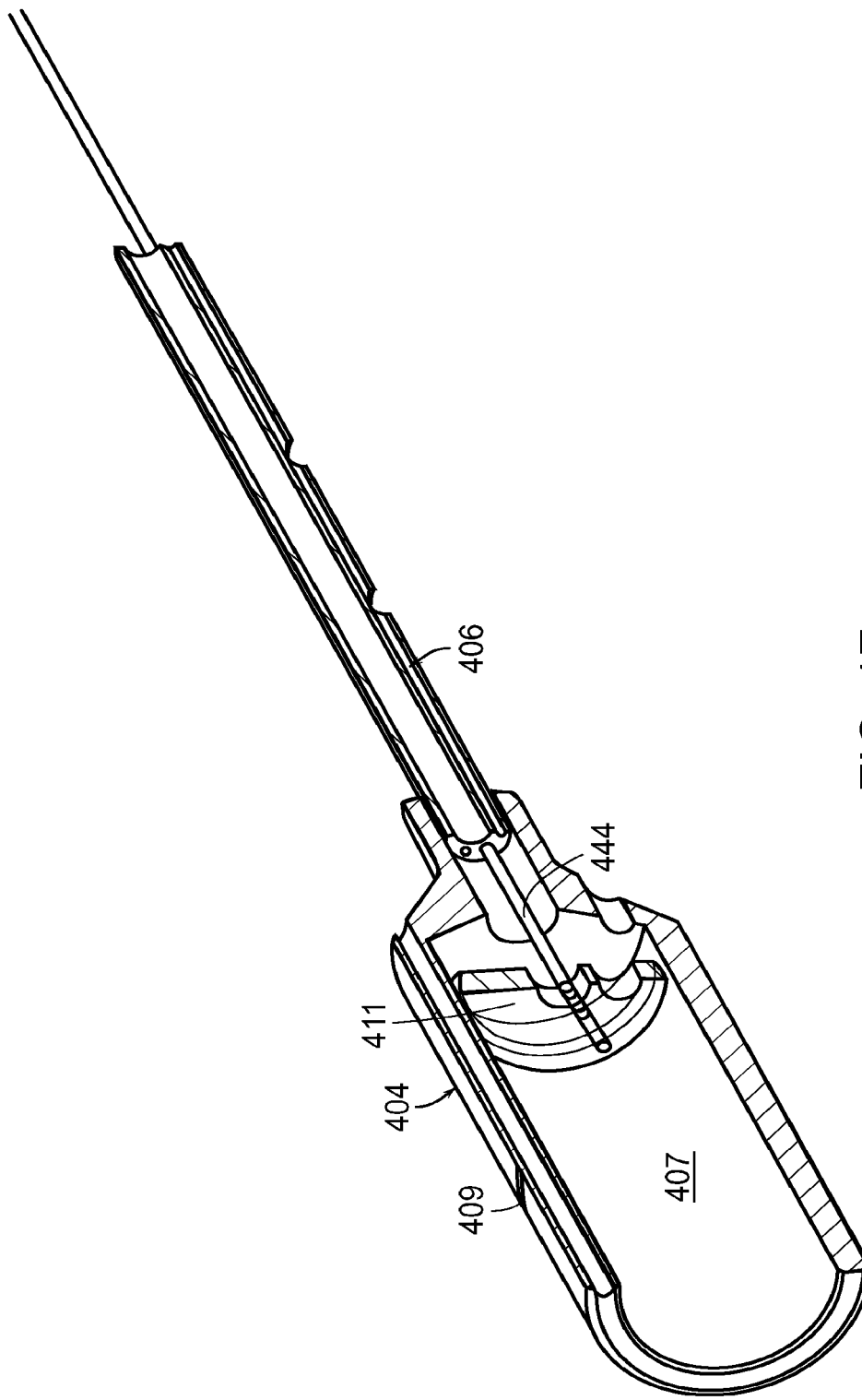

FIGS. 4F-5H illustrate additional embodiments of the invention that include cross sectional views of a portion of container 404. As illustrated in FIG. 4F, container 404 defines storage chamber 407. Container 404 includes visual marker 409 which can be used to determine if container 404 is in a desired location before an anchor is fully expelled from container 404. (FIG. 2K illustrates how a practitioner of the invention uses a visual marker to determine if the container is in a desired location before an anchor is fully removed from the container.)

Figure 4G:
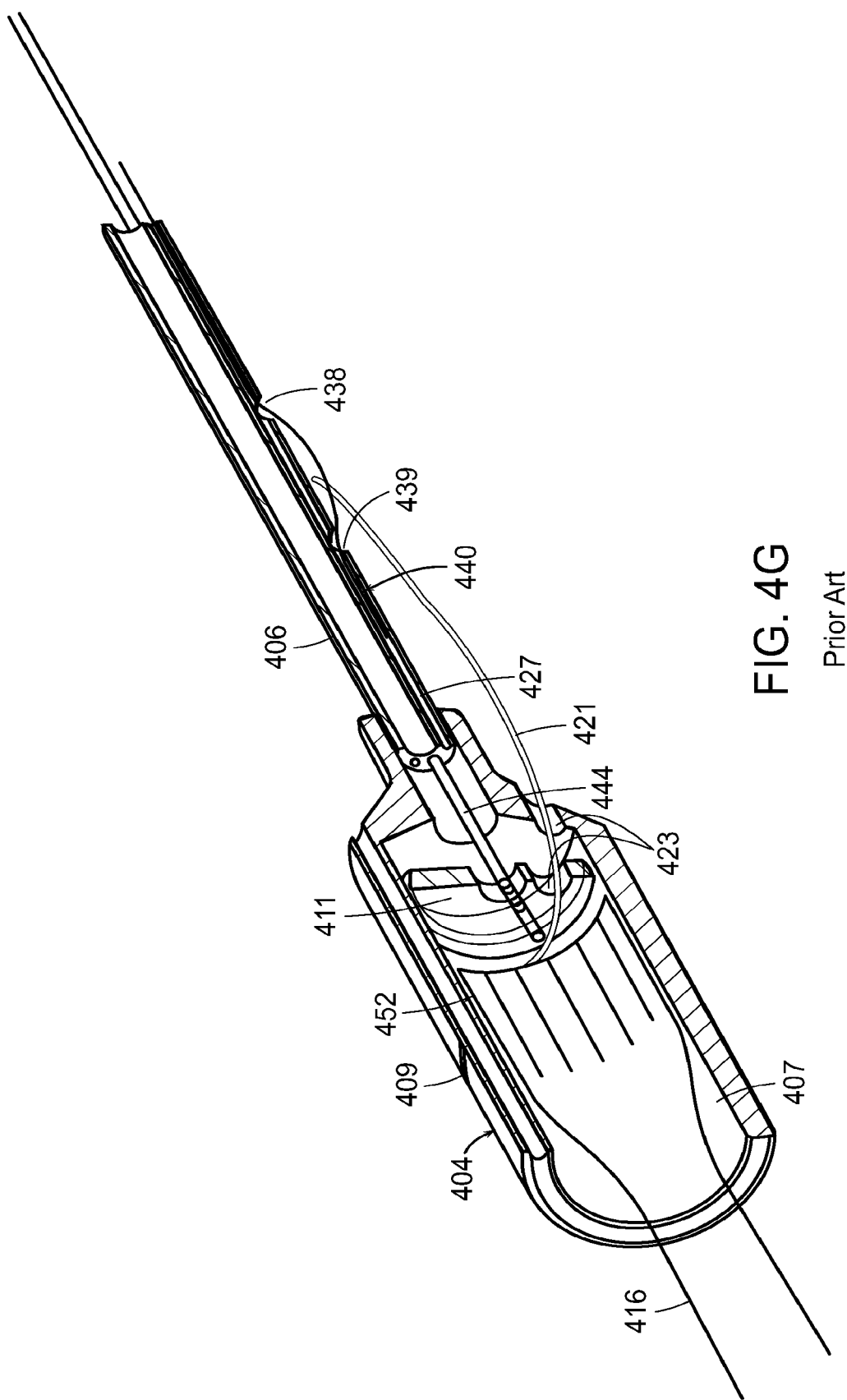
Figure 4H:
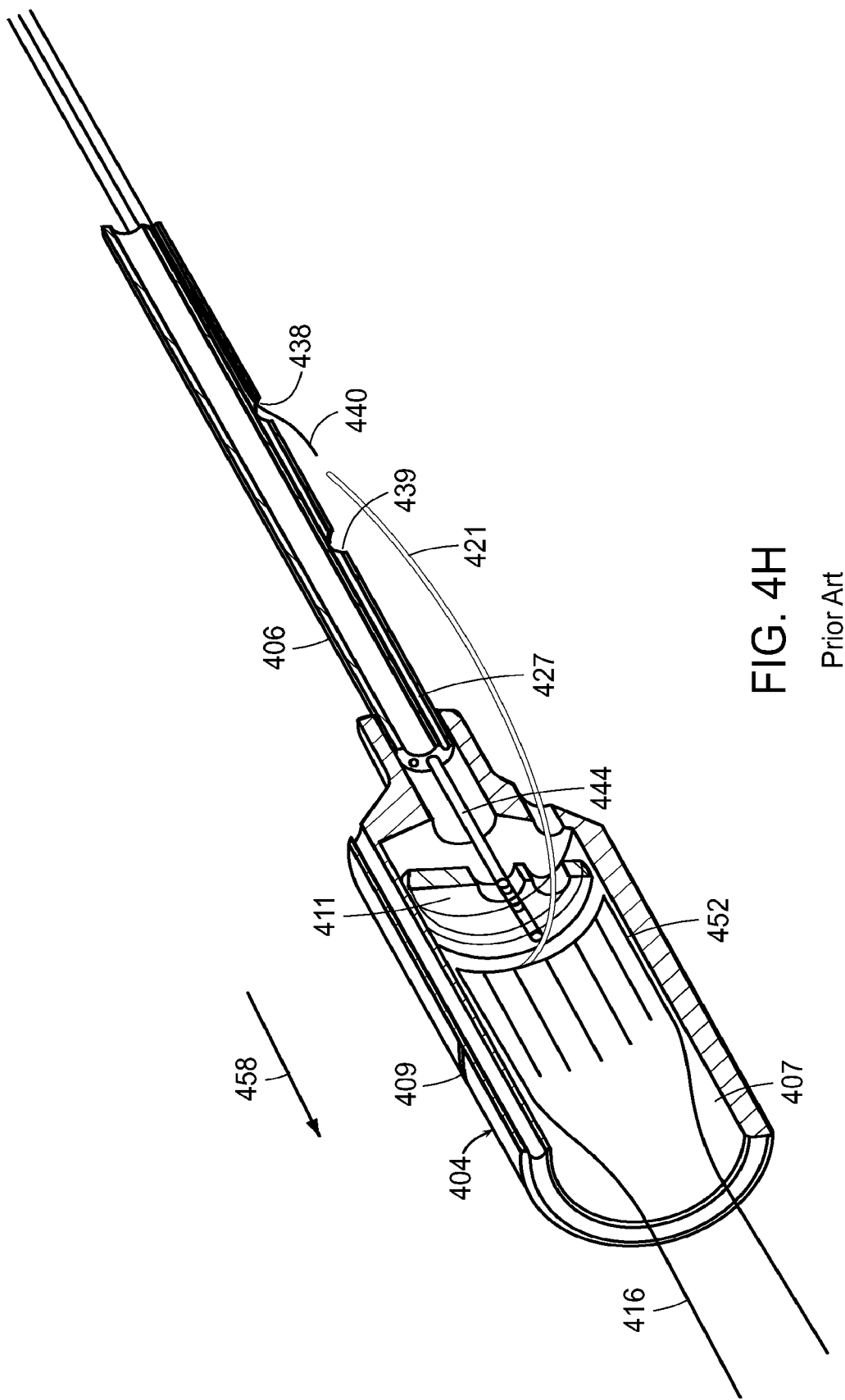
Figure 41:
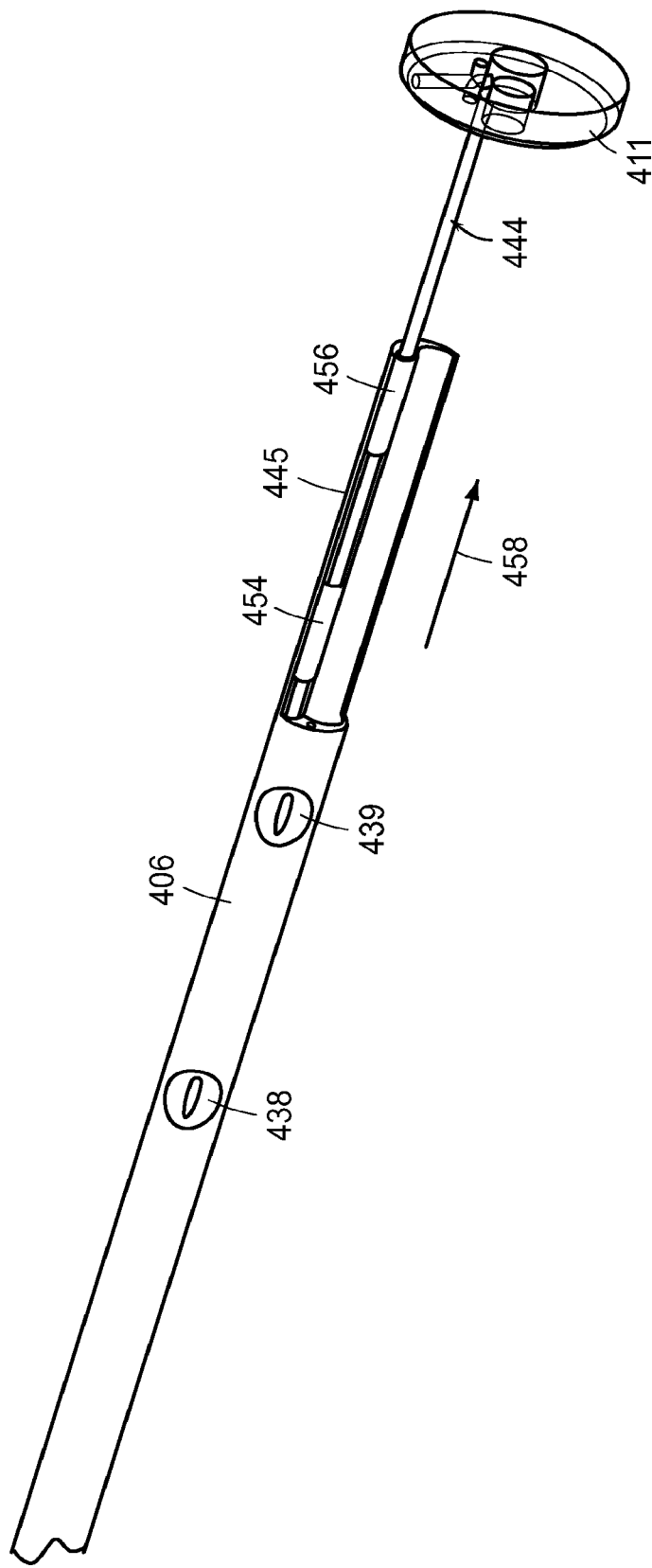

Container 404 is attached or assembled to outer catheter 406 (a portion of which is omitted from FIGS. 4F-4H for clarity). Anchor pusher wire 444 extends through an anchor pusher wire lumen which is defined by outer catheter 406. The distal end of anchor pusher wire 444 is attached or assembled to anchor pusher plate 411.

FIG. 4G illustrates container 404 and a stored portion of a gastrointestinal device that includes anchor 452 and a proximal portion of sleeve 416. Anchor 452 is collapsed or contracted and stored within chamber 407. In some embodiments, the anchor stored within the chamber(s) defined by a container assembly is a self-expanding anchor. Anchor 452 is contained or stored in container 404 during portions of a placement method that include directing the container assembly and portions of the gastrointestinal device to various locations within a gastrointestinal tract of a mammal. (FIGS. 2E-2J illustrate portions of a placement method that include directing a container assembly and portions of a gastrointestinal device to various locations within a gastrointestinal tract of a mammal.)

The proximal end of the gastrointestinal device includes one or more drawstrings which are attached to the proximal end of the device via perforations in the sleeve material. In some embodiments, one or more of these drawstrings are used to releasably secure or lock anchor 452 within container 404. For example, anchor retaining wire 421 extends out of the proximal end of container 404 via anchor retaining wire port 423 defined by anchor pusher plate 411 and container 404. Anchor locking wire 440 extends through anchor locking wire lumen 427 which is defined by outer catheter 406. Wire 440 emerges from lumen 427 via anchor locking wire port 438, extends through drawstring 421, and extends back into lumen 427 via anchor locking wire port 439.

After sleeve 416 has been deployed to a desired extent and container 404 is in the desired location, anchor 452 and the proximal portion of sleeve 416 can be released from container 404. FIG. 4H illustrates the release of anchor 452 from container 404. Anchor locking wire 440 is pulled proximally at anchor locking wire port 438 on the proximal end of outer catheter 406 (not illustrated in FIG. 4H), thereby pulling the distal portion of wire 440 from anchor locking wire port 439 and disengaging wire 440 from anchor retaining wire 421.

Once anchor 452 has been released from anchor locking wire 440, anchor 452 and proximal portion of sleeve 416 are expelled from container 404. To expel anchor 452 and the proximal portion of sleeve 416, a practitioner pushes anchor pusher wire 444 distally, thereby directing plate 411 along a direction parallel to direction 458 and forcing anchor 452 from the distal end of container 404. Optionally, or in addition, inner catheter 410 is advanced further, thereby causing distal portion 420 of sleeve 416 and the attached anchor 452 to advance distally relative to container 404 until anchor 452 emerges from container 404. In some embodiments, one or more of the chambers of the container assembly is lined with a layer of metal or metal alloy, thereby preventing portions of the anchor from adhering to the inner container walls and facilitating removal of the anchor from the container assembly. FIGS. 2K-2L illustrate an anchor emerging from a container assembly.

FIG. 4I illustrates another view of pusher plate 411, omitting container 404 and portions of outer catheter 406 for clarity. Pusher plate wire 444 and pusher plate wire lumen 445 includes a mechanism to prevent a practitioner of the invention from directing plate 411 distally to such an extent that plate 411 emerges from the distal end of container 404. The mechanism includes moving stop 454 and static stop 456 which have dissimilar diameters. The dissimilar diameters prevent moving stop 454 from translating past static stop 456, thereby preventing excess distal translation of wire 444 relative to outer catheter 406.

Moving stop 454 is attached to, or formed by a portion of, wire 444 and has an outer diameter that is greater than the outer diameter of the portions of wire 444 that are distal from stop 454. Moving stop 454 moves or translates with wire 444 relative to outer catheter 406 along a direction that is parallel to direction 458.

Static stop 456 is attached to, or formed by a portion of, outer catheter 406. Stop 456 remains stationary with respect to catheter 406 as wire 444 is translated distally. Static stop 456 defines an inner diameter that is less than the diameter of moving stop 454 but greater than the diameter of the portion of wire 444 that is distal to moving stop 454. Hence, when wire 444 is sufficiently translated distally along a direction parallel to direction 458, moving stop 454 contacts static stop 456, thereby preventing further distal translation of wire 444 along a direction parallel to direction 458. In this manner, the mechanism allows a practitioner of the invention to sufficiently translate plate 411 distally so as to expel a gastrointestinal implant device from a container while simultaneously preventing plate 411 from emerging form the distal end of the container.

Figure 4J:
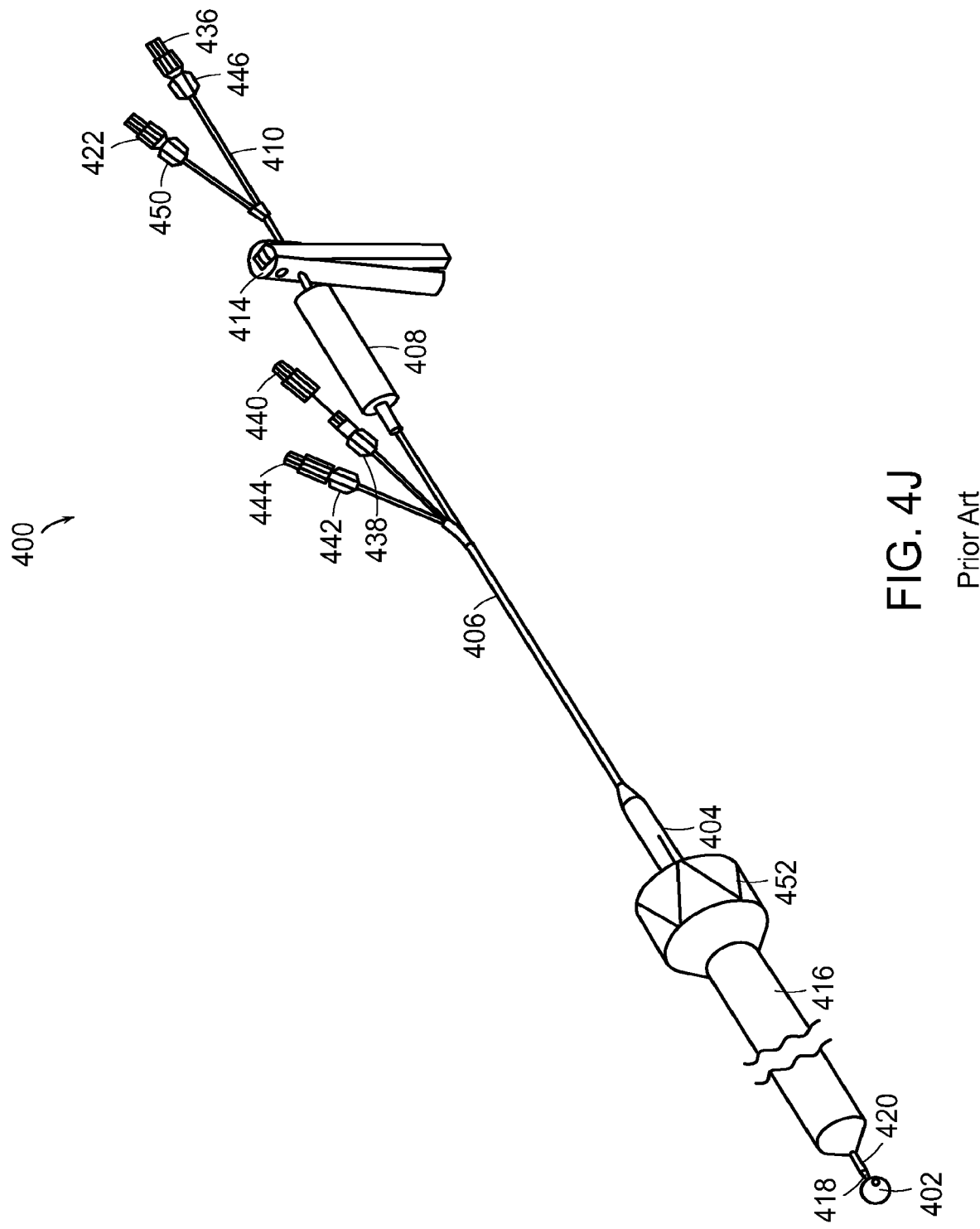

After anchor 452 is free of container 405, anchor 452 expands and is secured to a desired location within the gastrointestinal tract. FIG. 4J illustrates system 400 after anchor portion 452 has been expelled from container assembly 404. Anchor locking wire 440 has been pulled proximally and away from anchor locking wire port 438 and anchor 452 has expanded after leaving container 404. Anchor 452 secures the gastrointestinal device at a desired location within the gastrointestinal tract of a mammal.

Figure 4K:
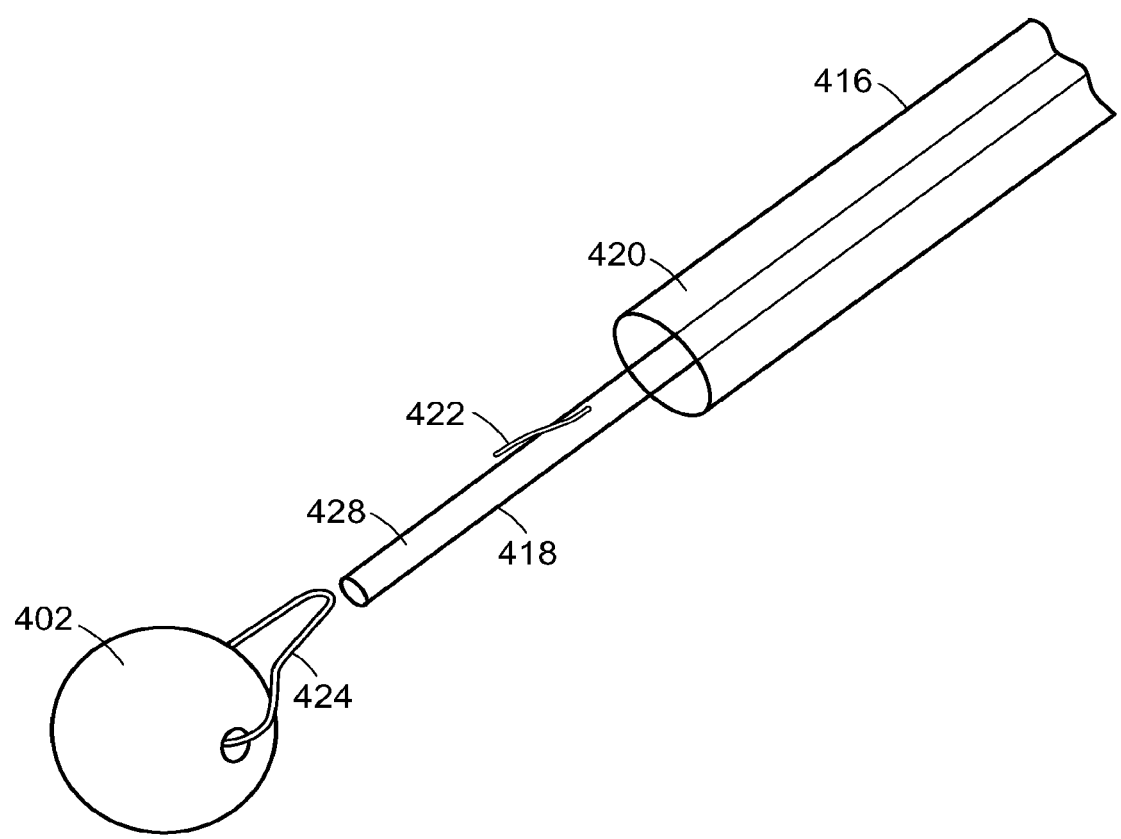

After anchor 452 has been deployed, distal portion 420 of sleeve 416 and ball 402 can be released from distal end 418 of inner catheter 410. FIG. 4K illustrates the release of ball 402 and distal portion 420 of sleeve 416. Ball locking wire 422 is pulled proximally at ball locking wire port 450, thereby pulling the distal portion of ball locking wire 422 from ball locking wire port 428 and disengaging ball locking wire 422 from ball retaining wire 424 and the perforation(s) on distal portion 420 of sleeve 416. Ball 402 disengages distal end 418 of inner catheter 410 and is passed through the remainder of the gastrointestinal tract by natural peristalsis.

Optionally, a fluid (e.g., a gas or liquid) is directed into the gastrointestinal sleeve after the anchor has been deployed.

Figure 4L:
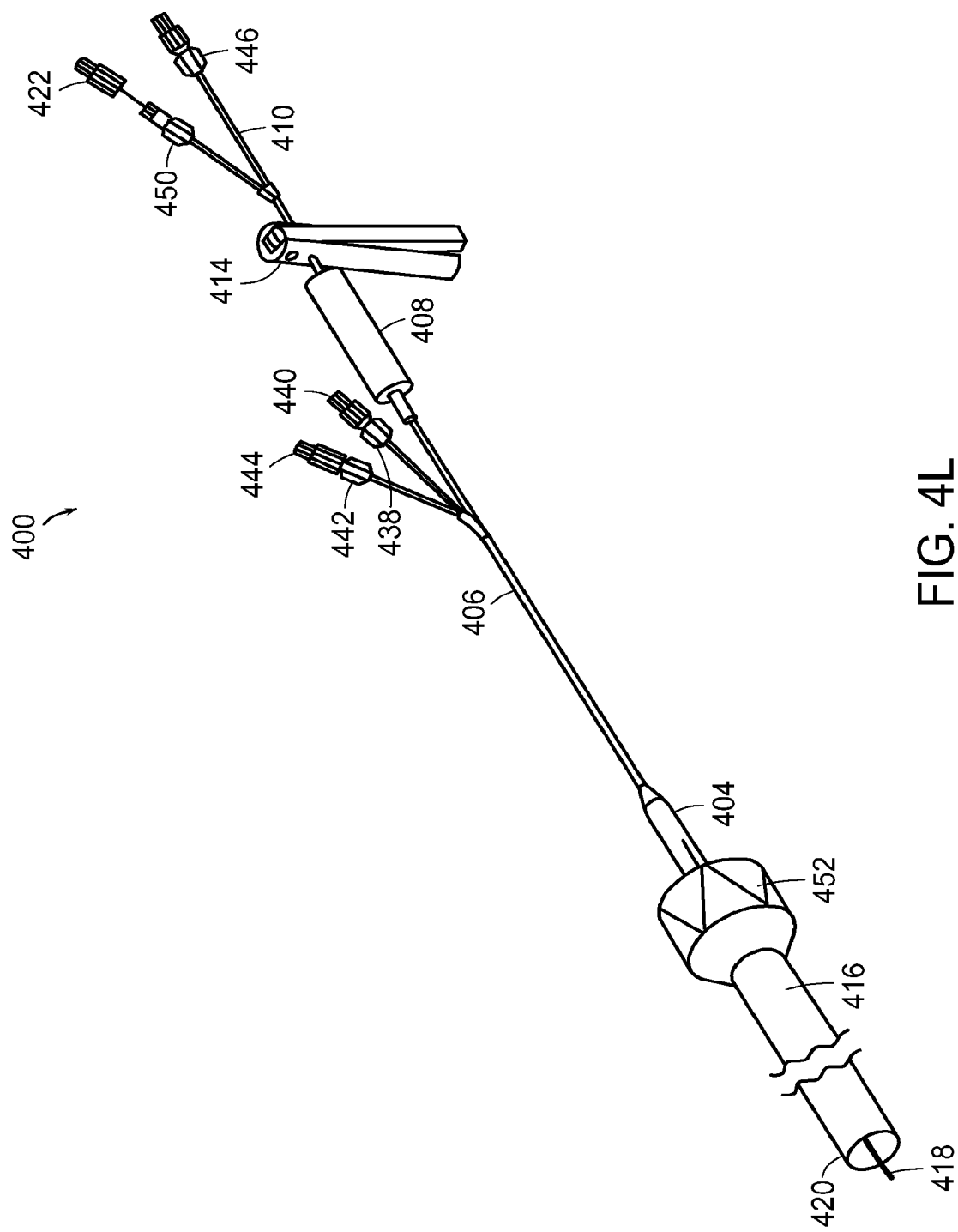

At such a point in a placement process, stiffening wire 436 is no longer needed and can be removed from system 400 by pulling wire 436 proximally at stiffening wire port 446, and removing it entirely from stiffening wire lumen 434. Optionally, a fluid can then be directed through lumen 434 and into sleeve 416, thereby expanding at least a portion of sleeve 416. FIG. 4L illustrates system 400 after stiffening wire 436 has been removed and a fluid has been directed through stiffening wire port 446, through stiffening wire lumen 434, and into sleeve 416. Distal portion 420 of sleeve 416 has been expanded. Ball locking wire 422 has been pulled proximally from ball locking wire port 450. FIG. 2M illustrates the release of a ball tip from an inner catheter.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A catheter handle for a delivery system of a gastrointestinal device, the catheter handle comprising:
    an inner catheter movable within the handle;
    an elongated element within the handle, the elongated element surrounding a portion of the inner catheter, an inner diameter of the elongated element being about the same as or greater than an outer diameter of the inner catheter, wherein the elongated element comprises slots and the button comprises ramped teeth aligned with the slots; and
    a button on a side of the handle, the button configured to cause engagement of the inner catheter via the elongated element when the button is depressed, wherein the button is configured to cause the ramped teeth to engage the inner catheter via the slots when the button is depressed and press the inner catheter against the elongated element, thereby retaining the inner catheter within the handle.

2. The catheter handle of claim 1, wherein the slots are transverse slots spaced along a length of the elongated element on two sides of the elongated element.

3. The catheter handle of claim 2, wherein the slots on one side of the elongated element are offset from the slots on the other side of the elongated element.

4. The catheter handle of claim 3, wherein the slots are ramped, and wherein the ramped teeth and ramped slots define multiple complementary features.

5. The catheter handle of claim 1, further including a resilient element configured to non-plastically deform when the button is depressed and to provide a restoring force to cause the ramped teeth to disengage the inner catheter when the button is released.

6. The catheter handle of claim 1, wherein the elongated element is a surround tube, and wherein the button is configured to bend the surround tube and non-plastically deform the inner catheter when the button is depressed, thereby retaining the inner catheter within the handle.

7. The catheter handle of claim 6, wherein:
    (a) the surround tube comprises a silicone tube,
    (b) the button comprises a rigid thermoplastic, and/or
    (c) the button bends the surround tube between ends of the surround tube, the ends being held in place by the handle.

8. The catheter handle of claim 1, wherein the elongated element is a lever including a lever jaw, and wherein the button is configured to cause the lever to rotate about a pivot and the lever jaw to engage the inner catheter when the button is depressed, thereby retaining the inner catheter within the handle.

9. The catheter handle of claim 8, wherein:
    (a) the lever defines a lumen through which the inner catheter extends;
    (b) the lever is configured to translate a force with which the button is depressed into a force with which the inner catheter is engaged at an amplification ratio in the range of about 1:1 to about 2:1; and/or
    (c) the lever jaw includes directional teeth; and/or further including a resilient element configured to non-plastically deform when the button is depressed and to provide a restoring force to cause the lever jaw to disengage the inner catheter when the button is released.

10. The catheter handle of claim 1, wherein the inner catheter comprises an inner extension catheter configured to draw a portion of a sleeve from an anchor and from a container assembly as the anchor is retained therein.

11. A method of retaining an inner catheter for delivery of a gastrointestinal device, the method comprising:
    surrounding a portion of the inner catheter that is movably disposed within a handle with an elongated element within the handle;
    depressing a button on a side of the handle, to engage the inner catheter via the elongated element; and
    retaining the inner catheter within the handle based on the resulting engagement of the inner catheter, wherein:
    (a) the elongated element comprises slots and the button includes ramped teeth aligned with the slots, and wherein depressing the button causes the ramped teeth to engage the inner catheter via the slots and press the inner catheter against the elongated element;
    (b) the elongated element is a surround tube, and wherein depressing the button bends the surround tube and non-plastically deforms the inner catheter;
    (c) the elongated element is a lever including a lever jaw, and wherein depressing the button causes the lever to rotate about a pivot and the jaw of the lever to engage the inner catheter; and/or
    (d) the method further comprising advancing the inner catheter retained within the handle into a lumen of an outer catheter.

12. The method of claim 11, further comprising drawing a portion of a sleeve from an anchor, and from a container assembly, as the anchor is retained therein, using the inner catheter.

13. A catheter handle for a delivery system of a gastrointestinal device, the catheter handle comprising:
    (a) an inner catheter movable within the handle;
    (b) an elongated element within the handle; and
    (c) a button on a side of the handle; wherein
        (i) the elongated element comprises slots and the button comprises ramped teeth aligned with the slots, wherein the button is configured to cause the ramped teeth to engage the inner catheter via the slots when the button is depressed, thereby retaining the inner catheter within the handle;
        (ii) the elongated element is a surround tube, wherein depressing the button bends the surround tube and non-plastically deforms the inner catheter; and/or (iii) the elongated element is a lever including a lever jaw, wherein depressing the button causes the lever to rotate about a pivot and the jaw of the lever to engage the inner catheter.

14. The catheter handle of claim 13, wherein the elongated element is a surround tube, wherein depressing the button bends the surround tube and non-plastically deforms the inner catheter.

15. The catheter handle of claim 13, wherein the elongated element is a lever including a lever jaw, wherein depressing the button causes the lever to rotate about a pivot and the jaw of the lever to engage the inner catheter.

* * * * *